US010077309B2

(12) United States Patent
Chroneos et al.

(10) Patent No.: US 10,077,309 B2
(45) Date of Patent: Sep. 18, 2018

(54) COMPOSITIONS AND METHODS FOR TARGETING OF THE SURFACTANT PROTEIN A RECEPTOR

(71) Applicant: The Penn State Research Foundation, University Park, PA (US)

(72) Inventors: Zissis Chroneos, Hershey, PA (US); Neil Christensen, Harrisburg, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 63 days.

(21) Appl. No.: 15/323,858

(22) PCT Filed: Jul. 14, 2015

(86) PCT No.: PCT/US2015/040304
§ 371 (c)(1),
(2) Date: Jan. 4, 2017

(87) PCT Pub. No.: WO2016/010978
PCT Pub. Date: Jan. 21, 2016

(65) Prior Publication Data
US 2017/0158768 A1    Jun. 8, 2017

Related U.S. Application Data

(60) Provisional application No. 62/121,830, filed on Feb. 27, 2015, provisional application No. 62/024,314, filed on Jul. 14, 2014.

(51) Int. Cl.
*C07K 16/28* (2006.01)
*A61K 39/00* (2006.01)

(52) U.S. Cl.
CPC .... *C07K 16/2851* (2013.01); *A61K 2039/505* (2013.01); *A61K 2039/507* (2013.01); *C07K 2317/24* (2013.01); *C07K 2317/34* (2013.01); *C07K 2317/52* (2013.01); *C07K 2317/565* (2013.01); *C07K 2317/76* (2013.01)

(58) Field of Classification Search
CPC ............ C07K 16/2851; C07K 2317/76; C07K 2317/24; C07K 2317/52; C07K 2317/565; A61K 2039/505
See application file for complete search history.

(56) References Cited

U.S. PATENT DOCUMENTS

| 7,425,421 B2 | 9/2008 | Dertinger |
| 7,867,447 B2 | 1/2011 | Dertinger |
| 8,076,095 B2 | 12/2011 | Dertinger |
| 8,586,321 B2 | 11/2013 | Dertinger |
| 8,748,113 B2 | 6/2014 | Matsui et al. |
| 8,889,369 B2 | 11/2014 | Dertinger |
| 9,285,365 B2 | 3/2016 | Dertinger |
| 2015/0030636 A1 | 1/2015 | Dylla et al. |
| 2015/0259418 A1 | 9/2015 | Barth et al. |

FOREIGN PATENT DOCUMENTS

WO    2009/036379 A2    3/2009

OTHER PUBLICATIONS

Samten, B., et al., An antibody against the surfactant protein A (SP-A)-binding domain of the SP-A receptor inhibits T cell-mediated immune responses to *Mycobacterium tuberculosis*, Journal of Leukocyte Biology, Jul. 1, 2008, vol. 84, No. 1, pp. 115-123.
Jakel, A., et al., Ligands and receptors interacting with SP-A and SP-D, Frontiers in Bioscience, Jun. 1, 2013, vol. 18, pp. 1129-1140.
Sever-Chroneos, Z., et al., Surfactant Protein A (SP-A)-mediated Clearance of *Staphylococcus aureus* Involves Binding of SP-A to the Staphylococcal Adhesin Eap and the Macrophage Receptors SP-A Receptor 210 and Scavenger Receptor Class A, The Journal of Biological Chemistry, Feb. 11, 2011, vol. 286, No. 6, pp. 4854-4870.
Yang, C, et al., Identification of the Surfactant Protein A Receptor 210 as the Unconventional Myosin 18A, The Journal of Biological Chemistry, Aug. 8, 2005, vol. 280, No. 41, pp. 34447-34457.
Yang, L., et al., SP-R210 (Myo18A) Isoforms as Intrinsic Modulators of Macrophage Priming and Activation, PLoS One, May 12, 2015, vol. 10, No. 5, pp. 1-29.
Mori, et al., Subcellular localization and dynamics of MysPDZ (Myo18A) in live mammilian cells, Biochemical and Biophysical Research Communications, vol. 326, No. 2, pp. 491-498. 2005.
Mori, et al., Genome Structure and Differential Expression of Two Isoforms of a Novel PDZ-Containing Myosin (MysPDZ) (Myo18A), Journal of Biochemistry, vol. 133, No. 4, pp. 405-413. 2003.
Furusawa, et al., Isolation of a Novel PDZ-Containing Myosin from Hematopoietic Supportive Bone Marrow Stromal Cell Lines, Biochemical and Biophysical Research Communications, vol. 270, No. 1, pp. 67-75. 2000.
Yang, et al., Targeting of the surfactant protein a receptor SP-R210(L) variant by influenza A virus in macrophages, The Journal of Immunology, vol. 192, supplment No. 1, abstract. May 1, 2014.

*Primary Examiner* — Ruixiang Li
(74) *Attorney, Agent, or Firm* — Hodgson Russ LLP

(57) ABSTRACT

Provided are compositions and methods for use in prophylaxis, therapy and diagnosis of conditions which involve surfactant protein receptors (SPR) including the SPR for surfactant proteins A (SPA). Specific binding partners, including mono-clonal antibodies, for the SP-R210L and SP-R210S isoforms, and methods of using such binding partners are included. Fragments of the monoclonal antibodies, and fusion proteins that contain them are also included. Also provided are methods for prophylaxis and/or therapy for an individual in need thereof by administering to the individual an effective amount of monoclonal antibody or antigen binding fragment thereof. The monoclonal antibodies are bind with specificity to epitopes in one or both of the SP-R210L and SP-R210S isoforms.

Figure 1:
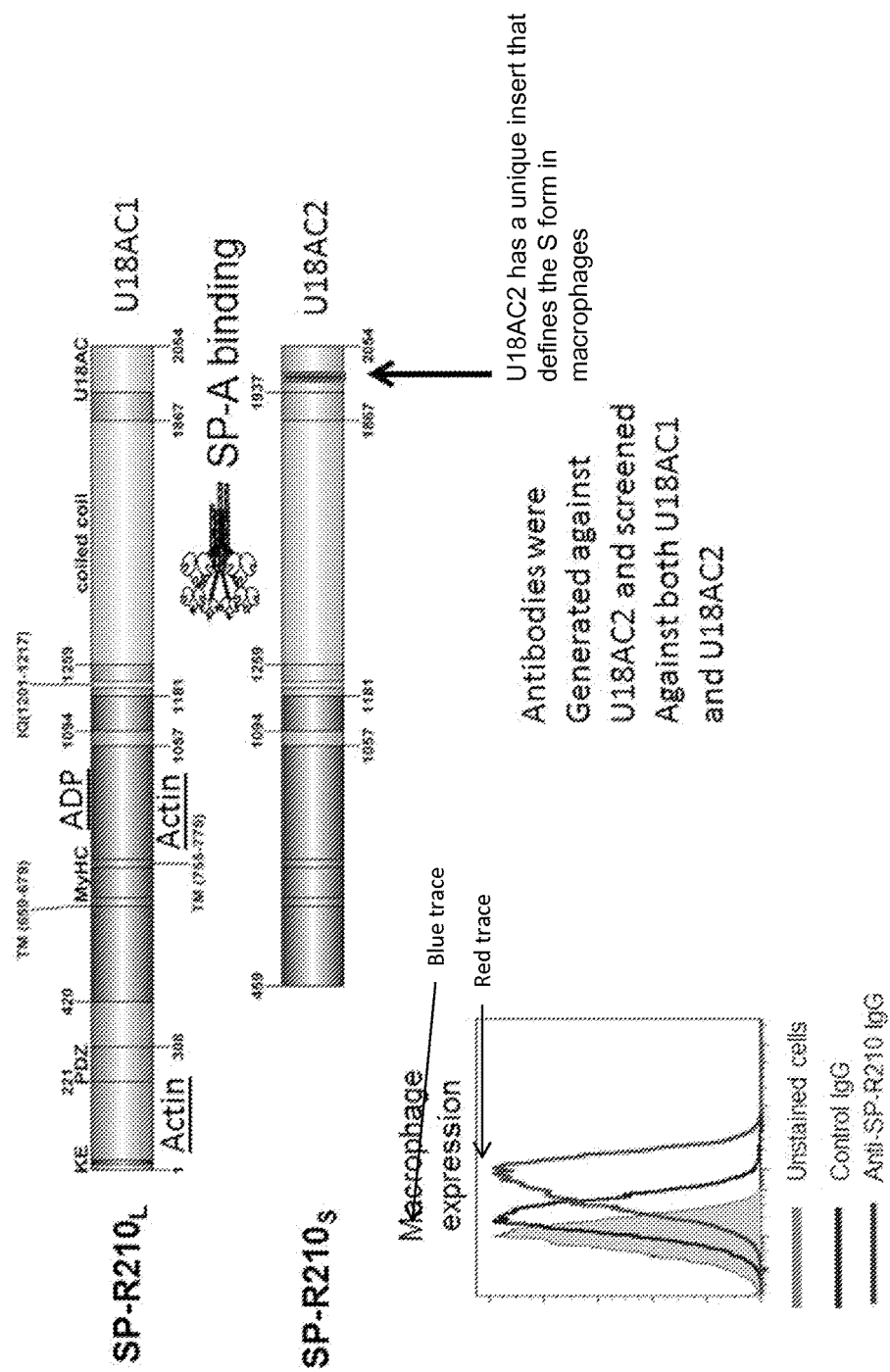

11 Claims, 37 Drawing Sheets
Specification includes a Sequence Listing.

Figure 2

```
Ms SP-R210ScooH  EDEMESDENEDLINSLQDMVTKYQKKKNKLEGDSDVDSELEDRVDGVKSWLSKNKGPSKA 60
Ms SP-R210LcooH  EDEMESDENEDLINS---------------EGDSDVDSELEDRVDGVKSWLSKNKGPSKA 45
Hu SP-R210ScooH  EDEMESDENEDLINSLQDMVTKYQKRKNKLEGDSDVDSELEDRVDGVKSWLSKNKGPSKA 60
Hu SP-R210LcooH  EDEMESDENEDLINS---------------EGDSDVDSELEDRVDGVKSWLSKNKGPSKA 45
                                *

Ms SP-R210ScooH  PSDDGSLKSSSPTSHWKPLAPDPSDDEHDPVDSISRPRFSHSYLSDSDTEAKLTETSA 118
Ms SP-R210LcooH  PSDDGSLKSSSPTSHWKPLAPDPSDDEHDPVDSISRPRFSHSYLSDSDTEAKLTETSA 103
Hu SP-R210ScooH  ASDDGSLKSSSPTSYWKSLAPDRSDDEHDPLDNTSRPRYSHSYLSDSDTEAKLTETNA 118
Hu SP-R210LcooH  ASDDGSLKSSSPTSYWKSLAPDRSDDEHDPLDNTSRPRYSHSYLSDSDTEAKLTETNA 103
                  #          &    &             *  &&        *              *
```

\#: semi-conserved substitution
\*: conserved substitution
&: non-conserved substitution P4G4 (350-I2) epitopes: KYQKKKNK (SEQ ID NO:15) and VKSWLSKNK (SEQ ID NO:16) (consensus motif: KxxxxKNK; (SEQ ID NO:17))

P2H10 (350-B1) epitope: DLINSLQD (SEQ ID NO:18)

```
Ms SP-R210ScooH 1-118 is SEQ ID NO:19
Ms SP-R210LcooH 1-103 is SEQ ID NO:20
Hu SP-R210ScooH 1-118 is SEQ ID NO:21
Hu SP-R210LcooH 1-103 is SEQ ID NO:22
```

| Hybridoma original designation[1] | Cloned hybridoma designation | ELISA binding assays (values above 0.100 are considered positive)[2,3] | | | | | Western blot using (recombinant R350 protein) | Mouse receptor protein (Western blot) | Immuno-fluorescence detection (mouse cell line) | Immuno-histology for rabbit spleen tissue (acetone fixed) | Functional assay[4] |
|---|---|---|---|---|---|---|---|---|---|---|---|
| | | R350 (intact) | R300 (intact) | R350 (second screen) | R300 (intact) | R300 (denatured) | | | | | IAV Inhibition Or Immunoprecipitation (ip)[5] |
| P3.A2 | | 0.296 | 0.500 | 0.487 | 1.069 | 0.526 | + | | | | |
| P3.C4 | | 0.382 | 0.224 | 0.404 | 0.976 | 0.467 | + | | | | |
| P2.C12 | | 0.621 | 0.595 | 0.512 | 0.519 | 0.164 | - | | | | |
| P1.D1 | | 0.569 | 0.378 | 0.638 | 0.297 | 0.096 | | | | | |
| P3.D7[6] | 350.A6 | 0.179 | 0.047 | 0.550 | 0.032 | 0.032 | + | - | ++ | ++ | + |
| P2.F5[6] | 350.C3 | 1.757 | 1.783 | 1.291 | 1.566 | 1.515 | + | - | | - | + |
| P2.F8 | 350.D2 | 0.769 | 0.638 | 1.285 | 1.450 | 1.377 | - | - | | - | + |
| P3.F10 | | 0.192 | 0.229 | 0.834 | 0.429 | 0.234 | | | | | |
| P1.G2 | | 0.178 | 0.081 | 0.650 | 0.180 | 0.476 | +/- | | | | |
| P4.G4 | 350.I2 | 0.197 | 0.190 | 0.653 | 0.748 | 0.419 | ? +/- | | ++ | ++ | Conformational Epitope ip |
| P5.G9 | | 0.689 | 0.451 | 0.726 | 0.512 | 1.078 | + | - | | | |
| P3.G12 | | 0.425 | 0.415 | 0.718 | 0.561 | 0.576 | - ? | | ++ | | |
| P1.H2 | 350.K17 | 1.244 | 0.711 | 0.810 | 0.683 | 1.022 | + | | ++ | - | ip |
| P3.H4 | | 0.634 | 0.510 | 0.825 | 0.406 | 0.271 | False + | | | | |
| P3.H8 | No + clones | 0.193 | 0.245 | 0.033 | 0.368 | 0.212 | - | | ++ | | |
| P1.H9 | | 0.399 | 0.292 | 0.448 | 0.154 | 0.153 | | | | | |
| P4.H9 | | | | 0.885 | 0.889 | 0.722 | + | - | | | |
| P2.H10[6] | 350.B1 | 1.614 | 0.046 | 0.902 | 0.025 | 0.026 | + | + | | ++ | Yes |
| (blank or no hybridoma media) | | 0.045 – 0.055 | 0.040 – 0.048 | 0.032 | 0.025 | 0.030-0.034 | | | | | |
| | | | | | 0.035 | | | | | | |
| | | | | | | | | | | | |
| P6.A5 | | | 0.121 | 0.750 | 0.247 | 0.199 | - | | | | |
| P10.A5 | | | | 0.110 | 0.143 | 0.031 | | | | | |
| P7.A9 | | | 0.374 | 0.794 | 0.618 | 0.481 | +/- | False + | | | |
| P6.B8 | | | 0.110 | 1.163 | 1.192 | 0.914 | + | + | | | |
| P6.B9 | 350.E12 | | 0.539 | 0.056 | 0.149 | 0.048 | - | - | ++ | - | +/- |
| P10.B9 | | | | 1.271 | 1.638 | 1.202 | + | | | | |
| P6.C3 | | | 0.106 | 0.040 | 0.129 | 0.036 | - | | | | |
| P6.D8 | | | 0.228 | 0.041 | 0.216 | 0.104 | | | | | |
| P9.D8 | No + clones | | | 0.318 | 1.095 | 0.528 | + | + | | | |
| P6.E7 | | | 0.173 | 0.899 | 0.926 | 0.515 | | | | | |
| P6.F1 | | | 0.096 | 0.084 | 0.333 | 0.159 | | | | | |
| P8.F6 | 350.G4 | | 0.560 | 0.854 | 1.235 | 1.153 | + | + | | + | |
| P6.F8 | | | 0.365 | 0.810 | 0.835 | 0.834 | + | - | | | |
| P7.G10 | | | 0.098 | 0.889 | 0.787 | 0.479 | - | - | | | |
| P10.H1 | 350.J18 | | 0.839 | 0.699 | 0.985 | 1.071 | + | + | | ++ | |
| H2 (none) | | | 0.244 | | | | | | | | |
| P8.H3 | No + clones | | 0.182 | 0.284 | 0.315 | 0.205 | - | - | | | |
| (blank, or no hybridoma media) | | | | | 0.025 – 0.035 | 0.030-0.034 | | | | | |
| | | | | | | | | | | | |
| P7.E1 | | | | 0.068 | | | | | | | |
| P8.D2 | | | | 0.082 | | | | | | | |
| P10.E1 | | | | 0.185 | | | | | | | |
| P10.A4 | | | | 1.237 | | | | | | | |

Figure 14

Figure 30A. CDR mapping of anti-SPR210s Variable heavy chain

P2H10 (350-B1)_Heavy_chain_VH_protein (anti-SPR210s)

EVKLEESGPELVKPGASVKMSCKASGYIFSDYYMRWVKQSHGKSLEWIGDINPKNGDTFYNQKFKGK

FR1     CDR1     FR2     CDR2

ATLTVDKSSTTAYMQLNRLTSEDSAVYYCVREGDWGQGTTLTVSS     (SEQ ID NO:23)

FR3     CDR3

CDR1: GYIFSDYYMR (SEQ ID NO:3)
CDR2: DINPKNGDTFYNQKFKGK (SEQ ID NO:4)
CDR3: REGD (SEQ ID NO:5)

Figure 30B. Coding sequence of anti-SP-R210s Variable heavy chain.
The location of the CDR coding sequences are shown in bold \>Heavy_chain_VH_cDNA_P2H10 (350-B1)

gaggtaaagctggaggagtctggacctgagctgtgaagcctggggcttcagtgaagatg tcctgcaaggcttctggatacatcttctgattatatgaggtgggtgaagcagagc
                CDR1 catggaaagagcccttgagtggattggagatattaatcctaagaatggtgatact**ttctac
                                              CDR2 aaccagaagttcaagggcaaggccacattgactgtagataatcttccaccacagcctac atgcagctcaacaggctgacatctgaggactctgcagtctattattgtgta**agagagggg
                                                                CDR3 gactggggccaaggcaccactctcacagtctcctca (SEQ ID NO:24)

Figure 30C. CDR mapping of anti-SPR210$_S$ Variable light chain

P2H10 (350-B1)_Light_chain_Vk_protein (anti-SPR210$_S$)

DIVMTQSPLSLPVSLGDQASISCRSSQTILHSNGNTYLEWYLQKPGQSPKLL/YKVSKRFSGVPDRFS

FR1      CDR1      FR2      CDR2

GSGSGTDFTLKISRVEVEDLGVYYCLQGSHVPLTFGAGTKLEVK (SEQ ID NO:25)

FR3      CDR3

CDR1: RSSQTILHSNGNTYLE (SEQ ID NO:6)
CDR2: KVSKRFS (SEQ ID NO:7)
CDR3: LQGSHVPLT (SEQ ID NO:8)

Figure 30D. Coding sequence of anti-SP-R210s Variable light chain.
The location of the CDR coding sequences are shown in bold >Light_chain_Vk_cDNA_P2H10 (350-B1)
gatattgtgatgacacagtctccactctccctgcctgtcagtcttggagatcaagcctcc atctcttgcagatctagtcagatccattttacatagtaatggaaacacctattagaatgg
            CDR1 tacctgcagaaaccaggccagtctccaaagctcctgatctataaagtttccaaacgattt
                       CDR2 tctggggtcccagacaggttcagtggcagtggatcagggacagatttcactctcaagatc agcagagtggaggttgaggatctgggagtttattactgcctttcaaggttcacatgttccg
                          CDR3 ctcacgttcggtgctggggaccaagctggagaggtgaaa (SEQ ID NO:26)

Figure 30E. CDR mapping of anti-SPR210$_{S+L}$ Variable heavy chain

P4G4 (350-I2)_Heavy_chain_VH_protein (anti-SPR210$_{S+L}$)

EVKLEESGPEVVRPGVSVKISCKGSGYTFTDYAMH WVKQSHAKSLEWIGVISTYNGNTKYNQKFKDKA
　　　　　FR1　　　　　　　　　　　　　　　　　CDR1　　　　　　　　　　　FR2　　　　　　　　CDR2

TMTVDKSSTAYMELARLTSEDSAIYYCARTDYDNGDYVMDYWGQGTSVTVSS (SEQ ID NO:27)
　　　　　　　FR3　　　　　　　　　　　　　　　　CDR3

CDR1: GYTFTDYAMH (SEQ ID NO:9):
CDR2: VISTYNGNTKYNQKFKD (SEQ ID NO:10):
CDR3: ARTDYDNGDYVMDY (SEQ ID NO:11):

Figure 30F. Coding sequence of anti-SP-R210$_{S+L}$ Variable heavy chain.
The location of the CDR coding sequences are shown in bold >P4G4(350-I2)_VH_cDNA gaggtaaagctggaggagtctggggcctgaggtggtgaggcctggggtctcagtgaagatt tcctgcaagggttccggctacacattcactgattatgctatgcactgggtgaagcagagt
                                 CDR1 catgcaaagagtctagagtggattggagttattagtactacaatggtaatacaaagtac
                                                                  CDR2 aaccagaagtttaaggacaaggccacagattgactgtagacaatcctccagcacagcctat atggaacttgccagattgacatctgaggattctgccatctattactgtgcaaggacggac tatgataacggggactatgttatggactactggggtcaaggaacctcagtcaccgtctcc
                           CDR3 tca (SEQ ID NO:28)

Figure 30G.

CDR mapping of anti-SPR210$_{S+L}$ Variable light chain

P4G4 (350-I2)_Light_chain_Vk_protein (anti-SPR210$_{S+L}$)

DIVLTQSPSSMYTSLGGRVTIT*C*KASQDINNYLS*WFQ*QKPGKSPKTL*IN*RANRLVDGVPSRFSGSG
FR1 CDR1 FR2 CDR2

SGQDYSLTISSLEYEDMGIYY*C*LQYDEFPLT*FGAG*TKLELK (SEQ ID NO:29)
FR3 CDR3

CDR1: KASQDINNYLS (SEQ ID NO:12)
CDR2: RANRLVD (SEQ ID NO:13)
CDR3: LQYDEFPLT (SEQ ID NO:13)

Figure 30H.

Coding sequence of anti-SP-R210$_{S+L}$ Variable light chain

>P4G4(350-I2)_Vk_cDNA gacattgtgctgacccagtctccatctcctcatgtatacatctctaggggagagtcact atcacttgcaaggcgagtcaggacattaataactatttaagctggttccagcagaaacca

CDR1 gggaaatctcctaagaccctgatcaatgtgcaaacagattggtagatggggtccatca

CDR2 aggttcagtggcagtggatctgggcaagatattctccaccatcagcagcctggagtat gaagatatgggggatttattattgtctacaatatgatgagtttccgctcacgttcggtgct

CDR3 gggaccaagctggagctgaaa (SEQ ID NO:30)

Bold: CDR coding sequences

COMPOSITIONS AND METHODS FOR TARGETING OF THE SURFACTANT PROTEIN A RECEPTOR

CROSS REFERENCE TO RELATED APPLICATIONS

This application claims priority to U.S. patent application No. 62/024,314, filed Jul. 14, 2014, and to U.S. patent application No. 62/121,830, filed Feb. 27, 2015, the disclosures of each of which are incorporated herein.

STATEMENT REGARDING FEDERALLY SPONSORED RESEARCH

This invention was made with government support under Grant No. HL068127, awarded by the National Institutes of Health. The Government has certain rights in the invention.

FIELD

The present disclosure relates generally to compositions for prophylaxis, therapy and diagnosis of conditions that include macrophage-mediated immune responses.

BACKGROUND

Surfactant protein A (SP-A) is a crucial component of the pulmonary innate immune system in the alveolar spaces. SP-A is the major protein constituent of pulmonary surfactant; it is involved in organization of large aggregate surfactant phospholipids lining the alveolar surface and acts as an opsonin for pathogens. SP-A is incorporated in the tubular myelin fraction of pulmonary surfactant that covers the alveolar lining fluid of the distal airway epithelium. The presence of pathogen-derived molecules may trigger reorganization of surfactant lipids and exposure of SP-A to bind pathogens at points of entry on the surfactant interface. Alveolar macrophages in the aqueous hypophase may then patrol areas of disturbance on the surfactant layer binding SP-A-opsonized bacteria, and SP-A has been shown to play an important role in modulating complement receptor-mediated phagocytosis. In this regard, SP-A modulates macrophage phagocytosis and a host of pro- and anti-inflammatory responses that help in eradication of infection first and then resolution of inflammation in vivo. Several macrophage receptors have been implicated in the ability of SP-A to coordinate clearance of pathogens and apoptotic cells and temporal control of inflammation in the lungs. The SP-A receptor SP-R210 was identified as cell surface isoforms of unconventional Myo18A (Yang C. H., et al. (2005) J. Biol. Chem. 280, 34447-34457). The Myo18A gene encodes two alternatively spliced SP-R210 isoforms, SP-R210$_L$ and SP-R210$_S$. The longer 230-240-kDa SP-R210$_L$ isoform contains an amino-terminal PDZ protein interaction module that is absent from the shorter 210-kDa SP-R210$_S$. SP-R210$_S$ is highly expressed in both mature macrophages and in immature monocytic cells. However, SP-R210$_L$ is only expressed in mature macrophages. Thus, for a variety of reasons, there is a need to develop novel compositions and methods for selectively targeting/binding the distinct SP-R210 isoforms. The present disclosure meets these and other needs.

SUMMARY

The present disclosure provides compositions and methods for use in prophylaxis, therapy and diagnosis of conditions which involve surfactant protein receptors (SPR) including the SPR for surfactant proteins A (SPA). In particular, the SP-A receptor known as SP-R210 is expressed in at least two isoforms by macrophages, namely the SP-R210$_L$ and SP-R210$_S$ isoforms, the SP-R210$_L$ isoform being predominant on, for example, alveolar macrophages. The disclosure includes novel specific binding partners for the SP-R210$_L$ and SP-R210$_S$ isoforms, and methods of using such binding partners.

In one aspect, the disclosure comprises a monoclonal antibody or antigen binding fragment thereof, wherein the monoclonal antibody is produced by a hybridoma described in FIG. 14. In embodiments, the monoclonal antibody or antigen binding fragment thereof has the same specificity as a monoclonal antibody produced by a hybridoma of FIG. 14, but the monoclonal antibody or antigen binding fragment thereof is produced recombinantly. In certain embodiments, the monoclonal antibodies or antigen binding fragments of them are provided in pharmaceutical preparations.

In certain embodiments, the monoclonal antibodies and/or fragments thereof are produced by the hybridoma termed P2H10, or the hybridoma termed P4G4 as shown in FIG. 14, or are produced recombinantly and have the same amino acid sequences, or the same CDR sequences, of the mAbs produced by the hybridoma termed P2H10, or the hybridoma termed P4G4 as shown in FIG. 14. In embodiments, the mAbs or fragments thereof comprise or consist of an amino acid sequence or fragment thereof shown in FIG. 30A, FIG. 30C, FIG. 30E, FIG. 30G, and combinations thereof. Non-limiting examples of DNA sequences encoding such mAbs and fragments are illustrated in FIGS. 30B, 30D, 30F and 30H, respectively.

In certain aspects, the antigen binding fragments of the monoclonal antibodies described in this disclosure include but are not necessarily limited to Fab fragments, Fab' fragments, F(ab')$_2$ fragments, Fd fragments, Fv fragments, scFv fragments, and combinations thereof. In certain embodiments, the monoclonal antibodies or antigen binding fragments thereof can be provided as components of a fusion protein.

In another aspect the disclosure includes methods for prophylaxis and/or therapy for an individual in need thereof comprising administering to the individual an effective amount of monoclonal antibody or antigen binding fragment thereof, as further described herein. In certain embodiments, the individual to whom a composition comprising such antibodies or antigen binding fragments is administered is in need of a condition selected from a bacterial infection, a viral infection, or any other condition wherein undesirable inflammation is present. In embodiments, the individual has a viral pneumonia. In embodiments, the individual is in need of treatment for viral influenza.

In one aspect the disclosure includes a method for inhibiting binding of a pathogenic microorganism to macrophages in an individual comprising introducing into the individual a pharmaceutical composition described herein. In embodiments, the administration prevents or inhibits a signaling cascade that would be initiated at least in part said binding of the pathogenic microorganism to the macrophages.

In another aspect the disclosure includes a method of making a monoclonal antibody comprising isolating the monoclonal antibody from a culture media that comprises a hybridoma described further herein.

In another aspect the disclosure includes a method of making a monoclonal antibody or antigen binding fragment thereof comprising introducing an expression vector encoding the monoclonal antibody or antigen binding fragment thereof into a cell culture, allowing expression of the monoclonal antibody or antigen binding fragment thereof, and isolating the monoclonal antibody or antigen binding fragment thereof from the cell culture.

Expression vectors encoding a monoclonal antibody or antigen binding fragment thereof, as well as cell cultures comprising such expression vectors, are also included within the scope of this disclosure.

All polynucleotides encoding the mAbs and Ag binding fragments thereof are included in this disclosure, as are methods of making such antibodies.

In another aspect the present disclosure includes a method for inhibiting binding of a pathogenic microorganism to a population of macrophages in an individual comprising introducing into the individual a pharmaceutical composition of this disclosure.

In another aspect the present disclosure includes a method of making a monoclonal antibody or antigen binding fragment thereof comprising introducing an expression vector encoding the monoclonal antibody or antigen binding fragment thereof into a cell culture, allowing expression of the monoclonal antibody or antigen binding fragment thereof, and isolating the monoclonal antibody or antigen binding fragment thereof from the cell culture.

In another aspect the present disclosure includes SP-R210 modulation such that an increase expression of one or more innate receptors is induced in at least one type of cell, such as in immune cells. In non-limiting embodiments, a 2-20-fold increased expression of several innate receptors at both protein (TLR-2, CD11c, CD36, and CD14) and transcriptional (SR-A, CD11b) levels can be achieved by disrupting expression/function of SP-R210$_L$.

In various aspects the disclosure also includes modulating responsiveness of macrophages to certain agents, including but not necessarily limited to LPS, by modulating SP-R210$_L$.

In various aspects the disclosure also includes activation of TLR4 signaling in macrophages, and can further comprise modulating CD14 and TLR-4 internalization, by modulating SP-R210$_L$.

In embodiments, the disclosure generally comprises targeting the SP-R210$_S$ to facilitate resolution of influenza pneumonia. The disclosure includes enhancing T-cell mediated immunity, such cell-mediated immune reactions to influenza by modulating effector T lymphocytes. In embodiments, the disclosure comprises imparting cross-protective immunity against a plurality of influenza A virus strains.

BRIEF DESCRIPTION OF FIGURES

FIG. 1 provides a graphical depiction of the domain organization of the SP-A SP-R210 receptor and its two isoforms SP-R210$_L$ and SP-R210$_S$ . The inset on FIG. 1 demonstrates that SP-R210 is expressed on the surface of macrophages as determined by flow cytometry. Cells were incubated with non-specific control IgG and an antibody that binds the carboxy-terminal domain of SP-R210, termed anti-SP-R210 IgG. The cells were subsequently interrogated with secondary fluorescent anti-IgG antibodies to determine level of binding of the primary IgGs. The red trace reports the level as fluorescent intensity of SP-R210 on the x-axis which is clearly separated from the blue trace for the background control IgG. Therefore, SP-R210 is present on the cell-membrane with access to the external environment of the cell.

FIG. 2. Protein sequence alignment epitope location of mouse (Ms) and human (Hu) SP-R210 carboxy-terminal (cooh) domains of SP-R210S and SP-R210L. Epitopes recognized by a monoclonal antibody produced by the hybridoma termed P4G4 comprise KYQKKKNK (SEQ ID NO:15) and VKSWLSKNK (SEQ ID NO:16) are shown in bold an italics, yielding a consensus motif of KxxxxKNK (SEQ ID NO:17). An epitope recognized by a monoclonal antibody produced by the hybridoma termed P2H10 which is also described further below and comprises DLINSLQD (SEQ ID NO:18) shown in bold. Notably, the KYQKKKNK (SEQ ID NO:15) and DLINSLQD (SEQ ID NO:18) epitopes encompass a 15 amino-acid insertion unique to SP-R210$_S$ as described further below.

FIG. 3 provides a graphical depiction of a cloning procedure for generating a conditional disruption of SP-R210 in MΦ in transgenic mice. Ms SP-R210$_S$cooh (SEQ ID NO:19); Ms SP-R210$_L$cooh (SEQ ID NO:20); Hu SP-R210$_S$cooh (SEQ ID NO:21); Hu SP-R210$_L$cooh (SEQ ID NO:22).

FIG. 4 provides a photographic and graphical representation of data demonstrating that a lack of SP-R210$_L$ blocks infection of influenza A virus (IAV) in MΦ.

FIG. 5 provides data demonstrating that a lack of SP-R210$_L$ does not affect binding and internalization of IAV, but the endocytic trafficking of NP to nucleus is blocked when SP-R210$_L$ is absent.

FIG. 6 provides a graphical depiction of data demonstrating that SP-R210L -mediated IAV infection of MΦ is coupled to the TNFα production.

FIG. 7 provides graphical depictions of data demonstrating that SP-R210$_L$-deficient MΦ and AMs are hyper-responsive to the TLR7 ligands.

FIG. 8 provides graphical and photographic representation of data showing that IAV infection results in inhibition of SP-R210L expression in a time-dependent manner FIG. 9 provides graphical and immunohistochemical data demonstrating that SP-R210L-deficient mice are significantly more susceptible to IAV infection.

FIG. 10 provides microscopy images demonstrating SR-R210 isoform-mediated binding and internalization in macrophages.

FIG. 11 provides graphical data showing that disruption of SP-R210 in alveolar macrophages (AM) delays replication of IAV in vivo.

FIG. 12 provides flow cytometry and graphical data showing antibodies to SP-R210 inhibit IAV infection.

FIG. 13 provides flow cytometry data demonstrating that desialylated (DS) SP-A blocks infection of macrophages with IAV. Thus, SP-A competitively inhibits binding of the influenza virus to the receptor.

FIG. 14 provides a Table summarizing hybridomas that were generated by immunizing mice with r350 protein and screening against r350 and r300 proteins (r=recombinant; the 350 and 300 proteins are as depicted in FIG. 1). The Table provides [1]ELISA data for: Screen of fusion (hybridomas) for putative positives. [2]R350=U18AC2; R300=U18AC2. [3]Antibodies were tested against intact and denatured antigen to screen conformation versus linear epitope antibodies; [4]Antibodies that inhibit binding of influenza A virus to macrophages; [5]Antibodies that recognize the native protein by immunoprecipitation are indicated as ip; [6] Mouse monoclonal antibodies were prepared using standard procedures. BALB/c mice were immunized using purified recombinant murine SP-R210$_{CL}$ (R350) protein in RIBI adjuvant. Immunizations were delivered both subcutaneously and intra-peritoneally in volumes of 0.05 ml per site per mouse per immunization. Immunizations were given bi-weekly 3 times, the final booster immunization was given as protein in saline. Three days after the final booster immunization, the mice were anesthetized using ketamine/xylazine and spleen and lymph nodes removed following exsanguination. Single cell suspensions of immune cells were prepared and fused with P3X63-Ag8.653 myeloma cells for the production of hybridomas. Supernatants from cultures of hybridomas were screened by ELISA for reactivity to SP-R210$_{CL}$ and SP-R210$_{CS}$ (R300) and positive cultures isolated for expansion and cloning. Positive clones producing reactive antibodies in ELISA were adapted to serum free conditions using Sigma EX-CELL 610HSF serum-free culture media for large scale production of monoclonal antibodies.

Figure 15:
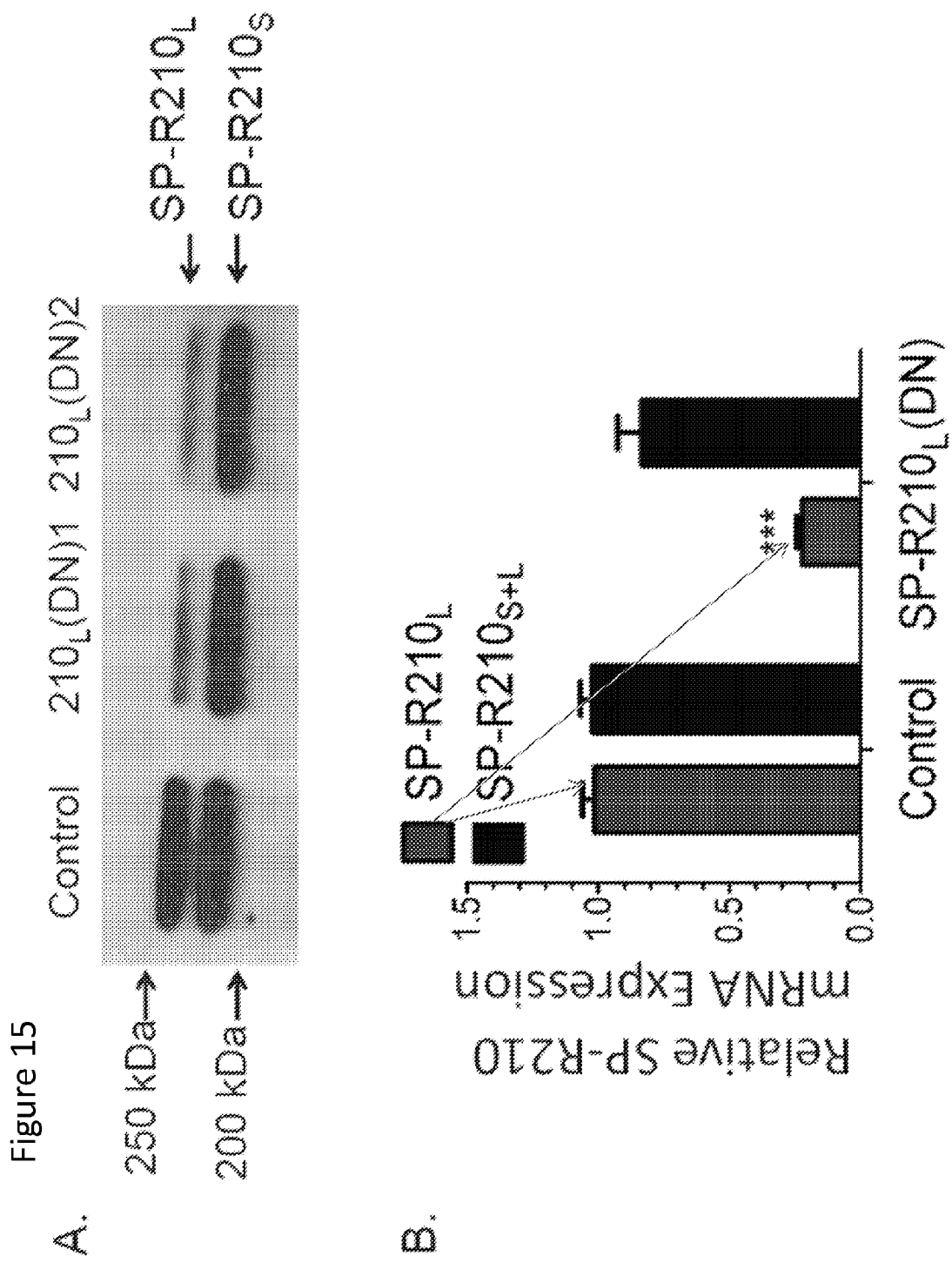

FIG. 15. Dominant-negative disruption of SP-R210L. Raw264.7 cells were stably transfected with empty pTriex-Neo2 control or vector containing the 300 (SP-R210$_L$(DN1)) and 350 (SP-R210$_L$(DN2)) bp cDNA of SP-R210 carboxy-terminal isoforms (6). A) Detergent extracts were analyzed by Western blotting using affinity purified polyclonal antibodies recognizing both SP-R210$_L$ and SP-R210$_S$. Lanes were loaded with 5 µg of protein. B) Total RNA from indicated cell lines was reverse transcribed and quantitated by qPCR using TaqMan assays and primers encompassing the SP-R210L-specific exons 1 and 2 (red bars) and internal primers encompassing exon 17 and 18 common to both SP-R210 isoforms (black bars) and 18S rRNA as internal control. (n=4 ***p<0.001).

Figure 16:
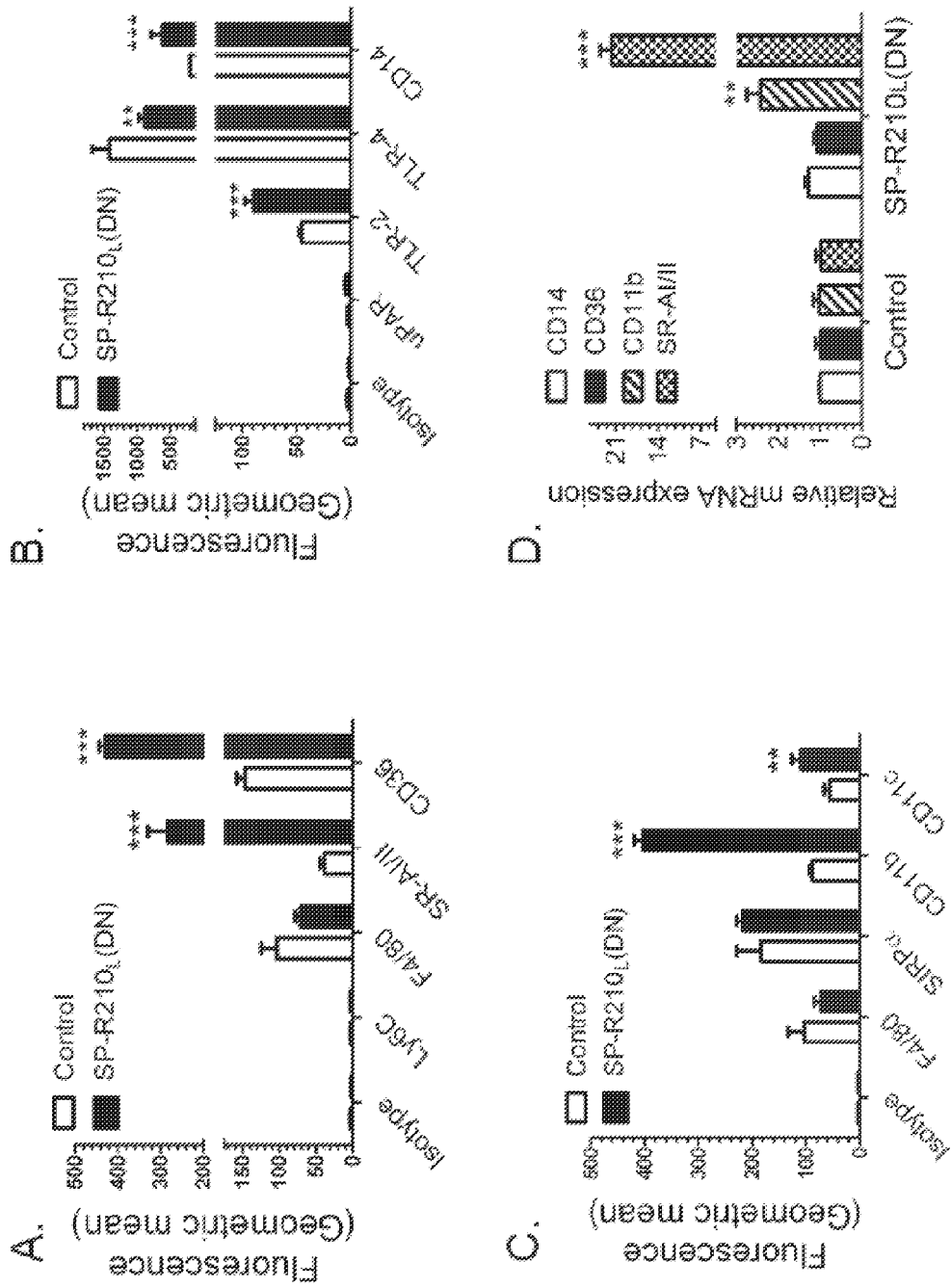

FIG. 16. Depletion of SP-R210$_L$ differentially enhances expression of innate receptors in macrophages. Control and SP-R210$_L$(DN) cells were analyzed by flow cytometry using indicated APC (A) or PE-conjugated antibodies (B, C) (n=4-8). (D) mRNA levels of indicated receptors in SP-R210$_L$(DN) cells relative to control cells were determined by qRT-PCR (n=4 independent experiments performed in duplicate, p<0.02, *p<0.005).

Figure 17:
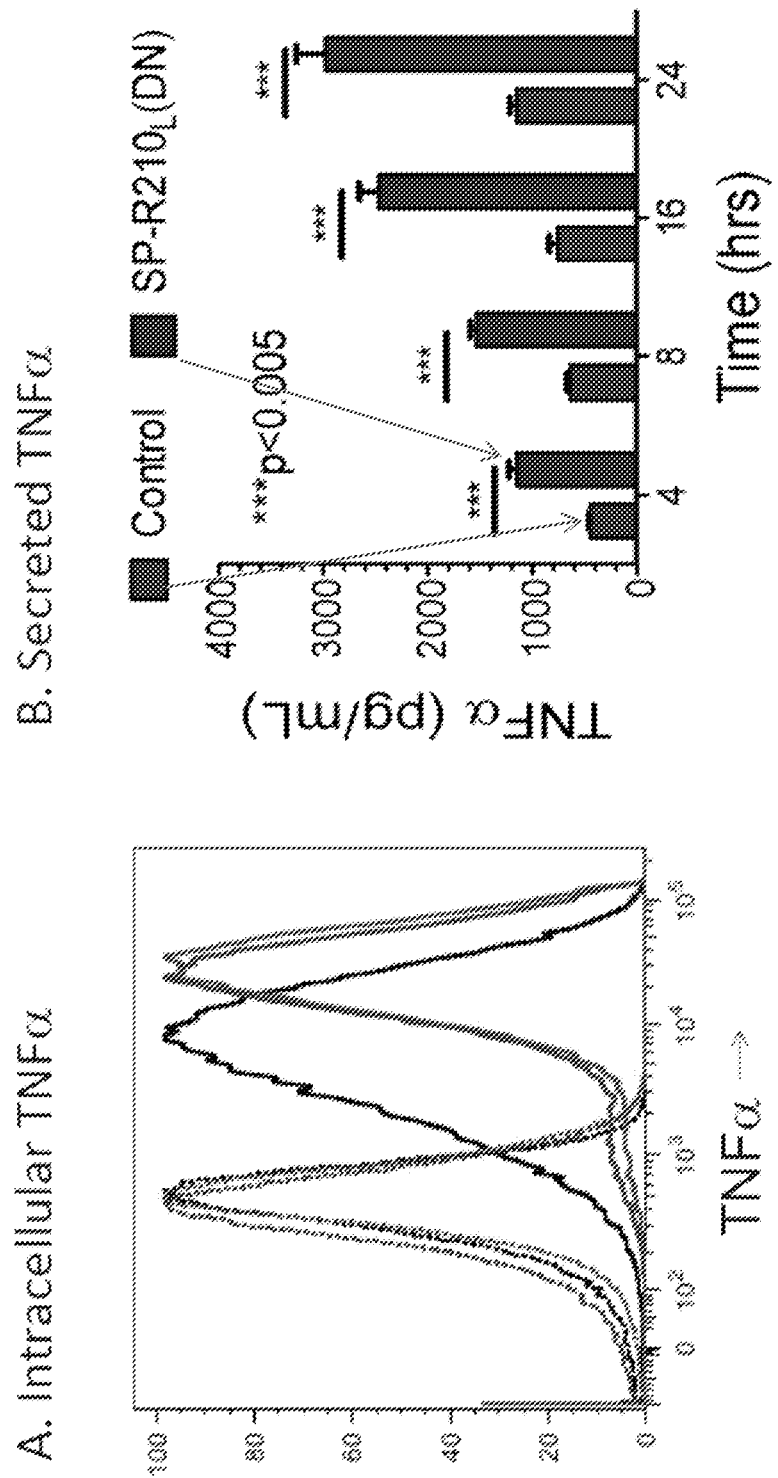

FIG. 17. Increased responsiveness of SP-R210$_L$(DN) cells to LPS. Control and SPR210L(DN) cells were plated in 12-well tissue culture dishes at a density of 150,000 cells/well and cultured 24 hrs in RPMI/10% FBS. Cells were then treated with 100 ng/mL LPS for 2, 4, 8, 16, and 24 hrs. A) Intracellular staining of TNFα was performed in brefeldin A blocked cells 2 hrs after treatment with LPS. Dotted histograms show untreated cells. Black, red, and blue histograms show intracellular TNFα staining of control, SP-R210$_L$(DN) 1, and SP-R210$_L$(DN)2 cells. B) The levels of secreted TNFα were measured by ELISA in media at indicated time points after treatment with LPS. (n=6; ***p<0.005).

Figure 18:
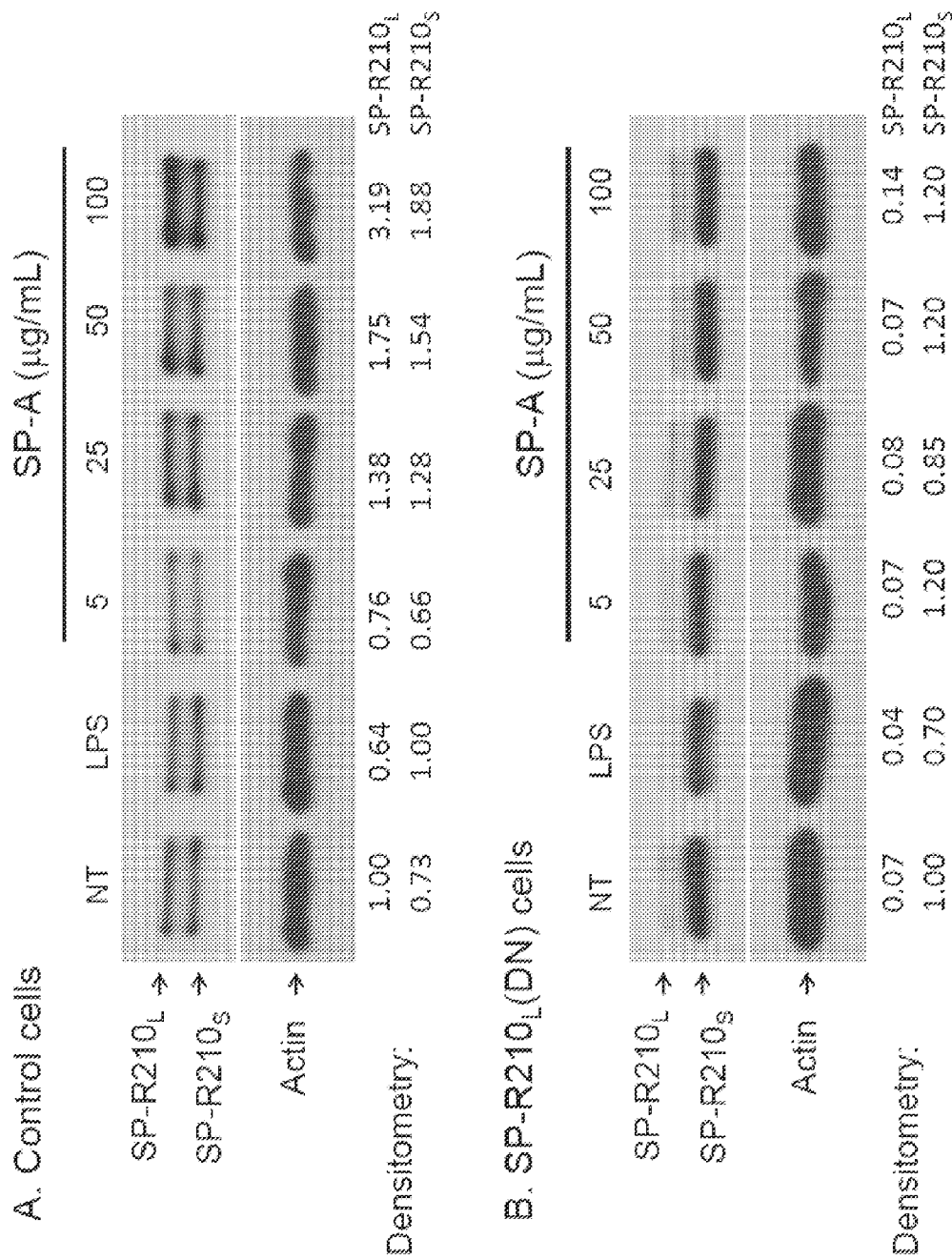

FIG. 18. SP-A induces expression of SP-R210. Expression of SP-R210 was determined by Western blot analysis in control (A) and SP-R210$_L$(DN) (B) cells treated with increasing concentration of SP-A purified by method 1. The cells were also treated with 100 ng/mL LPS. Blots were re-probed with actin as loading control. Control (A) and SP-R210$_L$(DN) (B) cells were cultured in 12 well dishes for 24 hrs and then treated with increasing concentration of SP-A, or 100 ng/mL LPS. The band intensity of SP-R210$_L$, SP-R210$_S$, and actin was determined by densitometry. Densitometry data were normalized to actin and expressed relative to SP-R210L in untreated (NT) control cells (A) and SP-R210S in SP-R210$_L$(DN) (B) cells.

Figure 19:
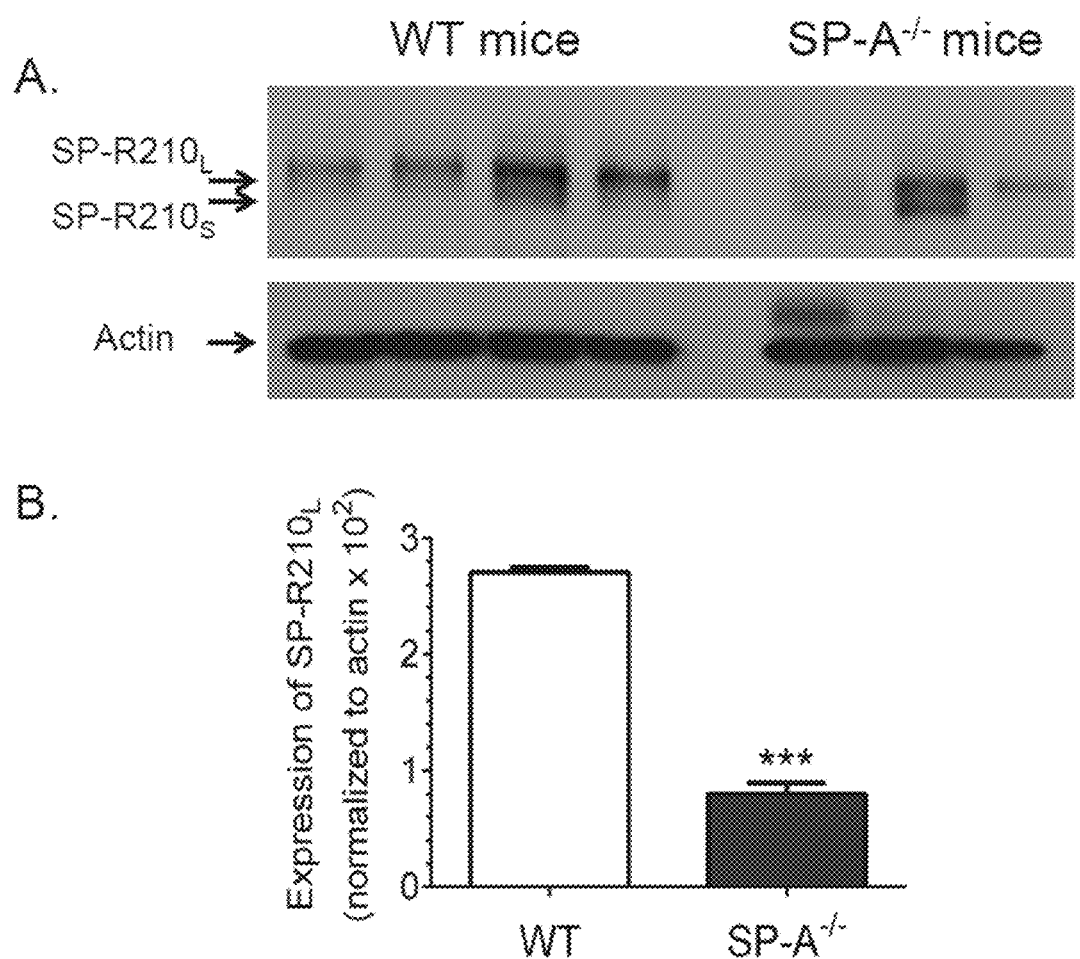

FIG. 19. SP-A enhances expression of SP-R210$_L$ in alveolar macrophages in vivo. Alveolar macrophages were isolated by lung lavage and processed for Western blot (A) and densitometry analysis (B) using polyclonal anti-SP-R210 antibodies. ***p<0.001, n=8 WT mice and n=6 SR-=A-/-mice from two independent experiments.

Figure 20:
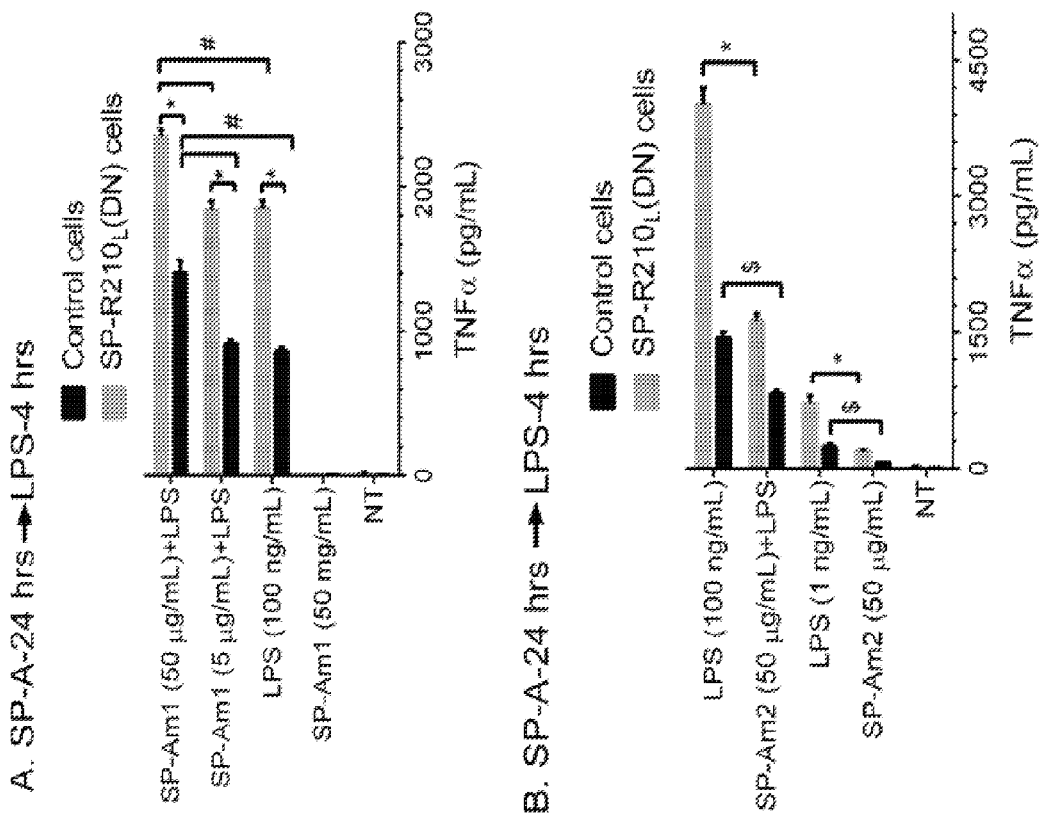

FIG. 20. SP-A and SP-R210L modulate responsiveness of macrophages to LPS. Control and SP-R210$_L$(DN) cells were pretreated with SP-A from APF-1 (FIG. 27) purified by either method 1 (SP-Am1) or method 2 (SP-Am2) as described herein. Cells were pretreated with indicated amounts of SP-Am1 (A) or SP-Am2(B) for 24 hrs and then incubated with 100 ng/mL LPS. Levels of secreted TNFα were measured in media by ELISA at 4 hrs after addition of LPS. Data shown are means±SD, n=3 representative of 3-6 independent experiments. Lines indicate significant differences between indicated groups at *p<0.0001; #p<0.04; $p<0.005

Figure 21:
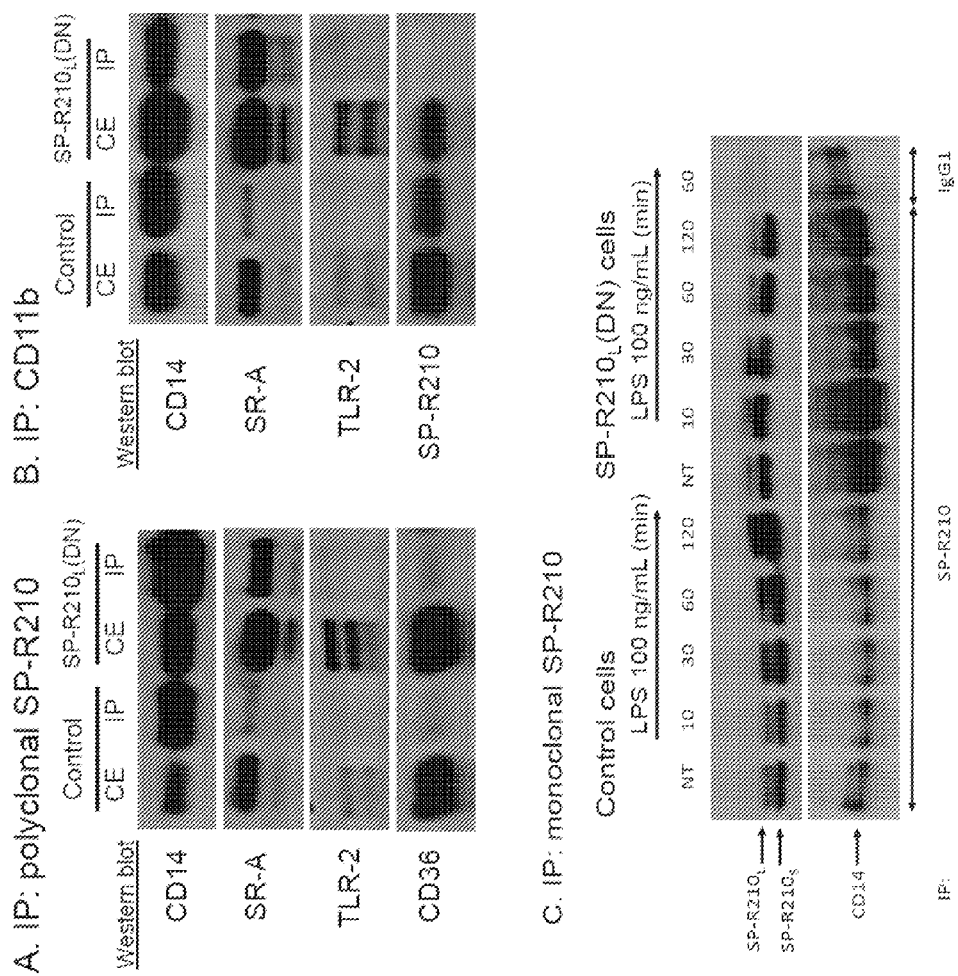

FIG. 21. Interaction of SP-R210 with innate receptors. Immunoprecipitation experiments were carried out using 10 mg/mL (A and B) or 2.5 mg/mL (C) cell extracts from control and SP-R210$_L$(DN) macrophages with polyclonal anti-SP-R210 (A), monoclonal CD11b (B), To assess the effect of LPS treatment, immunoprecipitation reactions were carried out 10, 30, 60, and 120 min after treatment with 100 ng/mL LPS (C). Co-precipitated proteins were separated on SDS-PAGE gels and blotted with indicated antibodies. Extracts immunoprecipitated with monoclonal anti-SP-R210 were re-probed with polyclonal SP-R210 antibodies. A monoclonal IgG1 against an unrelated viral antigen served as control (C). Results shown are representative of 2-4 independent experiments.

Figure 22:
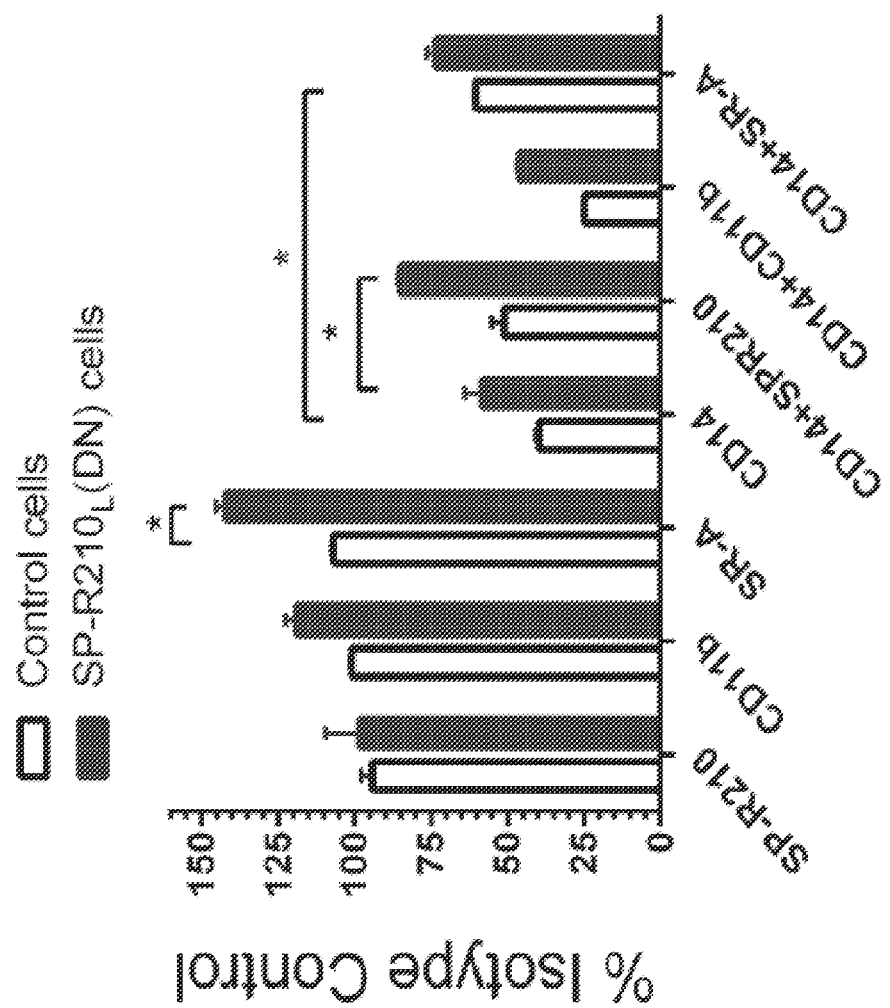

FIG. 22. Effect of neutralization antibodies on the inflammatory response to LPS. Control and SP-R210 $_L$ (DN) macrophages were pretreated for 30 min with 20 µg/mL of indicated individual or antibody combinations or respective isotype controls followed by stimulation with 100 ng/mL of LPS for 4 hrs. Cells were then harvested and processed intracellular cytokine staining with TNFα antibodies. Stained cells were analyzed by flow cytometry. The mean fluorescence of positively stained cells was expressed as percent of isotype control treated cells. Data shown are expressed means±SD and are pooled from 2-4 independent experiments performed in triplicate. *p<0.04.

Figure 23:
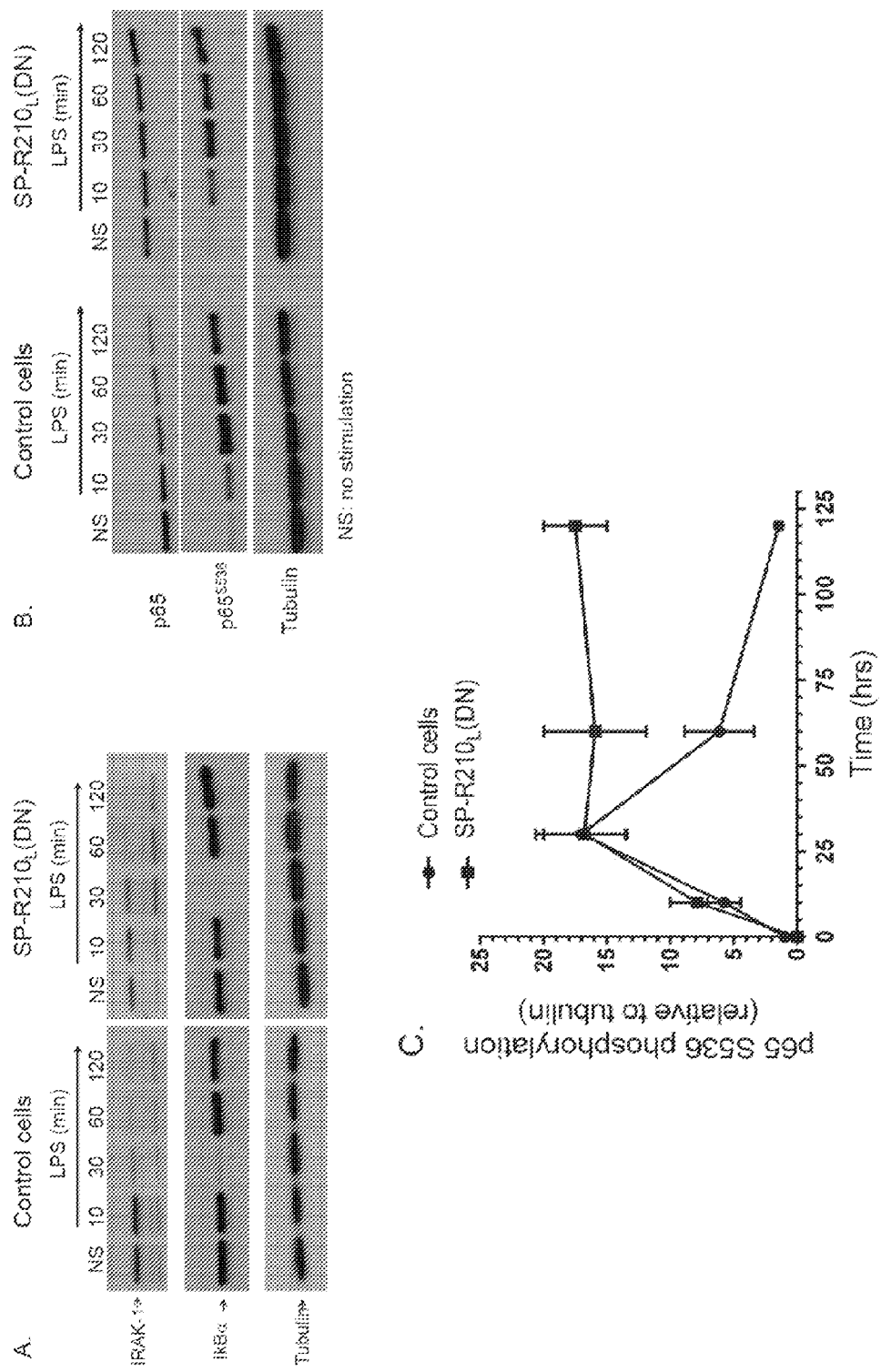

FIG. 23. Activation of TLR4 signaling in control and SP-R210 $_L$ (DN) cells. Macrophages were stimulated with 100 ng/mL LPS for indicated time points. Non-stimulated (NS) and stimulated cells were harvested and processed for Western blot analysis. Blots were probed for with IRAK-1 antibodies (A) or NFκB p65 (B), stripped, and the re-probed with IkB or phosphorylated p65, respectively. Blots were re-probed with tubulin as loading control. Densitometry analysis compared the levels of phosphorylated p65 relative to tubulin (C) Data shown are means±SD, n=4 independent experiments. *p<0.05

Figure 24:
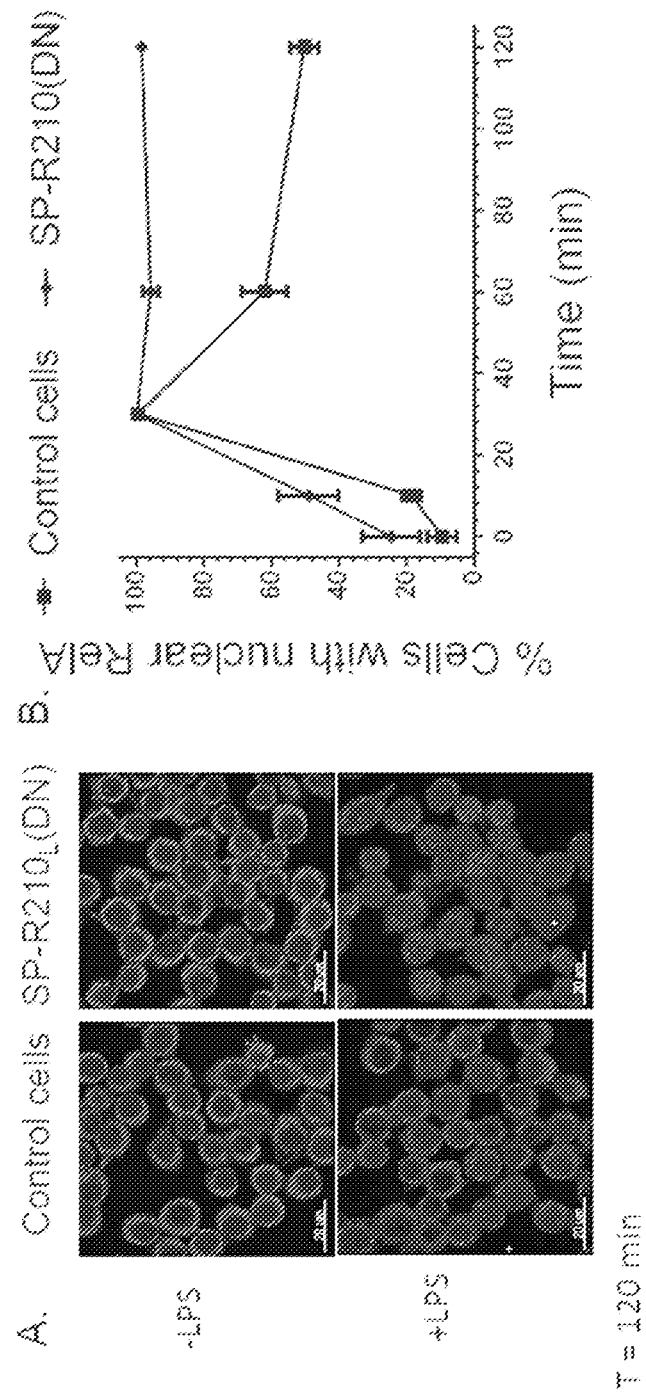

FIG. 24. Nuclear translocation of NFκB in control and SP-R210$_L$(DN) cells. Macrophages were grown on glass coverslips for 24 hrs, and then stimulated with 100 ng/mL LPS. Stimulated cells were then processed for immunofluorescent staining with anti-p65 NFκB at indicated time points after LPS treatment. The nuclear localization of NFκB was visualized by confocal microscopy (A). The percentage of cells containing nuclear p65 was quantitated in 10 random microscopic fields at 100 × magnification (B). Data shown are means±SD, n=4 independent experiments. **p<0.01.

Figure 25:
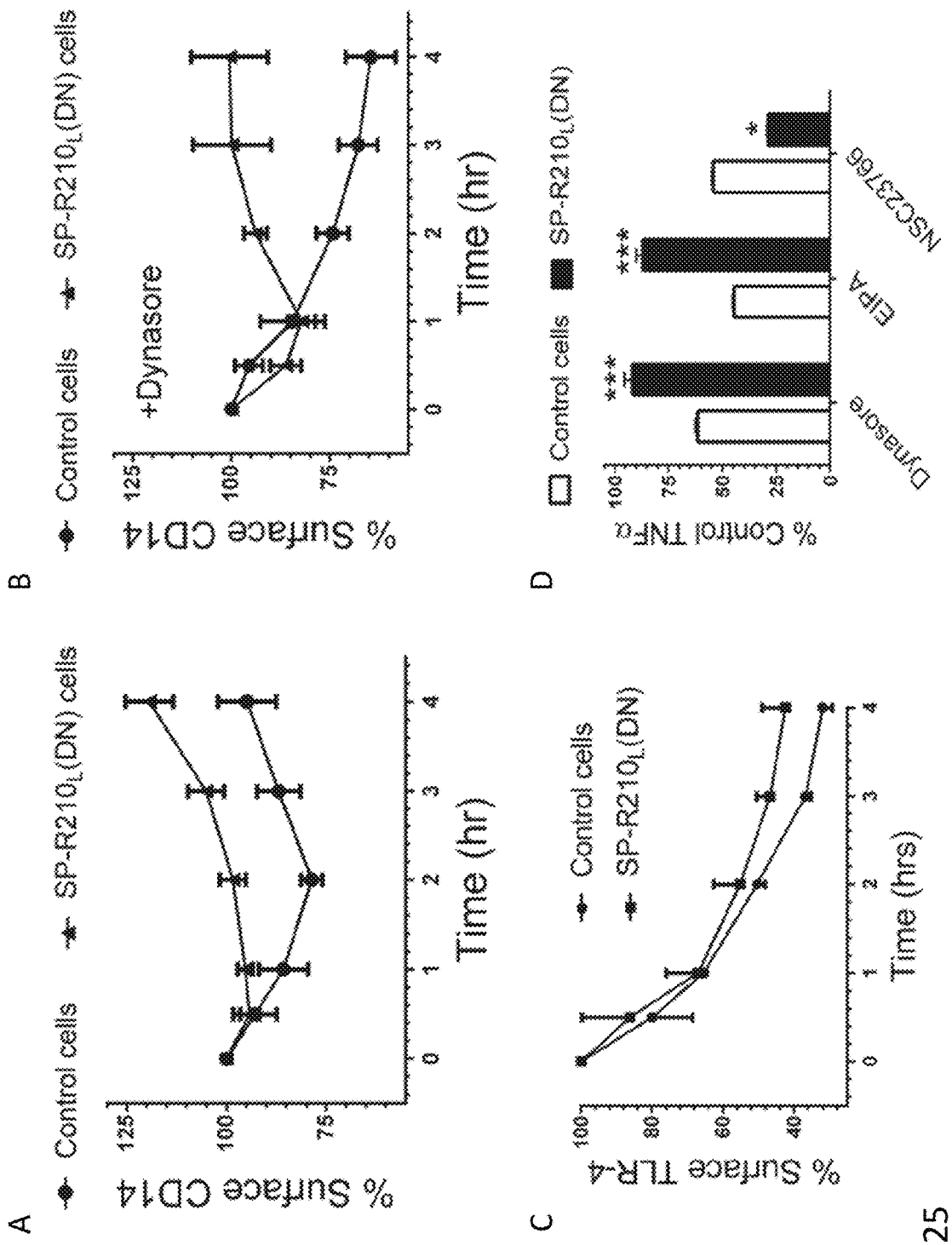

FIG. 25. Effect of SP-R210L disruption on CD14 and TLR-4 internalization and signaling. Macrophages cultured for 24 hrs on 12 well dishes were simulated with 100 ng/mL LPS for indicated time points. The cells were then harvested at indicated time points using non-enzymatic cell displacement medium and stained with antibodies to CD14 (A and B) or TLR-4 (C). The effect of dynasore on internalization of CD14 (B) and of dynasore, EIPA, and NSC23766 on TNFα synthesis (D) was assessed by addition of inhibitors 30 min before addition of LPS. Harvested cells were analyzed by flow cytometry and mean fluorescence was expressed as % of control compared to non-stimulated control or SP-R210$_L$(DN) cells (t=0) (A-C) or as percent of control TNFα in SP-R210$_L$(DN) cells compared to control cells (D). Data shown are means±SD, n=2-4 independent experiments performed in triplicate. ***p<0.01, *p<0.04.

Figure 26:
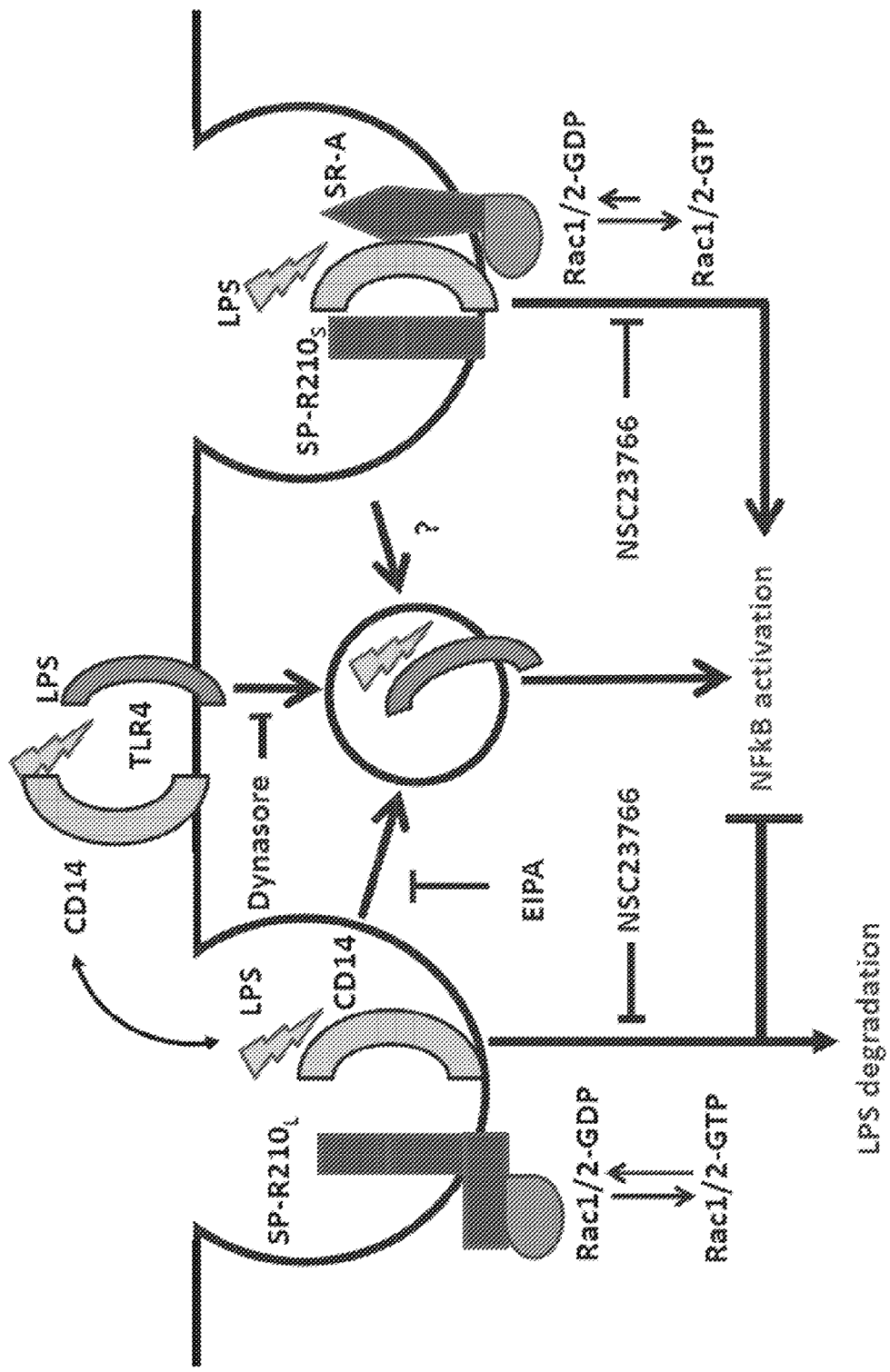

FIG. 26. Proposed interaction of SP-R210 isoforms with CD14 and SR-A in macrophage activation. SP-R210L mediates macropinocytosis of LPS-CD14 through interaction with rac 1 resulting in endosomal LPS delivery to TLR-4 and downstream activation of NFκB. Subsequent degradation of LPS results in of NFκB signaling. SP-R210L-mediated macropinocytosis and signaling is sensitive to both EIPA and NSC23766. TLR-4 signaling from the cell-surface is sensitive to dynasore. Inhibition of SP-R210$_L$ expression results in formation of the SP-R210$_S$-CD14-SR-A complex. Binding of LPS results in macropinocytosis-like internalization of the SP-R210$_S$-CD14-SR-A complex and activation of a feed-forward inflammatory pathway that depends on activation of rac 1 by SR-A. The SP-R210$_S$-CD14-SR-A pathway is sensitive to NSC23766 but not EIPA.

Figure 27:
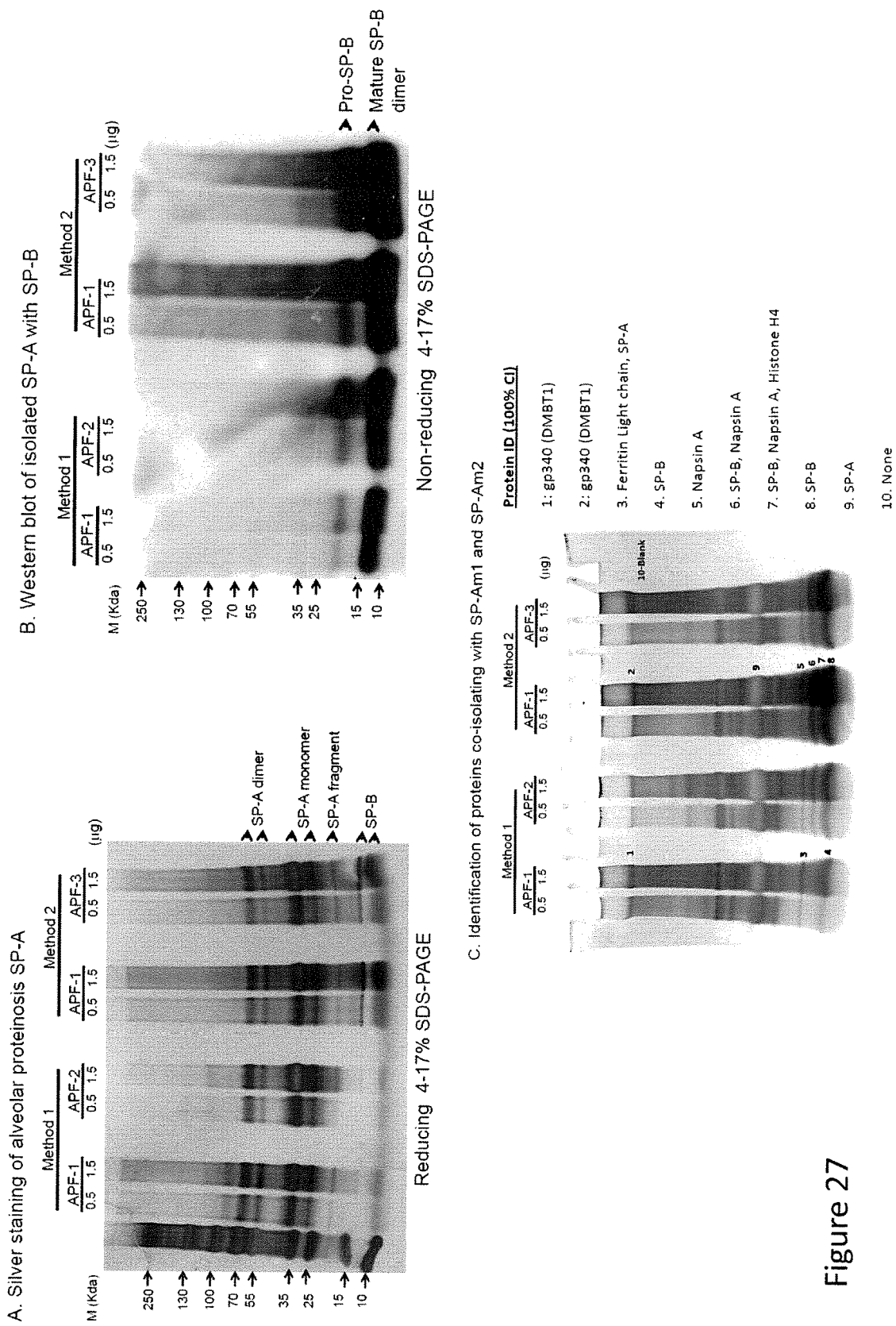

FIG. 27. SP-B co-isolates with SP-A. (A). SP-A was purified from alveolar proteinosis fluid (APF) obtained by therapeutic lung lavage from different alveolar proteinosis patients using methods 1 and 2 as described in Materials and Methods. The purity of SP-A was assessed by silver staining. Co-isolating low molecular weight bands were trypsin digested and identified as SP-B by mass spectrometry (not shown). (B). The presence of SP-B was verified by Western blot analysis. Proteins were separated on reducing (FIG. 27A) or non-reducing (FIG. 27B) 4-17% SDS-PAGE gels. SP-A purified by both methods were free of SP-D (not shown). All experiments in the present study were performed using SP-A purified from APF-1. Arrows indicate positions of SP-B and SP-A. (C) Gel showing identification of proteins co-isolating with SP-Am1 and SP-Am2.

FIG. 28A. Monoclonal SP-R210 antibodies enhance recovery from influenza pneumonia. Mice were injected intraperitoneally with 100 µg of antibodies or 100 µl PBS vehicle 24 hrs before infection with 3LD50 of Influenza virus H1N1 PR8. Mouse morbidity and weight were monitored daily. IgG1: isotype control antibody; P2H10: anti-SP-R210$_S$ antibody; P4G4: anti-SP-R210$_{L+S}$ antibody. N=5 mice per group. FIG. 28B. Monoclonal SP-R210 antibodies enhance survival from lethal for influenza infection. Mice were injected intraperitoneally with 100 µg of antibodies or 100 µl PBS vehicle 24 hrs before infection with 1000 ffc of influenza virus H1N1 PR8. Mouse morbidity and weight were monitored daily. IgG1: isotype control antibody; P2H10: anti-SP-R210$_S$ antibody; P4G4: anti-SP-R210$_{L+S}$ antibody. N=5 mice per group. *p<0.04

Figure 29:
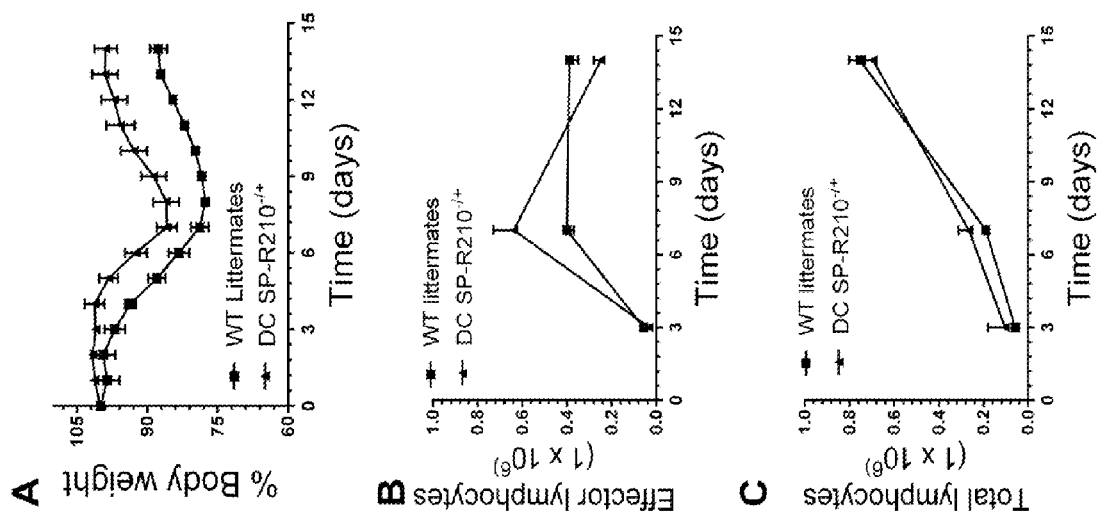

FIG. 29. Deletion of SP-R210 in CD103+ dendritic cells enhances recovery from IAV infection and recruitment of effector T lymphocytes. Mice carrying a floxed SP-R210 knockin allele were crossed with Clec9A-Cre mice to disrupt SP-R210 in CD103+DCs. WT littermate controls and DC SP-R210-deficient mice were infected with a sub-lethal dose of 0.75 LD50 of IAV PR8 intranasally. (A) Body weight was monitored over time for 14 days. N=4-12 mice per group per time point. At 3, 7 and 14 days after infection 4 mice from each group were used to obtain lung lavage. The number of effector T lymphocytes (B) and total number of lymphocytes (C) was determined by flow cytometry. Data shown in A-C are means±SEM.

FIG. 30A. CDR mapping of anti-SPR210$_S$ variable heavy chain produced by hybridoma P2H10. FIG. 30B. Coding sequence of anti-SP-R210$_S$ variable heavy chain produced by hybridoma P2H10. The locations of the CDR coding sequences are shown in bold. FIG. 30C. CDR mapping of anti-SPR210$_S$ variable light chain produced by hybridoma P2H10. FIG. 30D. Coding sequence of anti-SP-R210$_S$ variable light chain produced by hybridoma P2H10. The locations of the CDR coding sequences are shown in bold. FIG. 30E. CDR mapping of anti-SPR210$_{S+L}$ variable heavy chain produced by hybridoma P4G4. FIG. 30F. Coding sequence of anti-SP-R210$_{S+L}$ variable heavy chain produced by hybridoma P4G4. The locations of the CDR coding sequences are shown in bold. FIG. 30G. CDR mapping of anti-SPR210$_{S+L}$ variable light chain produced by hybridoma P4G4. FIG. 30H. Coding sequence of anti-SP-R210$_{S+L}$ Variable light chain produced by hybridoma P4G4. The locations of the CDR coding sequences are shown in bold.

DETAILED DESCRIPTION

The present disclosure provides compositions and methods for use in prophylaxis, therapy and diagnosis of conditions which involve microbiological pathogens and the immune cells which participate in the innate immune response directed toward them. The disclosure includes methods for modulating the innate immune response, and in particular inflammatory pathways, which are known to be at least in part facilitated by macrophages. In embodiments, the disclosure includes methods for modulating cell mediated responses. In embodiments, modulating an immune response comprises stimulating an immune response, or inhibiting an immune response. In one embodiment, inhibiting an immune response comprises inhibiting inflammation and/or an inflammatory pathway.

Figure 28:
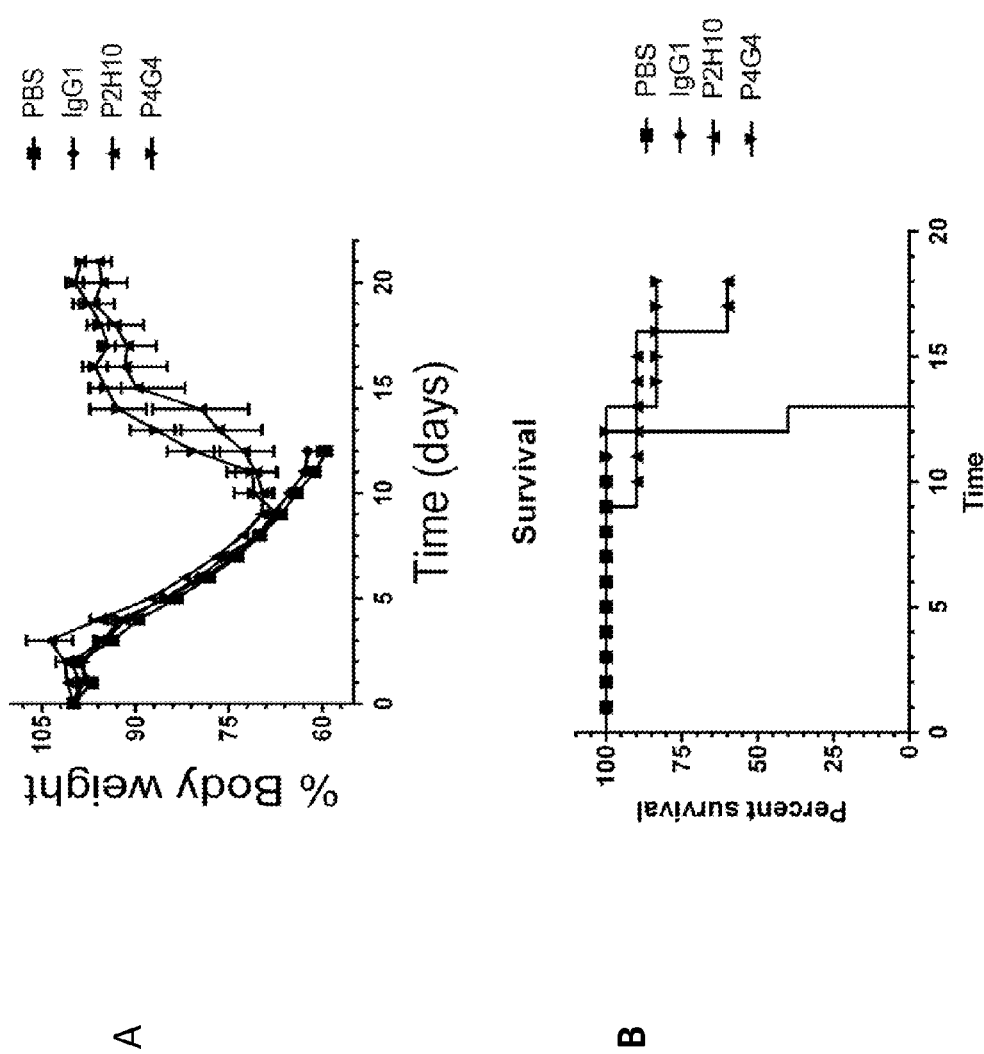

Macrophages are also referred to from time to time in this disclosure as "MΦ." Macrophages express surfactant protein receptors such as receptors for surfactant proteins A (SPA) and D (SPD). These receptors are a primary line of defense against, for example, bacterial and viral infections, which include but are not in any way limited to infections by such pathogens as *Staphylococcus aureus* and influenza virus. In particular, the SP-A receptor known as SP-R210 mediates clearance of SP-A-opsonized pathogens. As briefly discussed above, MΦ express at least two SP-R210 variants, SP-R210$_L$ and SP-R210$_S$. SP-R210$_L$ is predominant on, for example, alveolar macrophage (AM). The present disclosure demonstrates, among other findings, the role of SP-R210$_L$ in influenza A virus (IAV) infection, and that antibodies directed to SP-R210 inhibit IAV internalization of macrophages. Moreover, and as demonstrated further below the present disclosure demonstrates that antibodies that recognize SP-R210 with specificity to the SP-R210$_S$ isoform enhance recovery from influenza pneumonia and can even protect against lethal influenza challenge. For example, to obtain the data presented in FIG. 28, mice were injected intraperitoneally with 100 µg of antibodies or 100 µl PBS vehicle 24 hrs before infection with 0.75 LD50 of influenza virus H1N1 PR8. As shown in FIG. 28A monoclonal anti-SP-R210 antibodies enhance recovery for influenza pneumonia. Further, as shown in FIG. 28B, monoclonal anti-SP-R210 antibodies enhance survival after challenge with otherwise lethal influenza infection. This is consistent with data shown in FIG. 29, which demonstrates that deletion of SP-R210 in CD103+dendritic cells enhances recovery from IAV infection and recruitment of effector T lymphocytes. Thus, the present disclosure demonstrates numerous beneficial effects that are achieved by targeting the SP-R210$_S$ isoform, including but not necessarily limited to resolution of influenza pneumonia, and that targeting the SP-R210$_S$ isoform in dendritic cells enhances T-cell mediated immunity as indicated by induction and rapid contraction of effector T lymphocytes. Moreover these data suggest that enhanced T-cell mediated immunity through targeting SP-R210$_S$ results in broad cross-protective immunity to all influenza A virus strains.

With respect to the two SP-R210 isoforms, graphical depiction of the domain organization is provided in FIG. 1. FIG. 1 includes annotation of U18AC1 (SP-R210$_L$) and U18AC2 (SP-R210$_S$) wherein the U18AC2 region has a unique 15 amino acid insert that is believed to define the S form in macrophages.

The murine U18AC1 amino acid context, which does not contain the 15 amino acid insert, is: EDEMESDENEDLINSEGDSDVDSELEDRVDGVK-SWLSKNKGPSKAPSDDGSLKSSSPTSHWKPLAP-DPSD DEHDPVDSIFRPRFSHSYLSDSDTEAKLTETSA (SEQ ID NO:1). This amino acid sequence is also referred to herein as "R300." This sequence is available under GenBank accession number AAV80767.1 for SP-R210 alpha subunit splice variant CS. The "CS" and "CL" denote two variants of the SP-R210 carboxy-terminal domain namely "Carboxy-terminal Large" and "Carboxy-terminal Small", respectively The N-terminal E is residue 1580 in SP-R210$_S$ and 1938 in SP-R210$_L$.

The murine U18AC2 unique insert is the 15 amino acid sequence that is underlined and italicized as shown in the following amino acid sequence context:

```
                                        (SEQ ID NO: 2)
EDEMESDENEDLINSLQDMVTKYQKKKNKLEGDSDVDSELEDRVDRVKS

WLSKNKGPSKAPSDDGSLKSSSPTSHWKPLAPDPSDDEHDPVDSISRPRF

SHSYLSDSDTEAKLTETSA.
```

This amino acid sequence is also referred to herein as "R350." This sequence is available under GenBank accession number AAV80766.1 for SP-R210 alpha subunit splice variant CL.

FIG. 2 provides an amino acid sequence alignment of murine (MSP) and human (HSP) SP-R210 carboxy-terminal CS and CL amino acid sequences. Colored amino acids indicate differences between the murine and human sequence as indicated in the legend. For certain embodiments of this disclosure as demonstrated in the Examples and the Table presented herein, we used the murine R350 (SP-R210CL) sequence to immunize mice. This protein comprises a tag of six histidines at the carboxy terminus for use in protein purification. The distinguishing peptide of CL is absent in CS and identical with a single conserved substitution K to R between mouse and human CL and we have demonstrated that the murine antibodies are cross-reactive to the human homologue.

One aspect of the present disclosure comprises novel binding partners which bind with specificity to human surfactant protein A (SP-A) receptor. In embodiments, the binding partners comprise antibodies and/or antigen binding fragments thereof which bind with specificity to an SP-A isoform. In embodiments, the isoform to which the specific binding partners bind is the SP-R210$_L$ isoform, or the SP-R210$_S$ isoform.

We have generated a series of hyridomas that are characterized in the Table presented in FIG. 14. Each of these hybridomas, as well as cell cultures comprising them and their progeny are encompassed by the invention. Further, each of the polynucleotides that encode the antibodies produced by the hybridomas are included in the invention in their native and isolated forms, as are the mRNAs they produce in their native and isolated forms, as are cDNAs generated from those mRNAs. Expression vectors comprising polynucleotides that encode the monoclonal antibodies and antigen binding fragments thereof are included, as are cell cultures that contain such expression vectors. In embodiments, the present disclosure comprises making monoclonal antibodies (mAbs) produced by the hybridomas set forth in the Table of FIG. 14 by isolating the mAbs from the hybridoma media, as well as recombinant methods of making the mAbs and antigen binding fragments thereof by introducing an expression vector encoding such a mAb or an antigen binding fragment thereof into a cell culture, allowing expression of the mAb or antigen binding fragment thereof, and isolating the recombinantly produced mAb or antigen binding fragment thereof form the cell culture. In embodiments, polynucleotides provided by the invention encode one or more of the complementarity determining regions (CDRs) of the mAbs. In embodiments, the polynucleotides encode the CDR1, CDR2, CDR3, or a combination thereof.

Thus, in one aspect, the present disclosure comprises one or more isolated and/or recombinantly or otherwise synthesized binding partners which specifically recognize the SP-R210$_L$ isoform, or the SP-R210$_S$ isoform. Such binding partners can include antibodies and antigen binding fragments thereof that can specifically bind to and distinguish the SP-A isoforms from one another. In embodiments, the antigen binding fragments can comprise Fab fragments, Fab' fragments, F(ab')$_2$ fragments, Fd fragments, Fv fragments, scFv fragments, aptamers and diabodies. Antibodies directed to the SP-R210$_S$ isoform may bind with specificity to one or more epitopes in the unique 15 amino acid sequence described above as a component of the U18AC2 (SP-R210$_S$) amino acid sequence that is believed to define the S form in macrophages. In another embodiment, the unique 15 amino acid sequence is comprised by or participates in the formation of a conformational epitope that is specifically recognized by a mAb or antigen binding fragment thereof Likewise, in certain embodiments, the mAbs or antigen binding fragments thereof are able to specifically bind to the R210$_L$ isoform due to the absence of the unique 15 amino acid sequence in the SP-R210$_S$ isoform, which may result in linear or conformational epitopes that provide a binding site for such binding partners. mAbs that are directed to the N-terminal 458 amino acids that are in R210$_L$ but not in R210$_S$, are also encompassed by the present disclosure.

In embodiments, the antibodies and antigen binding fragments of them will specifically recognize at least one epitope present in at least 7 contiguous amino acids of the SP-RR210$_L$ or the SP-R210$_S$ protein, and in embodiments, binding partners provided by this disclosure can comprise at least one paratope that recognizes at least one of the foregoing 7 amino acid segments, or at least two paratopes that recognize at least one of the foregoing segments.

Since the hybridomas remain in our possession and can be readily characterized, the DNA encoding the immunoglobulin (Ig) they secrete can be sequenced, and thus the amino acid sequence of the Ig can be determined, and the complementarity determining regions (CDRs) of the Ig heavy and light chains can be determined and used to make synthetic versions of the antibodies made by the hybridomas, or to make antigen binding moieties as further described herein. Alternatively, the cell that produces the antibody can be cloned to produce identical daughter clones which will provide an ongoing source of monoclonal antibodies. In this regard, in certain and non-limiting embodiments, the monoclonal antibodies and/or fragments thereof are produced by the hybridoma termed P2H10, or the hybridoma termed P4G4 as shown in FIG. 14, or are produced recombinantly but have the same amino acid sequences, or the same CDR sequences, of the mAbs produced by the hybridoma termed P2H10, or the hybridoma termed P4G4 as shown in FIG. 14. In embodiments, the mAbs and/or fragments thereof comprise sequences or segments of the amino acid sequences provided in FIG. 30A (P2H10 heavy chain protein and CDRs, FIG. 30C (P2H10 light chain protein and CDRs), FIG. 30E (P4G4 heavy chain VH protein and CDRs), FIG. 30G (P4G4 light chain protein), and combinations thereof. Non-limiting examples of DNA sequences encoding such mAbs and fragments are illustrated in FIGS. 30B, 30D, 30F and 30H, respectively. For convenience, from time to time in this specification as is customary and will be apparent to those skilled in the art, mAbs produced by the hybridomas are also referred to using the same names as the hybridomas themselves.

We have determined the epitopes that are recognized by the two representative mAbs produced by the P2H10 and P4G4 hybridomas. For mAb P4G4 there are two epitopes: KYQKKKNK (SEQ ID NO:15) and VKSWLSKNK (SEQ ID NO:16). These provide a consensus motif of: KxxxxKNK (SEQ ID NO:17), wherein x is any amino acid. For mAb P2H10 the epitope is DLINSLQD (SEQ ID NO:18). These epitopes can be viewed in context of the two isoforms in FIG. 2, and it will be apparent that the P2H10 mAb detectably binds only the S isoform, while P4G4 detectably binds both the S and L isoforms. However, P4G4 is considered in embodiments to bind with specificity to the S form because it has not been observed to cross-react with any other protein. In embodiments, the disclosure encompasses any other antibodies and fragments thereof that bind with specificity to any one or any combination of these epitopes, and includes compositions and methods for making and using such antibodies and fragments that as described herein.

As will be recognized from the amino acid sequences presented in FIG. 30, in embodiments, the present disclosure comprises a mAb or fragment thereof that binds with specificity to surfactant protein A SP-R210 receptor, the mAb or fragment thereof comprising (I) a variable heavy chain sequence comprising: a) a heavy chain complementarity determining region 1 (P2H10-HCDR1) comprising the sequence GYIFSDYYMR (SEQ ID NO:3); and b) a heavy chain complementarity determining region 2 (P2H10-HCDR2) comprising the sequence DINPKNGDTFYNQK-FKGK (SEQ ID NO:4); and c) a heavy chain complementarity determining region 3 (P2H10-HCDR3) comprising the sequence REGD (SEQ ID NO:5); and/or a variable light chain sequence comprising: d) a light chain complementarity determining region 1 (P2H10-LCDR1) comprising the sequence RSSQTILHSNGNTYLE (SEQ ID NO:6); and e) a light chain complementarity determining region 2 (P2H10-LCDR2) comprising the sequence KVSKRFS (SEQ ID NO:7): and f) a light chain complementarity determining region 3 (P2H10-LCDR3) comprising the sequence LQG-SHVPLT (SEQ ID NO:8). Thus, the disclosure includes any mAb or antigen binding fragment thereof that comprises one or a combination of the CDRs that contribute to epitope recognition in the mAb made by the P2H10 hybridoma.

The disclosure also includes a mAb or fragment thereof comprising (II) a variable heavy chain sequence comprising: i) a heavy chain complementarity determining region 1 (P4G4-HCDR1) comprising the sequence GYTFTDYAMH (SEQ ID NO:9): and ii) a heavy chain complementarity determining region 2 P4G4-HCDR2) comprising the sequence VISTYNGNTKYNQKFKD (SEQ ID NO:10): and iii) a heavy chain complementarity determining region 3 P4G4-HCDR3) comprising the sequence ART-DYDNGDYVMDY (SEQ ID NO:11): and a variable light chain sequence comprising: iv) a light chain complementarity determining region 1 (P4G4-LCDR1) comprising the sequence KASQDINNYLS (SEQ ID NO:12): and v) a light chain complementarity determining region 2 (P4G4-LCDR2) comprising the sequence RANRLVD (SEQ ID NO:13): and vi) a light chain complementarity determining region 3 (P4G4-LCDR3) comprising the sequence LQYDEFPLT (SEQ ID NO:14). Thus, the disclosure includes any mAb or antigen binding fragment thereof that comprises one or a combination of the CDRs that contribute to epitope recognition in the mAb made by the P4G4 hybridoma.

In embodiments the disclosure binds with specificity to only the SP-R210$_S$ isoform of the SP-R210 receptor, or the monoclonal antibody or fragment thereof of binds with specificity to SP-R210$_S$ and SP-R210$_L$ isoforms of the SP-R210 receptor.

The disclosure also includes mixed heavy and light variable regions, and thus includes all combinations of the P2H10 heavy chains with the PFG4 light chains, and vice versa. The disclosure accordingly includes monovalent and multivalent SP-R210 receptor binding partners.

In embodiments, the disclosure comprises a method for treating an individual in need thereof comprising administering to the individual an effective amount of a composition comprising a monoclonal antibody or fragment thereof as described herein. In certain aspects the individual is in need of treatment for a viral or bacterial infection. In certain embodiments the individual is in need of treatment for a viral influenza infection, which may or may not be associated with pneumonia.

In certain embodiments the disclosure comprises a pharmaceutical composition comprising a monoclonal antibody or fragment thereof as described herein.

In certain embodiments the mAbs or antigen binding fragments thereof are components of fusion proteins, or are chemically modified such that they are covalently attached to another moiety, or are fixed to a substrate, or are present in a complex with the SPR210 protein.

Any antibody produced by a non-human mammal derived hybridoma of the type described herein can be modified to provide a chimeric or partially or fully humanized form, and the present disclosure includes such modifications. In general, "humanized" forms of non-human (e.g., mice) antibodies are chimeric antibodies that contain minimal sequence derived from the non-human antibody. Humanized antibodies are essentially human immunoglobulins (also called the "recipient" antibody) in which residues from a hypervariable region of the recipient are replaced by residues from a hypervariable region of a non-human species (also called a "donor" antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also can comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992).

Methods for humanizing non-human antibodies are well known in the art. Humanization of an antibody produced according to the present disclosure can be essentially performed following the method of Winter and co-workers by substituting mouse CDR sequences for the corresponding sequences of a human antibody (Jones et al., Nature, 321: 522-525 (1986); Riechmann et al., Nature, 332:323-327 (1988); Verhoeyen et al., Science, 239:1534-1536 (1988)).

In embodiments, the antibodies and/or antigen binding fragments of the invention are provided in a pharmaceutical formulation, which can contain such components as pharmaceutically acceptable carriers, excipients or stabilizers.

In embodiments, the antibodies or antigen binding fragments thereof may be administered by any suitable means, including parenteral, subcutaneous, intraperitoneal, intrapulmonary, and intranasal. Parenteral infusions include intramuscular, intravenous, intraarterial, intraperitoneal, intralymphatic or subcutaneous administration. In addition, the monoclonal antibodies and/or antigen binding fragments thereof may be administered by pulse infusion, e.g., with declining doses.

In various embodiments, methods of using the mAbs and antigen binding fragments thereof are provided. In one aspect, the disclosure includes administering a composition comprising an effective amount of a mAb and/or an antigen binding fragment thereof to an individual in need. In embodiments, the individual in need is a subject that is infected with, or is at risk of becoming infected with a microorganism (including a virus), wherein the microorganism expresses a ligand for the SP-R210$_L$ isoform, or the SP-R210$_S$ isoform, or both. In an embodiment, the individual is in need of prophylaxis and/or therapy for a bacterial infection. In an embodiment, the individual is in need of prophylaxis and/or therapy for a viral infection. In an embodiment, the individual is in need of prophylaxis and/or therapy for an infection by a pathogenic strain of *Staphylococcus*, respiratory syncytial virus, or by an influenza virus. In embodiments, the amount of the antibody or antigen binding fragment thereof is adequate to, for example, block or inhibit binding of SP-A, or to inhibit endocytic trafficking of a complex comprising SP-A, wherein the SP-A is expressed by a pathogenic microorganism such that a symptomatic infection in the individual is not established, or a symptomatic infection in the individual is alleviated more quickly than for an individual who does not receive the antibody or the antigen binding fragment thereof. In embodiments, the individual is in need of reduced inflammation, such inflammation being caused by or correlated by infection, or trauma, or other insult to the individual, or a disease that is correlated with increased inflammation, such as cardiovascular disease, chronic obstructive pulmonary disease, and cancer.

In another aspect the disclosure includes forming a complex between a mAb or antigen binding fragment thereof and an SP-A receptor isoform. In embodiments, the complex can be detected for use in immunological-based detection of cells which express a particular isoform, or can be used in various techniques for sorting cells, such as by flow cytometry and fluorescence-activated cell sorting (FACS). In embodiments, a biological sample can be obtained from an individual and tested to determine the presence, absence, or amount of cells, such as macrophages, which express the SP-R210$_L$ isoform, or the SP-R210$_S$ isoform, or both. In embodiments, a biological sample can be obtained from an individual and manipulated to, for example, deplete cells which express the SP-R210$_L$ isoform, or the SP-R210$_S$ isoform, or to purify such cells from the sample for analysis and/or for culturing in vivo, or to provide enriched populations of such cells. Such approaches can be performed using any suitable immunoseparation technique based on specific recognition of the SP-R210$_L$ isoform, or the SP-R210$_S$ isoform as the case may be, by using the mAbs or antigen binding fragments thereof. In embodiments, the mAbs or antigen binding fragments thereof can be attached to a substrate and used, for example, as capture agents.

In another embodiment, mAbs or antigen binding fragments thereof may be conjugated to another moiety, such as in the case of a fusion protein between the mAb or antigen binding fragment thereof and another polypeptide sequence, penetrating peptides or molecules to gain access to the receptor intracellularly, or they may be coupled to a therapeutic agent, or an agent that can function as a detectable label, including but not necessarily limited to a fluorescent label.

In embodiments, the disclosure includes methods of using the antibodies or antigen binding fragments thereof in ex vivo applications, including but not necessarily limited to adoptive immunotherapy approaches. In an embodiment, macrophages are isolated from an individual, contacted with antibodies or antigen binding fragments thereof, and after a period of time the macrophages are introduced into an individual from which they were obtained, or another individual.

In an embodiment the compositions and methods described herein are suitable for veterinarian purposes, i.e., for use in non-human animals.

The following Examples will illustrate but not limit the invention.

EXAMPLE 1

Figure 3:
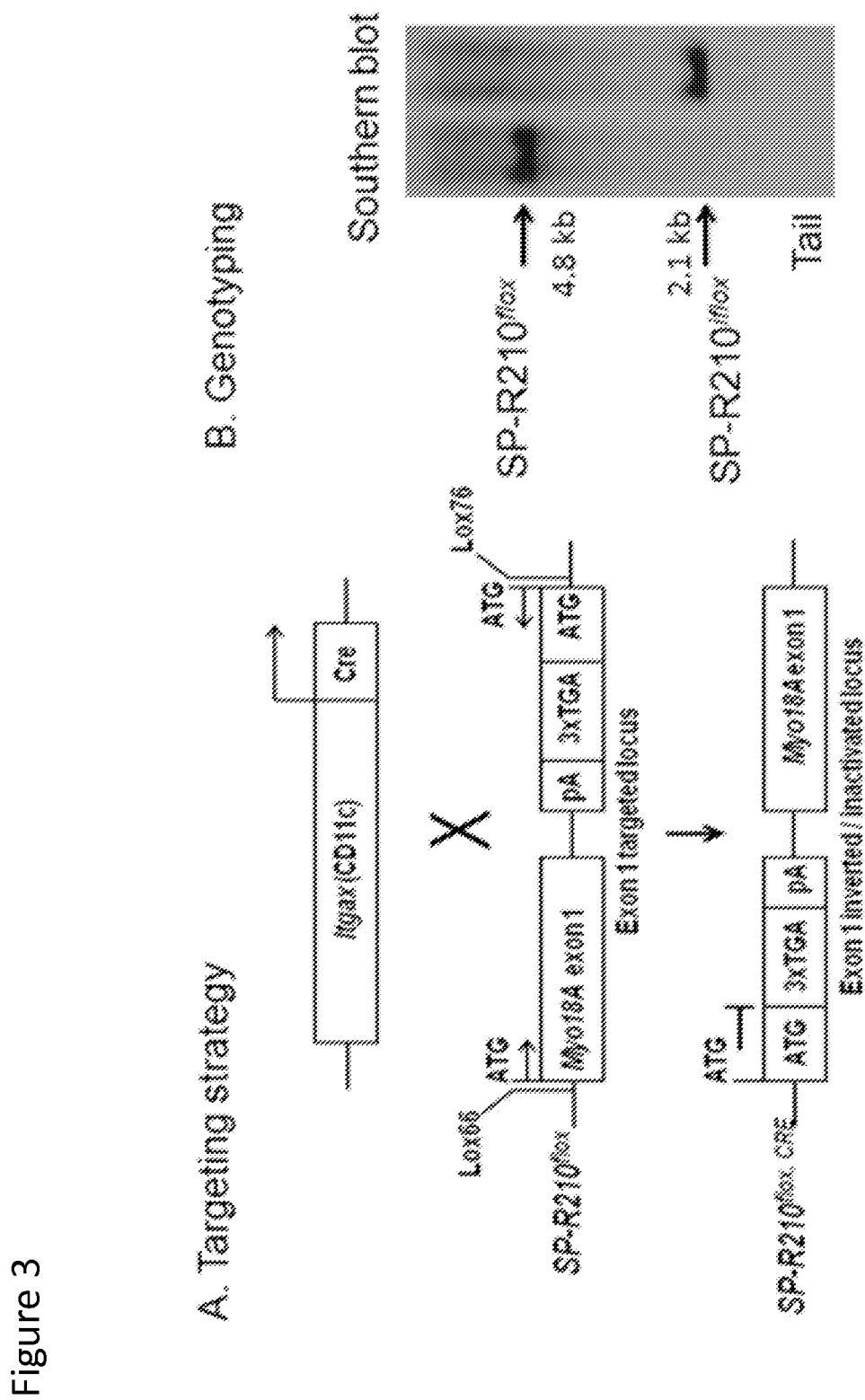

As is demonstrated in FIG. 3, the disclosure provides a graphical depiction of a cloning procedure for generating a conditional disruption of SP-R210 in MΦ in transgenic mice. As illustrated in this Figures, this was performed by CRE-mediated inversion of SP-R210 exon 1.SP-R210flox/+ mice were crossed to CD11cCRE mice to generate heterozygous SP-R210–/+ with the inverted knockout allele and SP-R210flox/+progeny. SP-R210$_L$ deficient (DN) cells lines (300 & 350) were also constructed by dominant negative disruption of SP-R210 in Raw264.7 MΦ.

EXAMPLE 2

Figure 4:
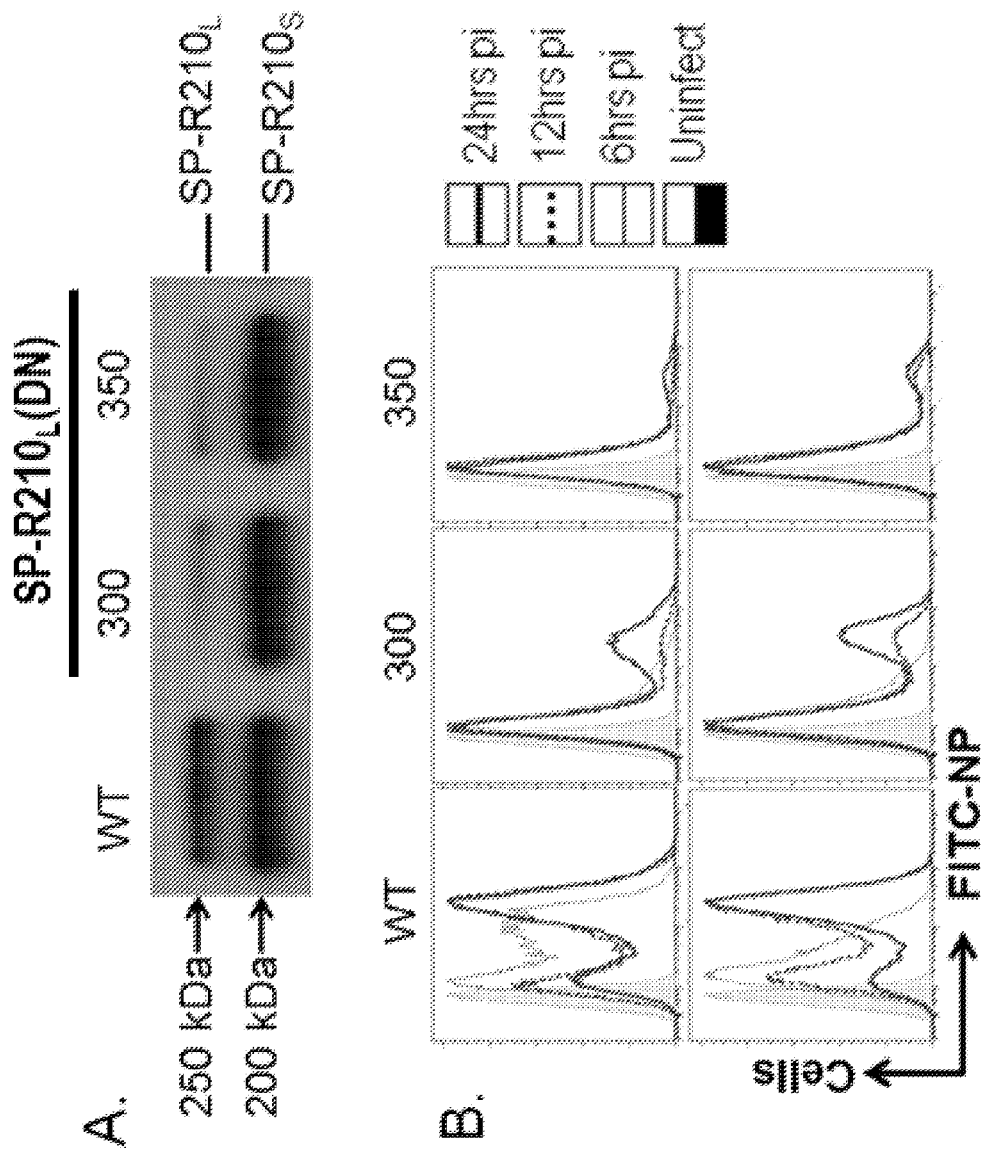

As is demonstrated in FIG. 4, this disclosure demonstrates that a lack of SP-R210$_L$ blocks infection of influenza A vius (IAV) in MΦ. Panel A) Western blot analysis of SP-R210 isoforms in RAW 264.7 WT and SP-R210$_L$(DN) cells. Panel B) Control WT and SP-R210L(DN) cells were infected with IAV PR8 (H1N1 strain, panel B upper row) and Phil82 (H3N2 strain, Panel B lower row), then infection was allowed to progress and harvested at 6, 12, or 24 hrs and processed to evaluate infection by flow cytometry. For this purpose, the cells were stained with antibodies to influenza nuclear protein NP. Flow cytometry of stained cells discerns two peaks in control cells. The peak on the left indicates incoming virus and decreases over time as the infection progresses, and the peak on the right indicates synthesis of new NP that accumulates over time in the nucleus as the virus proliferates; the NP synthesis peak is attenuated or absent in SP-R210$_L$(DN) cells, indicating that influenza co-opts SP-R210$_L$ to infect the target cell.

EXAMPLE 3

Figure 5:
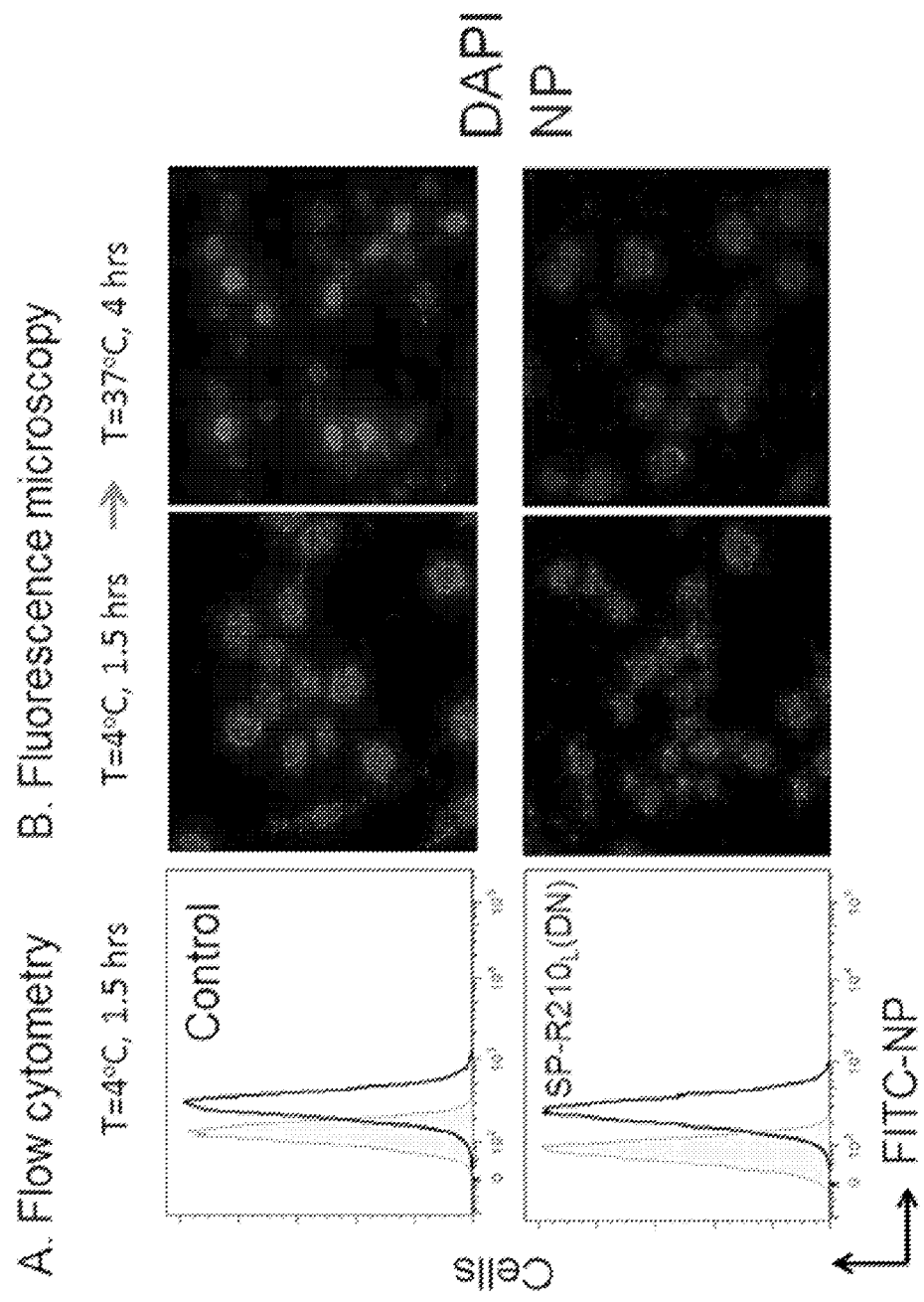

As is demonstrated in FIG. 5, this disclosure demonstrates that a lack of SP-R210$_L$ does not affect binding and internalization of IAV, but the endocytic trafficking of NP to nucleus is blocked when SP-R210$_L$ is absent. Control and SP-R210$_L$(DN) MΦ were infected with 1:1 MOI of IAV PR8. A) Bound virus was visualized by flow cytometry using NP antibodies, B) Cells were switched to 37° C. for 4 hr and NP was visualized by fluorescence microscopy. Nuclei were stained with DAPI.

EXAMPLE 4

Figure 6:
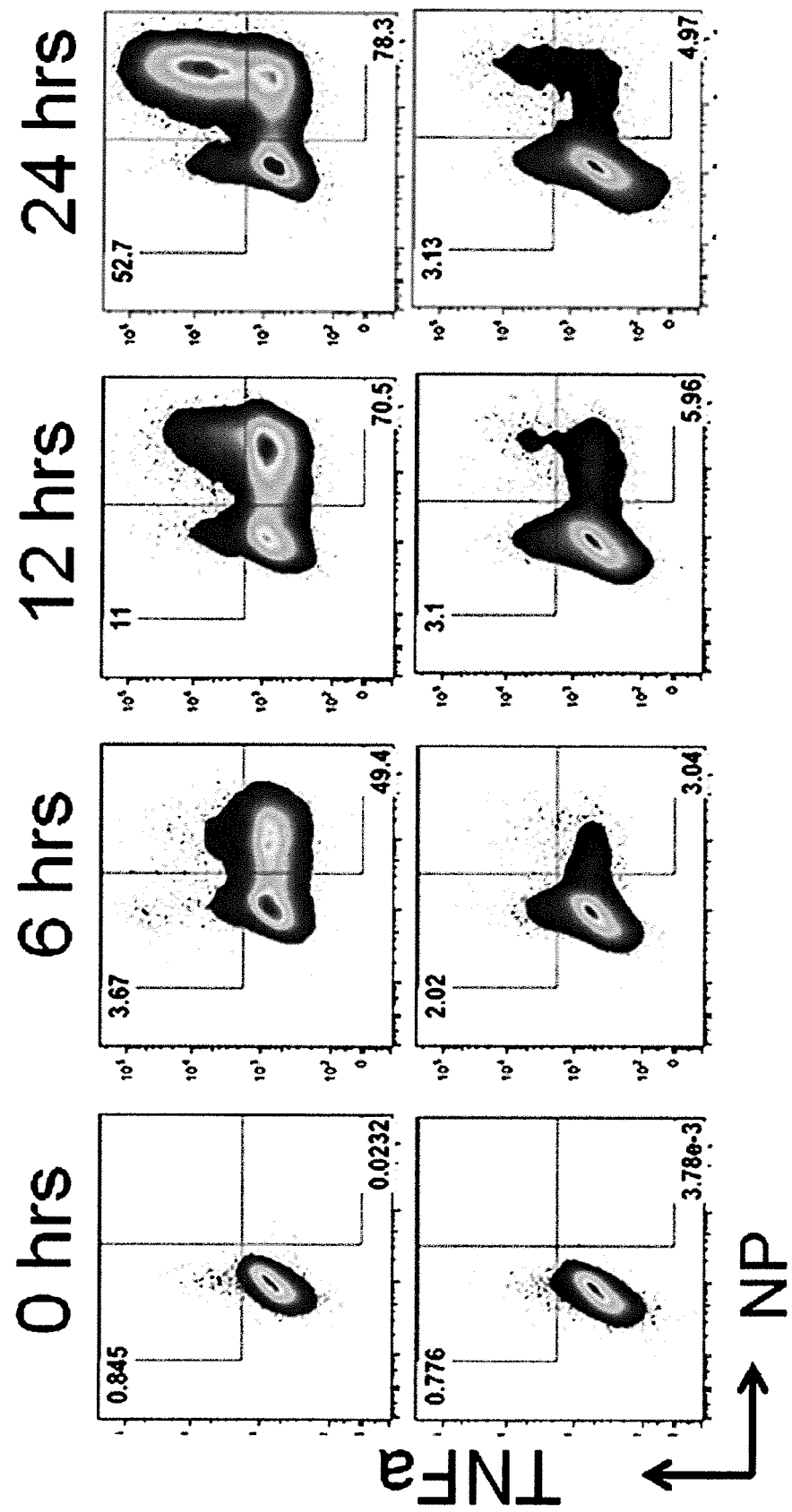

As is demonstrated in FIG. 6, this disclosure demonstrates that SP-R210$_L$ -mediated IAV infection of MΦ is coupled to the TNFα production. Control (upper) and SP-R210$_L$(DN) (lower) cells were infected with PR8. Intracellular NP and TNFα were analyzed by flow cytometry.

EXAMPLE 5

Figure 7:
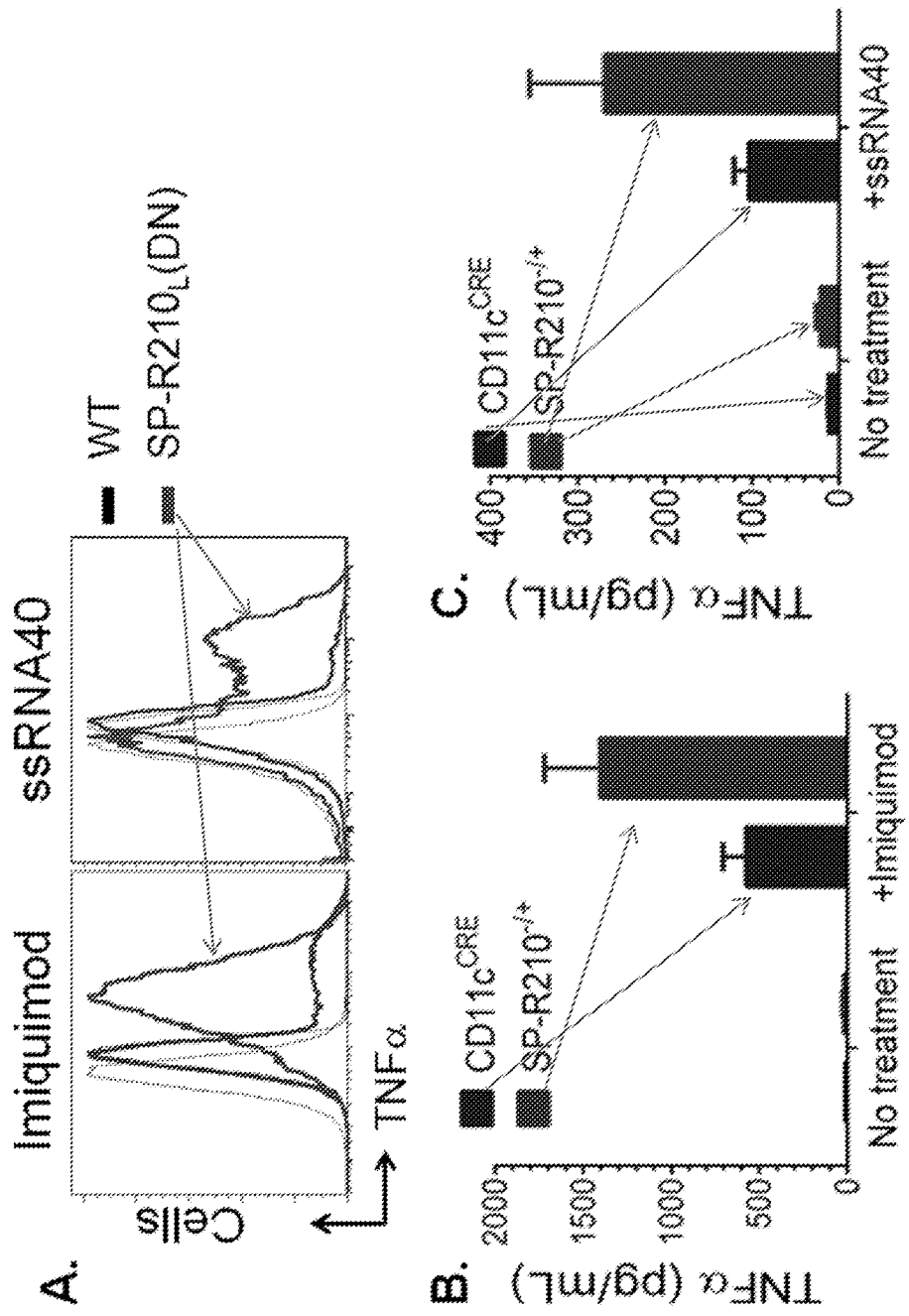

As is demonstrated in FIG. 7, this disclosure demonstrates that SP-R210$_L$-deficient MΦ and AMs are hyper-responsive to TLR7 ligands. (7A). Untreated (thin histograms) or cells incubated (thick histograms) with 2 µg/mL imiquimod or ssRNA40 for 8 hrs. Intracellular TNFα were analyzed by flow cytometry. AMs collected by lung lavage were treated with 2 µg/mL imiquimod (7B) or ssRNA40 (7C). TNFα was measured in culture media by ELISA 24 hrs after treatment.

EXAMPLE 6

Figure 8:
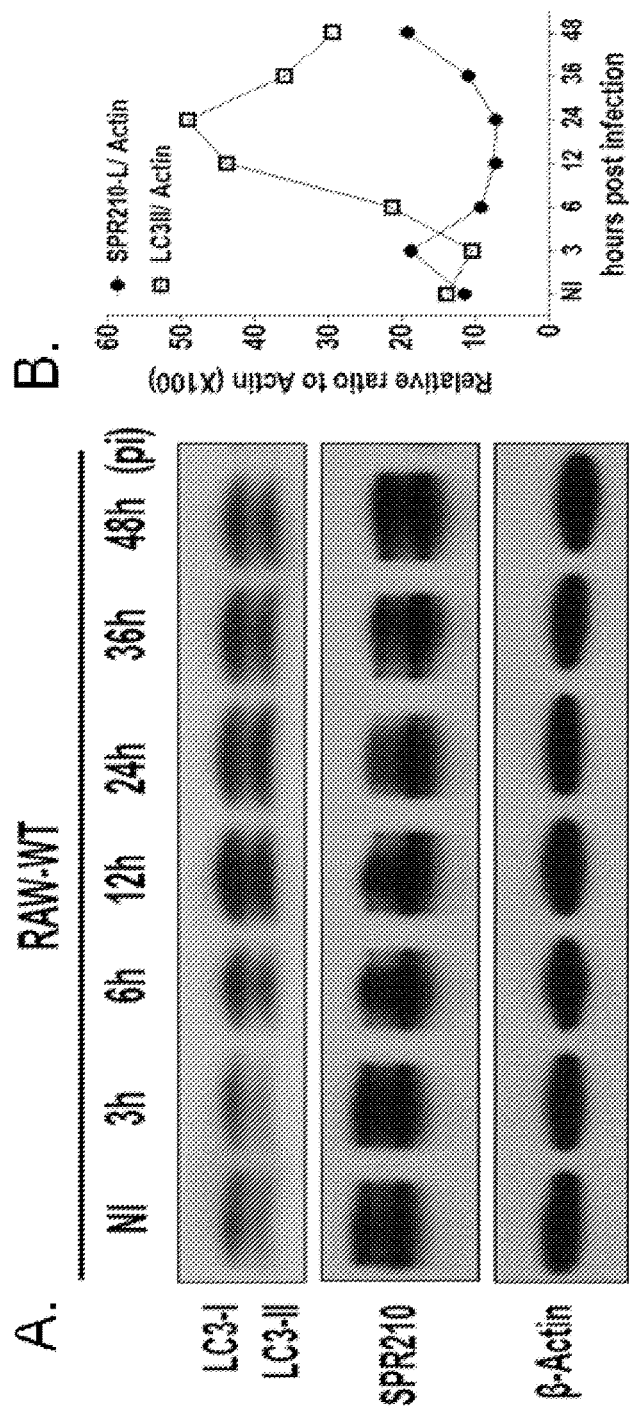

As is demonstrated in FIG. 8, this disclosure shows that IAV infection results in inhibition of SP-R210$_L$ expression in a time-dependent manner. (8A) Control WT cells were infected with PR8, harvested and processed for western blot with anti-SP-R210, or b-actin. (8B) Densitometric data were obtained using Bio-Rad Quantity One software and graphed.

EXAMPLE 7

Figure 9:
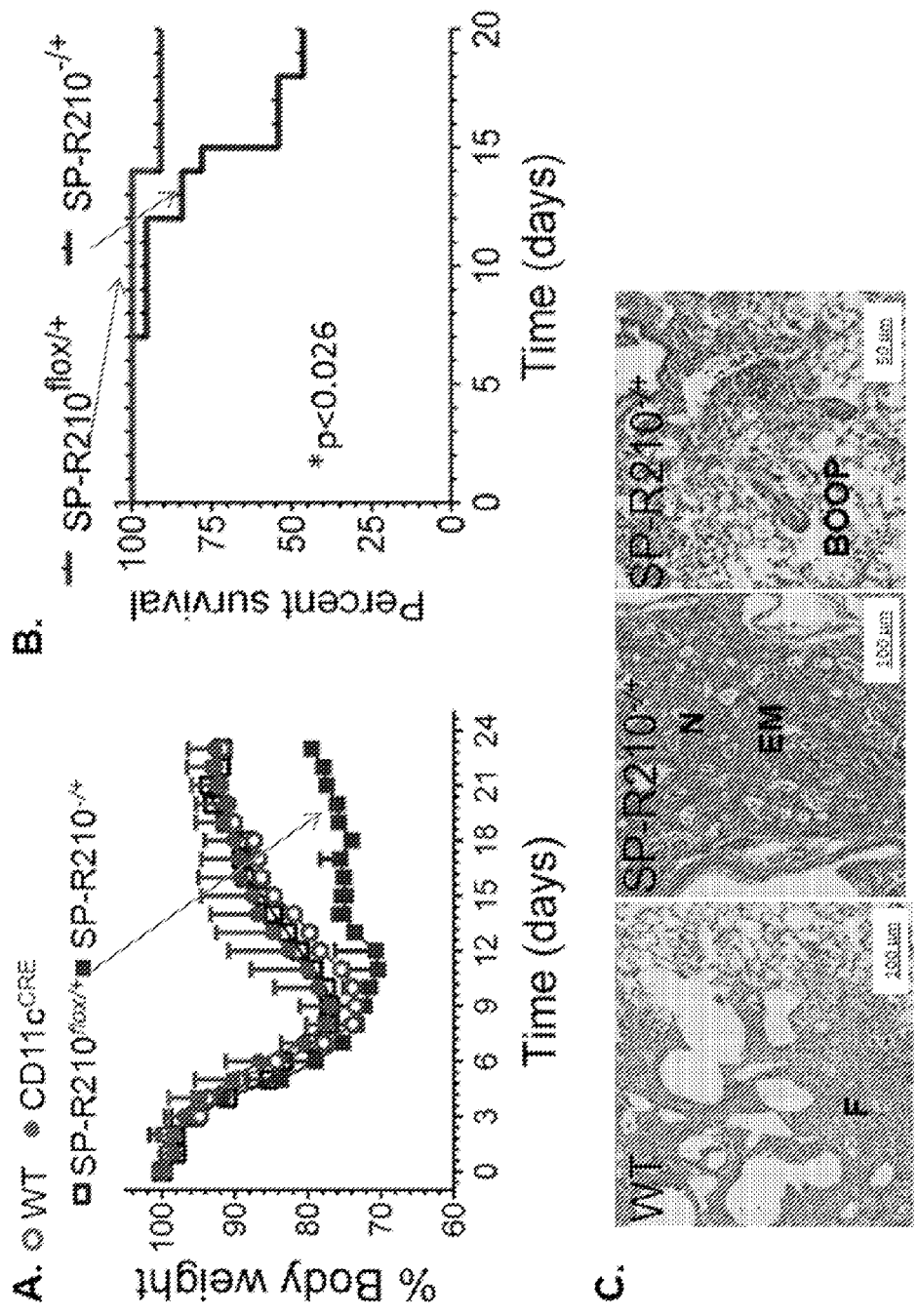

As is demonstrated in FIG. 9, this disclosure demonstrates that SP-R210$_L$-deficient mice are significantly more susceptible to IAV infection. Mice were infected with 0.75 LD50 of PR8 per mice. Body weight (A) and survival (B) were monitored daily. (C) Lungs tissue were isolated and processed for HE staining for histopathology (18 days post-inoculation). EM: epithelial cell metaplasia; N: neutrophils; .BOOP: Bronchiolitis obliterans organizing pneumonia.

EXAMPLE 8

Figure 10:
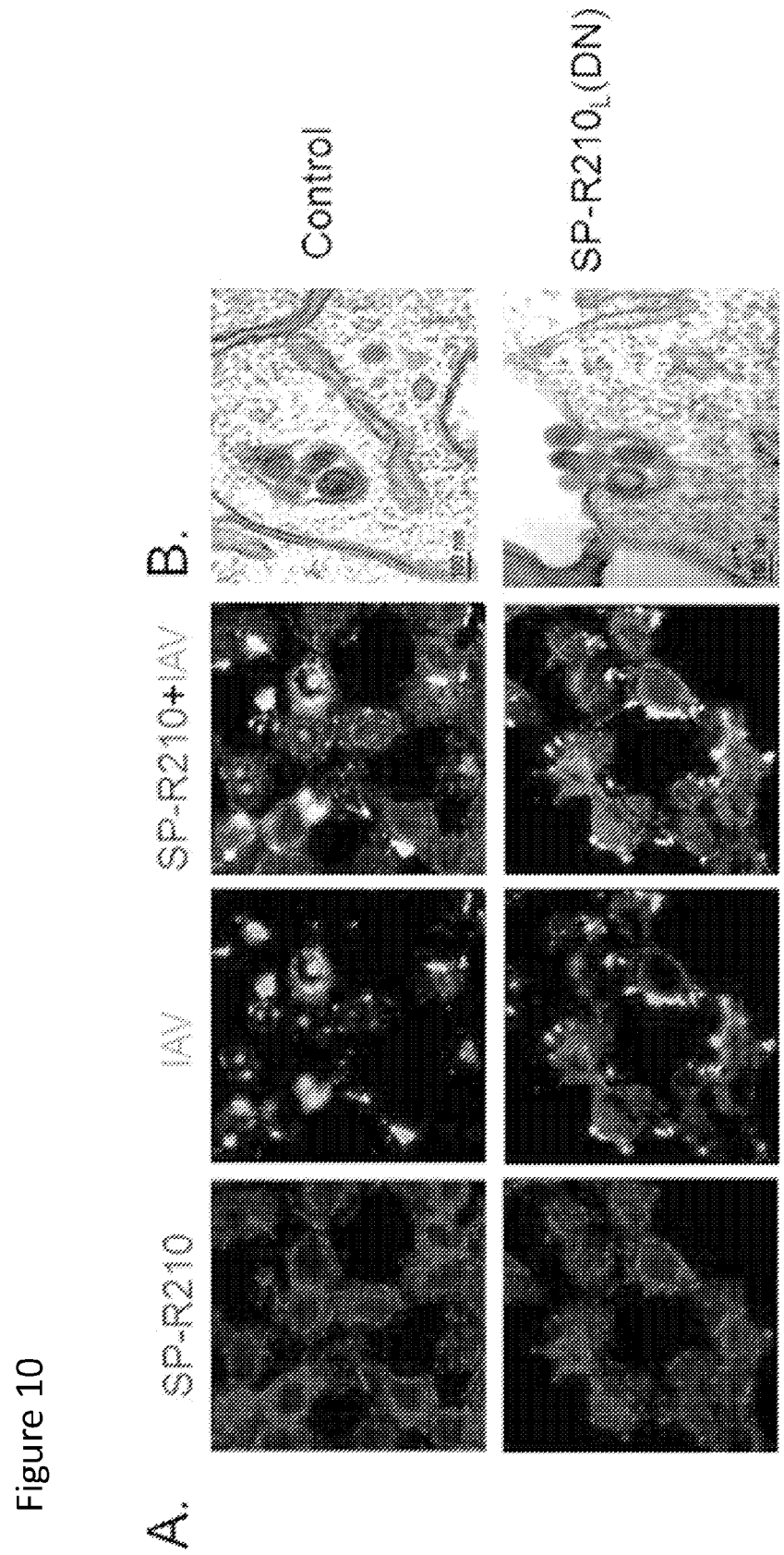

As is demonstrated in FIG. 10, this disclosure demonstrates SR-R210 isoform-mediated binding and internalization in macrophages. A) SP-R210 and IAV were localized by confocal (A) and (B) electron microscopy 6 hours after infection.

EXAMPLE 9

Figure 11:
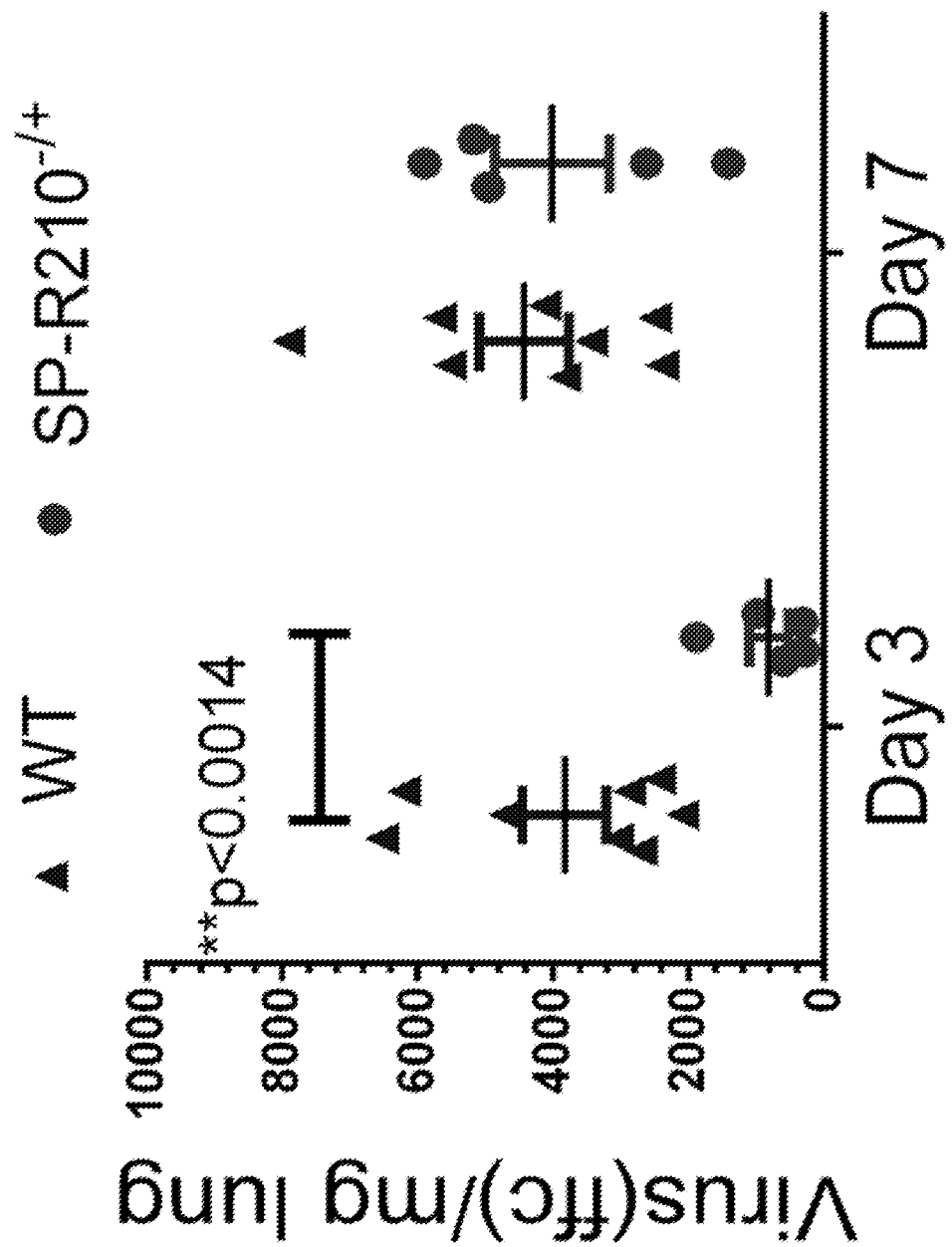

As is demonstrated in FIG. 11, this disclosure demonstrates that disruption of SP-R210 in AM delays replication of IAV in vivo. Mice were infected intranasally with 0.75 LD50 of PR8. Total RNA of whole lung tissue was extracted 3 and 7 days post-inoculation. The mRNA for the virus Ml gene was quantitated by real time PCR against a standard curve of purified virus RNA.

EXAMPLE 10

Figure 12:
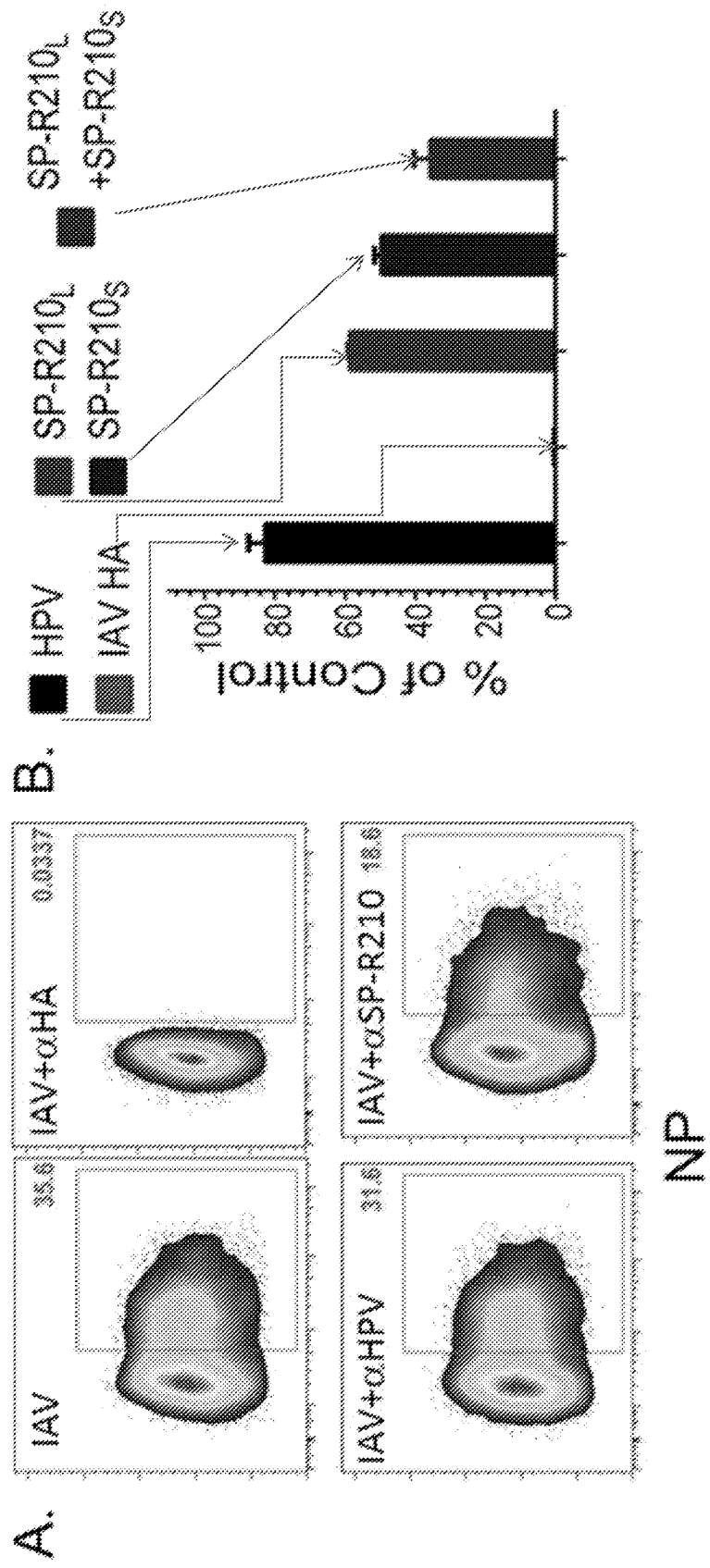

As is demonstrated in FIG. 12, this disclosure provides flow cytometry and graphical data showing antibodies to SP-R210 inhibit IAV infection. The data presented in this Figure were obtained using mAbs produces by hybridomas P3D7, P2H10, and P2F8. We also tested P2F5, P6B9, and P8F6. Those with detectable activity are noted as +or +/- on FIG. 14). To obtain these data, macrophages were pre-incubated for 1 hour in the absence or presence of hybridoma media containing antibodies (α) to IAV hemagglutinin (HA), a human papilloma virus (HPV) surface protein, or antibodies to SP-R210$_L$ (A and B), or a combination of αSP-R210$_L$ and αSP-R210$_S$ antibodies. Cells were then infected with PR8 an infection determined by flow cytometry after 24 hours.

EXAMPLE 11

Figure 13:
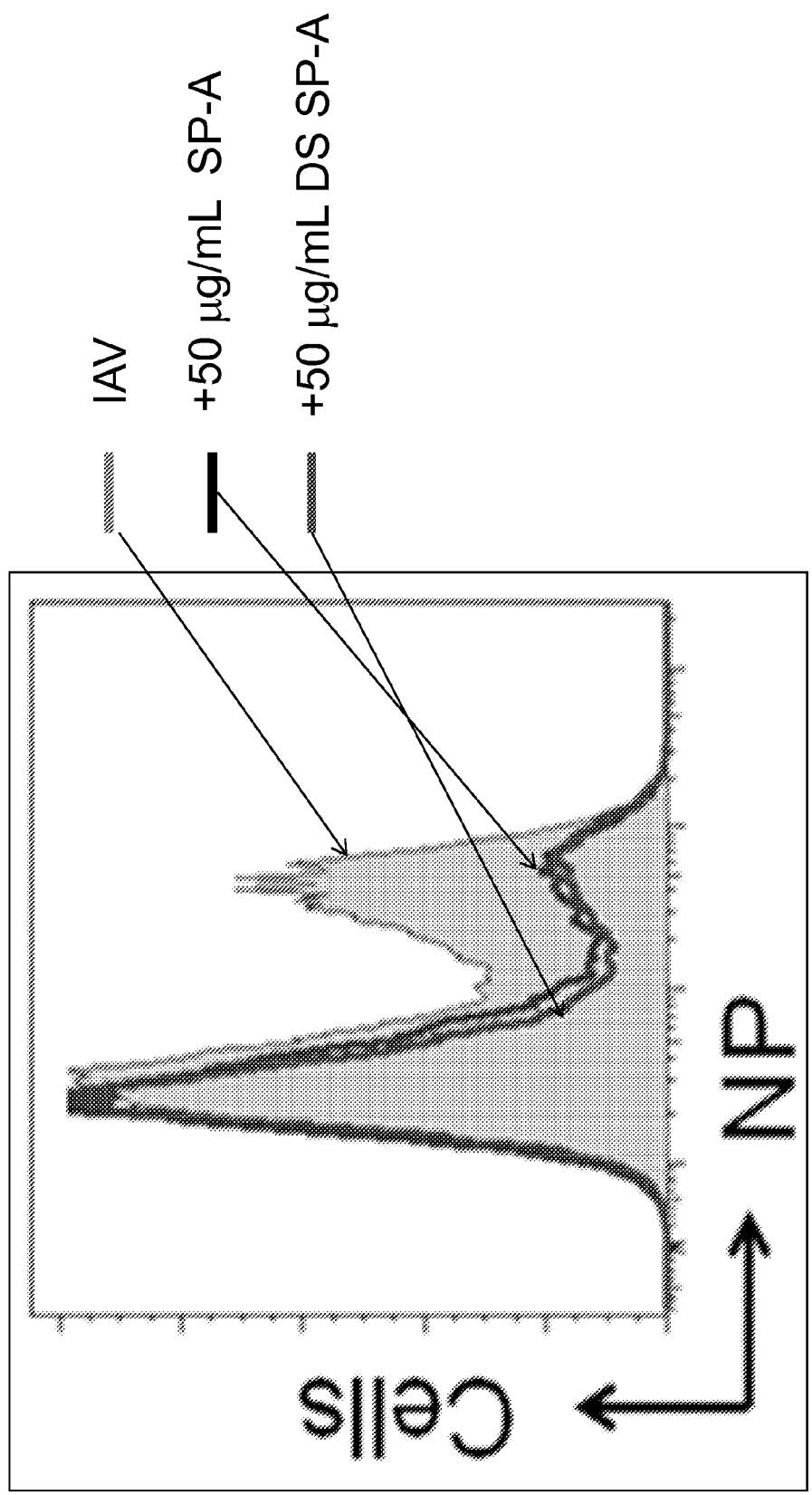

As is demonstrated in FIG. 13, this disclosure demonstrates that desialylated (DS) SP-A blocks infection of macrophages with IAV. Thus, SP-A competitively inhibits binding of the influenza virus to the receptor. This Figure demonstrates that both native and desialylated SP-A compete for influenza binding to the same receptor, i.e. SP-R210, rather than because influenza binds the sialic acid on the SP-A. Without intending to be constrained by any particular theory, the biological significance of this is that polymorphisms or mutations in SP-A can alter its affinity for the receptor allowing breakthrough infection with influenza. Thus, it is expected that use of the antibodies according to the present disclosure will be a considerably improved alternative for treatment.

It will be apparent from the foregoing that SP-R210$_L$ is required for endocytic trafficking of IAV to the nucleus in MΦ, that SP-R210$_L$-deficient cells are hyper-responsive to inflammation, and that the mouse model shows that impairing SP-R210$_L$ in AMs reduces the beneficial function of SP-R210$_L$ in IAV infection, promotes more virus proliferation in the cells other than AM, and leads to excessive lung inflammation. Thus, and without intending to be bound by any particular theory, it is considered that by co-opting SP-R210$_L$, IAV causes a functional 'knock-down', reducing the beneficial function of SP-R210$_L$ and leading to enhanced inflammation in the lung. Accordingly, it is reasonable to expect that blocking the IAV interaction with SP-R210$_L$ using the compositions and methods of this disclosure, IAV infection and/or its attendant inflammation can be reduced. Further, there is no particular reason to limit the disclosure to IAV, as the data, results and Figures provided herein strongly support a wide variety of uses for mAbs or antigen binding fragments thereof for use in prophylaxis and/or therapy for infection by many distinct pathogens, and further demonstrate the feasibility of using these reagents in the even more broad sense of modulating inflammation and ex vivo manipulation of cell populations, as well as diagnostic approaches.

EXAMPLE 12

In this and the following Examples, the terms SP-R210 and Myo18A are used for immune and non-immune cells, respectively. The reason for this name is based on experimental and computational evidence indicating that the Myo18A gene is subject to cell type-dependent alternative splicing. For example, in addition to splicing that generates SP-R210$_L$ and SP-R210$_S$ isoforms, splicing of small exons generates alternate forms of the unique carboxy-terminal domain of Myo18A in macrophages. As is known in the art and is discussed briefly above, SP-A utilizes diverse regulatory and counter-regulatory mechanisms to modulate innate immune functions of macrophages. In certain Examples of this disclosure, we analyzed macrophages lacking expression of the SP-R210$_L$ isoform. The findings indicate that SP-R210$_L$ and SP-R210$_S$ coordinate the function and expression of innate immune receptors in macrophages. Thus, in various embodiments, the present disclosure relates to modulating macrophage function to affect immune responses, and in particular the function and activity of macrophages. This Example provides a description of the materials and method used to obtain data presented in the Examples that follow it, and in some cases that will be apparent to those skilled in the art are also pertinent to the foregoing Examples.

Reagents and Antibodies

Chemicals were purchased from Sigma-Aldrich (St. Louis, Mo.). Pre-stained molecular weight markers were from Bio-Rad (Hercules, Calif.), and fetal bovine serum (FBS) from Atlanta Biologicals (Atlanta, Ga.). The TNFα ELISA kit was from eBioscience (San Diego, Calif.). Smooth lipopolysaccharide (LPS) from *Escherichia coli* serotypes O111:B6 or O26:B6 were from Sigma-Aldrich. The RNAeasy midi kit was from Qiagen (Valencia, Calif.). The High capacity cDNA reverse transcription kit and TaqMan qRT-PCR gene expression assays were from Life Technologies/Invitrogen (Carlsbad, Calif.). Fluorochrome conjugated monoclonal antibodies against CD11c (N418); CD11b (M1/70); CD14 (Sa2-8); CD282 (TLR-2; mT2.7); CD284 (TLR-4; UT41); SIRPα (P84); F4/80 (BM8); Ly-6C (HK1.4); TNFα (MPX-XT22), and CD16/32 Fc block (93) were from eBiosciences (San Diego, Calif.). The CD36 (72-1) and CD284 (TLR-4; Sa15-21) antibodies were from Biolegend (San Diego, Calif.). The SR-AI/MSR1 (clone: 268318) and CD87 (uPAR; clone 109801) antibodies were from R&D (Minneapolis, Minn.). Isotype matched controls were from eBiosciences or R&D. Unconjugated goat polyclonal against mouse CD14, TLR-2, CD36, SR-AI/MSR1, and rat monoclonal anti-mouse CD11b (M1/70) were purchased from R&D. Rabbit polyclonal antibodies against human SP-A were used as standard approaches. Antibodies to SP-B were from Seven Hills Bioreagents (Cincinnati, Ohio). Brefeldin A, and fix/permealizing solution for intracellular cytokine staining were from eBioscience. Antibodies to NF-kB subunit RelA(p65), RelA(p65)$^{S536}$, IRAK-1, and IκB were purchased from Cell Signaling. Secondary HRP- conjugated donkey anti-goat antibodies were from R&D. True blot HRP-conjugated anti-rabbit and protein G-Sepharose IP beads were from eBioscience or GE Lifesciences. The ECL chemiluminescence kit was from Perkin Elmer (Waltham, Mass.). The generation and purification of monoclonal anti-SP-R210 antibodies will be reported elsewhere. Dynasore was obtained from SIGMA, and 5-(N-Ethyl-N-isopropyl) amiloride (EIPA) and NSC23766 were from SelleckChem through Fisher Scientific.

Mice

WT C57BL/6 mice were purchased from JAX Labs (Bar Harbor, Minn.). The SP-A−/− mice were bred and maintained locally either at the University Of Cincinnati College Of Medicine or at Penn State College of Medicine. Mice were maintained in microisolator ventilated cages and provided autoclaved water and food ad libitum. SP-A−/− transgenic mice at the two Institutions were derived independently using known approached and backcrossed to the C57BL/6 genetic background. All procedures were in accordance to Institutional Animal Use and Care Committees.

Isolation of Alveolar Macrophages

Alveolar macrophages were isolated by alveolar using five consecutive washes of alveolar contents with 0.5 mL of PBS supplemented with 1 mM EDTA. Alveolar macrophages were collected by centrifugation and processed for Western blot analysis using standard techniques.

Purification and Characterization of Human SP-A

SP-A was isolated from discarded therapeutic lung lavage from alveolar proteinosis patients by modifications of the traditional butanol/octylglucoside extraction method of Hawgood and colleagues (Method 1) or according to detailed protocols known in the art (Method 2). SP-A preparations were dialyzed in 5 mM Hepes, pH 7.5, and stored frozen at −80° C. until use. All procedures used LPS-free water from a Millipore water purification system (Millipore RiOs 16 and Milli-Q Biocel with resistance of >18.2 MΩ). The concentration of LPS in purified SP-A was measured using the Limulus Amebocyte Lysate QCL-1000 assay (Lonza, Walkersville, MA). LPS was undetectable in SP-A purified by Method 1. The concentration of LPS in SP-A prepared using Method 2 was 20 pg/μg of protein. Protein purity was determined by silver-staining. For mass spectrometry, SDS-PAGE gels were stained with the Invitrogen SilverQuest staining kit. Proteins co-isolating with SP-A were excised, in-gel digested with trypsin and proteins identified by MALDI mass spectrometry (FIG. 27) at Penn State College of Medicine Mass Spectrometry Facility.

Cell Culture

The generation of control and SP-R210$_L$(DN) Raw264.7 cells was recently described by us [8]. Briefly, cells were stably transfected with pTriex-2 vector expressing the carboxy-terminal domain of SP-R210 (SP-R210$_L$(DN) cells) [6]. Control cells were transfected with empty vector. Cells were cultured for 20-48 hrs in RPMI supplemented with 10% fetal bovine serum (FBS). Cells were cultures in 96-well dishes at a density of 50,000 cell/well or 12-well dishes at a density of 150,000-250,000 cells/well.

Flow Cytometry

Control and SP-R210$_L$(DN) Raw264.7 cells were detached using non-enzymatic cell dissociation medium (SIGMA) and washed in PBS. Cells were blocked in PBS, pH 7.4, supplemented with 1% goat serum, 0.5% BSA, and 5 μg/ml of Fc block at a concentration of 1×10$^7$cells/ml for 1 hr on ice. Cells were stained with recommended concentrations of monoclonal antibodies for 30 min on ice. Cells were washed twice with PBS without protein or azide. Cells stained with eBioscience e506 fixable viability dye for 20 min at 4° C. Cells were washed once with FACS buffer (Hanks buffered salt solution (HBSS) containing Ca+and Mg+, 2% FBS, 0.02% sodium azide) then cells were fixed with 100 μl eBioscience intracellular (IC) fixation buffer for 30 min at room temperature, then permeabilized with eBioscience permeabilization buffer. For intracellular cytokine staining, cells were incubated with additives in the presence of Brefeldin A for set time points and then stained with anti-mouse TNFα conjugated to phycoerythrin (PE). Events were acquired using either a BD FACS Calibur or LSR II flow cytometer (BD Pharmingen) and analyzed using FlowJo flow cytometry analysis software (Treestar, Mountain View, Calif.).

Endocytosis Assays

Control and SP-R210$_L$(DN) cells were placed in 12 well plates at a density of 250,000 cells/well and cultured in RPMI/10% FBS for 20 hrs. The cells were then stimulated with 100 ng/ml or 2 μg/ml of LPS for CD14 and TLR-4 endocytosis assays, respectively, and harvested at 0, 1, 2, 3, and 4 hrs post-stimulation using cell dissociation buffer. Cells were blocked in PBS containing 1% goat serum and 5 μg/ml of Fc block for 30 min at room temperature, then processed for flow staining with PE-TLR4 antibody (BioLegend) for 30 min at room temperature. To test the effect of inhibitors, cells were 80 μM Dynasore to inhibit dynamin, 40 μM EIPA to inhibit macropinocytosis, or 100 μM NSC23766 to inhibit RAC1 in normal medium 30 min prior to addition of LPS. Cells-surface CD14 and TLR-4 were assessed by flow cytometry with Cy7-conjugated CD14 (clone Sa2-8) or PE-conjugated TLR-4 (clone Sa15-21) antibodies.

Generation of Cell Extracts and Western Blot Analysis

Cultured cells were washed in PBS and detached using non-enzymatic cell dissociation medium. Cell suspensions were centrifuged at 210×g at 4° C. and lysed in ice-cold lysis buffer by freeze and thaw cycles. Extracts were used immediately, or stored frozen at −80° C. Proteins were separated on 4-17% SDS-PAGE gradient gels and transferred to nitrocellulose by semi-dry blotting. The blots were then blocked in Tris-buffered saline, pH 7.5, supplemented with 0.1% Tween 20, and 5% non-fat dry milk. Blots were probed with anti-Myo18A, CD14, SR-A, TLR-2, or CD36 antibodies and then incubated with of HRP-conjugated anti-rabbit or anti-goat secondary antibodies. Bound antibodies were visualized by enhanced chemiluminescence. Relative band intensity was determined by densitometry using a GS-800 Calibrated Densitometer (Bio-Rad) and Quantity One software (Bio-Rad).

Confocal Microscopy

Macrophages grown on glass coverslips were stimulated with 100 ng/mL LPS for set time points, washed with PBS, fixed After 15 min with 4% paraformaldehyde, permeabilized for 10 min in 0.3% Triton X-100/PBS, and then blocked in 10% goat serum/PBS for 60 min at room temperature. Subsequently, the cells were stained with rabbit p65(RelA) antibodies (1:400 dilution) and then with Cy3 conjugated anti-rabbit secondary antibodies (1:500 dilution). Coverslips were mounted on slides by using Prolong mounting medium with DAPI (Life Technologies). Confocal images of fluorescently labeled cells were acquired with a Leica AOBS SP8 laser scanning confocal microscope (Leica, Heidelberg, Germany) using a high resolution Leica 40×/1.3 Plan-Apochromat oil immersion objective at the Penn State College of Medicine Imaging Core. The laser lines used for excitation were continuous wave 405 (for DAPI), nd 80 MHz pulsed 591 (for Cy3). These laser lines were produced by UV diode, 80 MHz white light laser (Leica AOBS SP8 module) respectively and the respective emission signals were collected sequentially using AOBS tunable filters. All images and spectral data measurement data were generated using the highly sensitive HyD detectors (with time gated option). The backscattered emission signals from the sample were delivered through the AOBS tunable filter (to remove irradiated laser), the detection pinhole set to 1 Airy unit (to obtain optimal lateral and axial resolutions), spectral dispersion prism, and finally to the HyD detectors. The width of the slits in front of each HyD could be software adjusted so that each HyD could detect spectral regions spanning from a 10-nm bandwidth up to the overall spectral capacity of the system (400-800 nm). Using this unique option, spectral scanning was performed on all the dyes to confirm signal specificity. Confocal images were analyzed using Imaris Software.

Immunoprecipitation

Control and SP-R210L(DN) cells were cultured in DMEM/10% FBS for 24 hrs in 100 mm dishes and then stimulated with 100 ng/mL LPS for 10, 30, 60 and 120 minutes. After set time periods, media was aspirated and plates were washed twice with cold PBS. Cells were then lysed directly on plate using complete lysis buffer solution (50 mM Tris-HCl, pH 8.0, 150 mM NaCl, 1% NP-40 supplemented with 1 mM MnCl$_2$, 10% glycerol, 1× Cell Signaling Phosphatase/Protease Inhibitor cocktail) on ice for 30 minutes and lysates were then harvested into 1.5 mL Eppendorf tubes. Lysates were centrifuged for 15 minutes at 10,000×g and supernatants were collected without disturbing pellet. Protein concentration of supernatants was measured with BCA Assay and 1.5-2.0 mg of protein per sample was pre-incubated with pre-equilibrated Protein G Agarose beads (Roche) on a rotator for 3 h at 4° C. Beads were removed by centrifugation at 12,000×g for 1 minute and supernatants were transferred into fresh tubes. Pre-adsorbed lysates were then incubated with indicated antibodies or isotype controls on a rotator for lh at 4° C. and then 40-50 μL of pre-equilibrated Protein G Agarose beads (1:1, beads to bed volume) were added to lysates. Samples were incubated on rotator overnight at 4° C. Immunoprecipitation products were centrifuged for 1 minute at 12,000×g and supernatant was discarded. Beads were washed three times in lysis buffer (50 mM Tris-HCl, pH 8.0, 150 mM NaCl, 1% NP-40), and lysis buffer was discarded after each centrifugation. After the last wash, 2× Urea sample buffer (50 mM Tris-HCl, pH 6.8, 1.6% SDS, 7% glycerol, 8 M Urea, 200 mM DTT, 0.01% bromophenol blue) was added directly onto beads. Prepared samples were incubated at room temperature for 20 minutes and heated at 95° C. for 2 minutes. Samples were centrifuged at 12,000×g for 1 minute, proteins were separated on 4-17% SDS-PAGE gels and analyzed by Western Blotting. Immunoprecipitation reactions were carried out using 1.5 mg/mL of protein extract.

Quantitative Real Time RT-PCR

DNAase-treated mRNA was isolated from control and SP-R210$_L$(DN) macrophages using the Qiagen RNAeasy kit. cDNA was synthesized with the high capacity cDNA Reverse Transcription kit following the manufacturer's protocol. Briefly, 1 μg of purified RNA was incubated with 2 μl of 10× buffer, 0.8 μl of 25× dNTPs, 2 μl of 10× random primers, 1 μl of RNAse inhibitor, and 50 U of reverse transcriptase in a final volume of 20 μl. The reaction was incubated for 10 min at 25° C., 2 hrs at 37° C., and inactivated for 5 min at 85° C. The cDNA was diluted five-fold prior to PCR amplification with TaqMan gene expression assays SR-A, CD11b, CD36, and CD14 and 18S ribosomal ® RNA were quantified by real time RT-PCR (qRT-PCR) using TaqMan assays. SP-R210$_L$ mRNA was measured using primers encompassing the PDZ domain containing exon 1 and exon 2 mRNA junction of the Myo18A gene. Common internal primers between exon 18 and 19 were used to quantify both SP-R210$_L$ and SP-R210$_S$ mRNA. Each 20 µl qPCR reaction included 10 µl of 2×
TaqMan Gene Expression Master Mix, 1 µl of 20× TaqMan
Gene Expression Assay, and a total of 10 to 40 ng of cDNA.
The reactions were incubated in 384-well optical plates at
50° C. for 2 min, 95° C. for 10 min, and 40 cycles of 95° C.
for 15 seconds and 60° C. for 1 min. Each sample was
analyzed in triplicate along with no-template controls.
Results were monitored and stored by the ABI PRISM
7900HT sequence detection system (Applied Biosystems) at
the Functional Genomics Core Facility at the Penn State
College of Medicine. Expression of mRNA for each gene
was normalized to 18S rRNA. Data are expressed as relative
mRNA expression in SP-R210(DN) compared to control
cells were calculated using the $2^{-\Delta\Delta Ct}$ method using the
mean ΔCt in control cells as the calibrator [57].

Statistics

Statistical comparison of data was performed using
GraphPad Prism 5.0 software (San Diego, Calif.). Pair-wise
comparisons using the Wilcoxon matched pairs t test were
used to assess statistical differences. P<0.05 were considered
significant.

EXAMPLE 13

This Example demonstrates dominant-negative inhibition
of SP-R210$_L$ mRNA in SP-R210$_L$(DN) cells. Stable expression
of the unique carboxy-terminal (ct) domain of
SP-R210, SP-R210ct [5,6], in Raw264.7 macrophages
resulted in selective dominant-negative (DN) inhibition of
SP-R210$_L$. SP-R210ct isoforms differ by a 15 amino acid
insertion designated as SP-R210$_L$(DN1) and SP-R210$_L$
(DN2) on FIG. 15A. Western blotting (FIG. 15A) and qPCR
analysis (FIG. 15B) demonstrate that stable expression of
either SP-R210ct deletion mutant blocked both mRNA and
protein expression of SP-R210$_L$ by more than 85%. In
contrast, expression of the SP-R210$_S$ variant did not
decrease significantly.

EXAMPLE 14

This Example demonstrates increased levels of innate
receptors on the surface of SP-R210$_L$(DN) cells. We analyzed
whether disruption of SP-R210$_L$ alters expression of
innate receptors. Data presented below represent combined
data from both SP-R210$_L$(DN) cell lines. FIG. 16 demonstrates
20- and 4-fold higher cell-surface levels of SR-A and
CD36 (FIG. 16A), 2- to 3-fold increase in TLR-2 and CD14
(FIG. 16B), and 4- and 2- fold increases in CD11b and
CD11c in SP-R210$_L$(DN) cells (FIG. 16C). Interestingly, the
levels of TLR-4 were 40% lower than control in SP-R210$_L$
(DN) cells (FIG. 16B). The monocytic marker Ly-6C and
uPAR were expressed at low levels and were not different
between control and SP-R210$_L$(DN) cells (FIGS. 16A and
2B). The macrophage differentiation marker F4/80 was not
statistically different compared to control cells (FIG. 16A
and 16C). Further, lack of SP-R210$_L$ did not alter expression
of SIRPα (FIG. 16C). Interestingly, depletion of SP-R210$_L$
resulted in 4- and 20-fold increases in mRNA levels of
CD11b and SR-A (FIG. 16D). The mRNA levels of CD14
and CD36 were similar to control cells (FIG. 16D), even
though surface expression of all four receptors increased
significantly on SP-R210$_L$(DN) cells. Given that CD14
levels increased in SP-R210$_L$(DN) cells, we measured levels
of TNFα after incubation with LPS. Control and SP-R210$_L$
(DN) cells were treated with 100 ng/mL smooth LPS to
trigger macrophage activation via CD14. Intracellular staining
4 hrs after challenge with LPS demonstrates robust
increase in the synthesis of TNFα in both SP-R210$_L$(DN)1
and SP-R210$_L$(DN)2 cells compared to controls (FIG. 17A).
Given that similar results were obtained with SP-R210$_L$
(DN)1 and SP-R210L(DN)2 cells, results described in
SP-R210$_L$(DN) are pooled data from both cell lines in
subsequent studies. FIG. 17B shows that SP-R210$_L$(DN)
cells secreted significantly more TNFα compared to control
cells, consistent with higher levels of CD14. There is
increased functional activity of scavenger receptors consistent
with higher levels of SR-A and CD36 (FIG. 16A) in
SP-R210$_L$(DN) cells. Taken together, these findings indicate
that SP-R210$_L$ acts as an intrinsic repressor of innate receptor
expression and function through both transcriptional and
post-transcriptional mechanisms.

EXAMPLE 15

This Example demonstrates that SP-A enhances expression
of SP-R210 in macrophages.

We analyzed whether SP-A influences expression of its
own receptor, SP-R210. FIG. 18A demonstrates that SP-A
induced expression of both SP-R210$_L$ and SP-R210$_S$ in
control cells in a concentration-dependent manner from
25-100 µg/mL of SP-A, though treatment with low concentration
of 5 µg/mL SP-A appears to be inhibitory. However,
disruption of SP-R210$_L$ attenuated the ability of SP-A to
induce expression of SP-R210$_S$ (FIG. 18B).

To determine whether SP-A modulates SP-R210 expression
in vivo, SP-R210 was assessed on alveolar macrophages
from WT and SP-A−/− mice. SP-R210$_L$ is the main
isoform on alveolar macrophages (FIG. 19A). Notably,
alveolar macrophages from SP-A−/− mice appear to express
similar levels of both SP-R210$_L$ and SP-R210$_S$ Densitometry
analysis showed that WT macrophages express nearly five-
fold higher levels of SP-R210$_L$ compared to SP-A−/− mice
(FIG. 19B). These results indicate that SP-A is an autocrine
regulator of SP-R210 expression in macrophages.

EXAMPLE 16

This Example demonstrates that SP-A preparation influences
responsiveness of macrophages to LPS.

We assessed whether SP-A modifies the inflammatory
response to LPS. For these studies, we used SP-A from
alveolar proteinosis fluid from the same individual purified
by either a modified butanol/octylglucoside method (SP-
Am1) or the isopropyl ether/butanol extraction method
(SP-Am2) using known techniques; SP-Am1 has been
shown to enhance macrophage activation whereas SP-Am2
was shown to be a potent antagonist of multiple toll-like
receptors in several macrophage lines including Raw264.7
macrophages. Control and SP-R210$_L$(DN) macrophages
were exposed to low, 5 µg/mL, or high, 50 µg/mL, SP-Am1
for 24 hrs and subsequently incubated with 100 ng/mL of
LPS (FIG. 20A). FIG. 20A shows that SP-Am1 enhanced
responsiveness to LPS in both control and SP- R210$_L$(DN)
cells at the higher concentration that also enhanced expression
of SP-R210 isoforms (FIG. 19A). SP-Am1 alone at the
low concentration had no effect. In contrast to SP-Am1, FIG.
20B shows that SP-Am2 inhibited LPS-induced TNFα of
both cell lines. The effect of SP-Am2 was examined at 50
µg/mL (FIG. 20B). SP-Am2 contained measurable levels of
LPS, which translates to 1 ng/mL LPS at the 50 µg/mL SP-A
dose. At this concentration, treatment with SP-Am2 alone
produced 20-30% less TNFα in both control and SP-R210$_L$
(DN) cells compared to treatment with equivalent amount of LPS alone (FIG. 20B), consistent with an inhibitory effect of SP-Am2 on the activity of LPS.

To address the different response to LPS in SP-Am1 and SP-Am2-treated macrophages, we evaluated the purity of SP-A preparations from the same and different individuals by silver staining and mass spectrometry (FIG. 27). Silver-staining using a known formaldehyde/glutaraldehyde revealed that SP-Am2 co- isolated with higher levels of low molecular weight proteins of approximately 8-15 kDa (FIG. 27A,C) in the molecular range of surfactant protein B (SP-B). Of note, SP-B is not detectable by Coomassie blue staining and thus SP-A preparations stained with Coomassie would appear pure. We obtained similar results with SP-A from three different individuals (FIG. 27A,C). Western blot analysis confirmed the presence of SP-B co-isolating with both SP-A preparations, although clearly prominent in the SP-Am2 preparation (FIG. 27B). Silver staining with the mass spectrometry compatible SilverQuest from Invitrogen revealed additional protein species above 300 kDa and proteins in the 8-25 kDa range (FIG. 27C). The low molecular weight proteins are prominent in the SP-Am2 preparation with one protein that is present in one SP-Am1 and both SP-Am2 preparations (bands 5 and 6, FIG. 27C). These protein bands in SP-Am1 and SP-Am2 from APF-1 proteinosis material were in-gel digested and identified by MALDI mass spectrometry. The high molecular weight band 1 and 2 proteins were both identified as gp340, a known binding protein for SP-A. Band 3 contains a fragment of SP-A and ferritin light chain, a previously described contaminant in SP-A preparations. Bands 4 in SP-Am1 and bands 6, 7, and 8 in SP-Am2 all contain SP-B. Band 5 contains the aspartyl protease napsin A. In addition to SP-B, bands 6 and 7 also contain the lung-specific napsin A and the nuclear Histone H4, respectively. A blank piece of gel did not yield any protein identifications. Intracellular napsin A has been shown to process pro-SPB in lamellar bodies of alveolar type II epithelial cells, although secreted napsin A may degrade cell surface proteins on alveolar cells. The 30 kDa band 9 only contained SP-A as expected. All proteins were identified at 100 confidence index. These studies indicate that SP-A primes macrophages for enhanced responsiveness to LPS via SP-R210$_L$. However, SP-A treatment leading to either enhanced or reduced responsiveness in vitro can depend on the level of bioactive surfactant components that co-isolate in different SP-A preparations.

EXAMPLE 17

This Example demonstrates that SP-R210$_S$ is a CD14 co-receptor. To determine whether SP-R210 modulates LPS responsiveness via CD14, we performed immuno-precipitation experiments to assess whether SP-R210 interacts physically with CD14 and used neutralizing antibodies to assess responsiveness of control and SP-R210$_L$(DN) macrophages to LPS. We also determined whether SP-R210 interacts with SR-A, CD11b, CD36, and TLR-2 that are increased in SP-R210$_L$(DN) cells (FIG. 16 above). Of these, CD11b, TLR-2, and SR-A are also known to interact with either SP-A and/or SP-R210. We used an affinity purified polyclonal anti-SP-R210 antibody recognizing both SP-R210$_L$ and SP-R210$_S$. FIG. 21A shows that CD14 precipitated with SP-R210 antibodies in both control and SP-R210$_L$(DN) cells. Co-precipitated CD14 was clearly enriched in SP-R210$_L$(DN) cells. Interestingly, SR-A was also enriched in SP-R210$_L$(DN) cells, suggesting that SP-R210$_L$ controls the physical association between SP-R210$_S$ and SR-A as well. In contrast, SP-R210 did not co-precipitate with CD36 and TLR-2 (FIG. 21A) in neither control nor SP-R210$_L$(DN) cells, which serves as an internal control for specificity of SP-R210 interaction with CD14 and SR-A. Reciprocal immuno-precipitation assays using monoclonal CD11b antibodies. FIG. 21B shows that CD11b interacts preferentially with SP-R210$_S$ in control cells. Interestingly, CD11b and SP-R210$_S$ did not co-precipitate in SP-R210$_L$(DN) cells. As a member of the myosin family, SP-R210 is expected to form dimers via the carboxy-terminal coiled-coil domain. However, the preferential, albeit partial, interaction of CD11b with the short SP-R210$_S$ but not the longer SP-R210$_L$ isoform suggests that SP-R210$_L$ and SP-R210$_S$ do not form heterodimers with one another in macrophages. Similar to SP-R210 (FIG. 21A), CD11b did not associate with TLR-2 (FIG. 21B) or with CD36 (not shown). Immunoprecipitation experiments using monoclonal antibodies to SP-R210 show that SP-R210s and CD14 form a stable complex before and after treatment of cells with LPS over two hrs in SP-R210$_L$ (DN) cells (FIG. 21C). Interestingly, LPS treatment increased the level of immunoprecipitated SP-R210 isoforms over time. In contrast, the level of co-precipitated CD14 in control cells was lower to precipitated CD14 than in SP-R210$_L$(DN) cells, suggesting that SP-R210$_L$ controls association of SP-R210$_S$ with CD14 (FIG. 21C).

To evaluate the functional significance of these interactions, we used antibodies to assess activation of macrophages by LPS (FIG. 22). Cells were pre-treated with antibodies and then with 100 ng/mL LPS for 4 hrs followed by intracellular TNFα. Pretreatment of macrophages with SP-R210 and CD11b antibodies did not affect TNFα synthesis in LPS-stimulated control cells. However, SR-A antibodies stimulated TNFα significantly in SP-R210$_L$(DN) compared to control cells by about 30% (FIG. 22). CD14 antibodies blocked TNFα by 50% in both cell lines. Combined treatment with SP-R210 or SR-A antibodies interfered with the ability of CD14 antibodies to inhibit TNFα synthesis in SP-R210$_L$(DN) cells consistent with a close physical proximity between SP-R210$_S$, CD14 and SR-A in SP-R210$_L$(DN) cells as predicted by the immunoprecipitation results above. Consistent with a lack of interaction of SP-R210 with CD11b (FIG. 21B), the CD11b antibody did not interfere with the CD14 inhibitory effect (FIG. 22). Taken together these results indicate that SP-R210$_L$ regulates formation of activating innate receptor complexes in which SP-R210$_S$ and SR-A act as co-receptors of CD14.

EXAMPLE 18

This Example demonstrates that SP-R210 isoforms regulate NFκB activation downstream of TLR-4.

LPS binds CD14 and transfer of LPS to the toll-like receptor TLR-4 results in nuclear translocation and activation of the transcription factor NFκB. The proximal TLR-4 signaling pathway involves myddosome formation followed by activation and degradation of IRAK-1 and downstream phosphorylation and degradation of IκB. Degradation of IκB allows phosphorylation and translocation of NFκB p65(RelA) subunit to the nucleus. Restoration of IκB expression contributes to termination of NFκB signaling. Therefore, we determined whether lack of SP-R210$_L$ alters TLR-4 signaling. The Western analysis on FIG. 23A demonstrates that the kinetics that IRAK1 and IκB degradation were similar between control and SP-R210$_L$(DN) cells. IκB expression was restored after 30 min of LPS stimulation in both cell lines. However, the Western and densitometry analyses of FIGS. 23B and 23C demonstrated that phosphorylation of NFκB at serine 536 was transient in control cells but remained elevated in SP-R210$_L$(DN) cells. Furthermore, confocal fluorescent microscopy analysis on FIGS. 24A and B shows prolonged retention of NFκB in the nucleus of SP-R210$_L$(DN) cells compared to controls. These results indicate that SP-R210 regulates duration of NFκB signaling without affecting early signaling events of TLR-4 activation.

EXAMPLE 19

This Example demonstrates that SP-R210$_L$ and SP-R210$_S$ mediate distinct internalization mechanisms of CD14.

CD14 controls internalization of TLR-4 which may determine TLR-4 activation from either the cell surface or endocytic vesicles. CD14 is also known to mediate macrocropinocytosis-mediated clearance of LPS. We thus asked whether SP-R210 variants influence trafficking of CD14. Control and SP-R210$_L$(DN) macrophages were treated with 100 ng/mL LPS overtime to monitor internalization of CD14. FIG. 25A demonstrates that 25% of CD14 was lost from the cell-surface by 2 hrs after addition of LPS and then new or recycled CD14 returned to the cell-surface by 4 hrs. In contrast, CD14 was replenished faster in SP-R210$_L$(DN) cells (FIG. 25B); only 15% of CD14 was lost from the cell-surface by 30 min with surface CD14 quickly returned to the cell-surface above the levels of unstimulated SP-R210$_L$(DN) cells. To probe the trafficking of CD14 further, we monitored surface CD14 after addition of Dynasore an inhibitor of clathrin and dynamin dependent endocytosis. Dynasore can also inhibit fluid phase endocytosis, endosomal recycling, and constitutive protein secretion in macrophages. FIG. 25B demonstrates that dynasore did not block internalization of CD14 in control cells, consistent with dynasore-insensitive macrocropinocytosis of CD14. However, dynasore blocked replenishment of surface CD14 completely in control cells and partially in SP-R210$_L$(DN) cells, suggesting that dynasore inhibits secretion of newly synthesized CD14. Dynasore, however, reveals a distinct trafficking process in SP-R210$_L$(DN) cells that is characterized by internalization over the first hr after addition of LPS followed by return of CD14 to the cell surface (FIG. 25B), although additional studies will be needed to distinguish whether this represents dynasore-insensitive recycling or secretion of CD14. Differences in trafficking of CD14, however, do not impair endocytosis of TLR-4, although internalization of TLR-4 in SP-R210$_L$(DN) cells slowed after 1 hr of LPS compared to controls (FIG. 25C). Dynasore has been shown to block endocytosis of TLR-4 inhibiting signaling from endocytic compartments. CD14, however, was shown to mediate endocytosis of LPS via 36icropino-cytosis. Therefore, we compared the effects of dynasore and the macrocropinocytosis inhibitor EIPA on the inflammatory response to LPS using intracellular TNFα as a readout of the LPS response. FIG. 25D shows that dynasore and EIPA inhibited TNFα by 40 and 60%, respectively, indicating that internalization of CD14 is required to mediate part of the inflammatory response in control cells. In contrast, SP-R210$_L$(DN) cells were insensitive to inhibition by both dynasore and EIPA (FIG. 25D). Previous studies have shown that the small GTPase rac1 mediates 36 icropinocytosis in macrophages. Accordingly, NSC23766 an inhibitor of the small GTPases rac1 and rac2 blocked TNFα production in both control and SP-R210$_L$(DN) cells. Interestingly, NSC23766 was significantly more effective at inhibiting TNFα in SP-R210$_L$(DN) compared to control cells (FIG. 25D). Taken together, these results indicate that SP-R210$_L$ and SP-R210$_S$ isoforms mediate trafficking of CD14 through distinct macrocropinocytosis-like mechanisms.

It will be recognized from the foregoing that precise regulation of the innate immune system is of paramount importance to respiratory health. Expression and sub-cellular localization of innate receptors determines the outcome of signaling responses that coordinate inflammation with clearance of pathogens. The present findings demonstrate that the SP-A receptor SP-R210$_L$ isoform is an intrinsic modulator of innate receptors in macrophages.

We found that SP-R210$_L$ disruption leads to 2-20-fold increased expression of several innate receptors at both protein (TLR-2, CD11 c, CD36, and CD14) and transcriptional (SR-A, CD11b) levels. Studies on signaling pathways indicate that SP-R210$_S$ and SP-R210$_L$ control activation and deactivation of the transcription factor NFκB, respectively.

Furthermore, we determined that SP-A induced expression of SP-R210 isoforms in a SP-R210$_L$-dependent manner, supporting the notion that SP-A mediates cross-talk between SP-R210 isoforms to modulate responsiveness to inflammatory stimuli. Importantly, studies in alveolar macrophages from SP-A-/- mice indicate that SP-A works in an autocrine fashion to maintain optimal expression levels of SP-R210$_L$, thereby modulating the functional phenotype of alveolar macrophages in vivo.

The present results support the indication that SP-R210$_L$ modulates priming of macrophages as indicated by increased responsiveness to LPS of SP-R210$_L$-deficient cells or after treatment of macrophages with SP-A. We show that exposure of macrophages to SP-A primed macrophages for a greater inflammatory response to subsequent addition of LPS in both control and SP-R210$_L$(DN) cells. In this context, recent studies showed that alveolar macrophages maintain a pro-inflammatory signature, indicating that alveolar macrophages are already primed for increased responsiveness to inflammatory agents in vivo. Conversely, alveolar macrophages are resistant to tolerogenic effects of LPS and other inflammatory stimuli. Here, we show that SP-A enhanced expression of both SP-R210 isoforms which may help balance innate receptors to regulate macrophage activation threshold and readiness of macrophages to respond to inflammatory stimuli appropriately, although SP-R210$_L$ is the main variant on alveolar macrophages that is being affected by SP-A in vivo.

In the present disclosure we show that disruption of SP-R210$_L$ results in decreased levels of surface TLR-4 even though several classes of innate receptors increased. Furthermore, we found different trafficking mechanisms of CD14 between control and SP-R210$_L$(DN) cells, supporting the notion that SP-R210 isoforms are intrinsic regulators of the macrophage functional phenotype.

Additional surfactant components may modify the m icropinocyt response of macrophages. Based on our mass spectrometric characterization of SP-A used for in vitro studies, anti-inflammatory activities of SP-A preparations may be attributed in part to different levels of co-isolating surfactant protein B and napsin A. Side-by-side comparison of SP-A prepared by the commonly used butanol/octylglucoside method (SP-Am1) or a modified isopropyl ether/butanol/ethanol extraction method (SP-Am2) from the same individual revealed higher levels of these proteins in the latter method. However, SP-Am1 prepared from different individuals contain varying levels of co-isolating proteins that could affect downstream assays similar to SP_Am2, although co-isolating SP-B in SP-Am2 was consistently higher (FIG. 27A-C). The presence of gp340, a known extracellular SP-A binding protein, may have limited the effective concentration of biologically active SP-A, although it was found in similar levels in all preparations. We confirmed that, unlike SP-Am1, SP-Am2 does not prime but inhibits LPS-induced TNFα consistently.

The present disclosure addressed the interaction of SP-R210 and CD14 further. Disruption of SP-R210$_L$ revealed distinct mechanisms of CD14 uptake that modulate threshold and duration of macrophage activation in response to LPS. We found that SP-R210$_S$, CD14, and SR-A form a pro-inflammatory complex in SP-R210L(DN) cells as revealed by functional assays using individual or a combination of neutralizing antibodies and immunoprecipitation experiments. Furthermore, we show different trafficking mechanisms of CD14 in control and SP-R210$_L$(DN) cells in which relocation or secretion of CD14 to the cell-membrane after addition of LPS is dynasore sensitive in control cells but dynasore-insensitive in SP-R210$_L$(DN) cells. Initial internalization of CD14 stimulated by LPS is insensitive to dynasore consistent with dynamin-independent internalization. Dynasore, however, partially inhibited LPS-induced TNFα, only in control cells consistent with inhibition of TLR4 dynamin-dependent endocytosis and full activation of the inflammatory response by endosomal TLR4. Induction of TNFα by LPS was also inhibited by the hallmark micropinocytosis inhibitor EIPA in control cells, indicating that macropinocytic internalization of CD14 and/or TLR-4 is needed for downstream activation of the inflammatory response. EIPA and dynasore, however, had no effect on the LPS response in SP-R210$_L$(DN) cells, suggesting deployment of a novel inflammatory mechanism when SP-R210$_L$ expression is attenuated. Interestingly, inhibition of the small GTPase rac1 reduced LPS activation in both cells although more effectively in SP-R210$_L$(DN) cells, supporting the notion that rac1 is a common downstream effector of LPS internalization and signaling. Rac1 is one of several GTPases that mediate macrocropinocytosis. On the other hand, rac1 may contribute to prolonged activation of NFκB in SP-R210$_L$(DN) cells downstream of TLR-4 or SR-A.

Without intending to be bound by any particular theory, taken together, the present findings support the model depicted on FIG. 26. In this model, SP-R210$_L$ interacts with the rac1 signaling pathway to enhance macrocropinocytosis and clearance of LPS via CD14 with moderate activation of endosomal TLR-4. We propose that the ability of SP-A to maintain high levels of SP-R210$_L$, enhancing the capacity of alveolar macrophages to clear LPS without overt inflammation, provides a mechanistic explanation for the anti-inflammatory role of SP-A in vivo. In turn, SP-R210$_L$ modulates expression and localization of innate receptors priming macrophages for an appropriate response at increased levels of inflammatory agents in the environment. However, in the absence of SP-R210$_L$-mediated regulation, the response to LPS is mediated through a pro-inflammatory complex between SP-R210$_S$, CD14, and SR-A in which SR-A is responsible for macrocropinocytosis-like internalization of LPS and prolonged activation of the rac-1 signaling pathway. The present disclosure therefore indicates that differential expression of SP-R210 variants determines the inflammatory phenotype of macrophages.

EXAMPLE 20

This Example demonstrates that monoclonal anti-SP-R210 antibodies enhance recovery for influenza pneumonia. Data are summarized in FIG. 28 and show effects on body weight (28A) and survival (28B). To obtain the data, mice were injected intraperitoneally with 100 μg of antibodies or 100 μl PBS vehicle 24 hrs before infection with 3LD50 of influenza virus H1N1 PR8. Mouse morbidity and weight were monitored daily. IgG1: isotype control antibody; P2H10: anti-SP-R210$_S$ antibody; P4G4: anti-SP-R210$_{L+S}$ antibody. N=5 mice per group. As shown in FIG. 28B, monoclonal SP-R210 antibodies enhanced survival from lethal challenge with influenza infection. Mice were injected intraperitoneally with 100 μg of antibodies or 100 μl PBS vehicle 24 hrs before infection with 3LD50 of influenza virus H1N1 PR8. Mouse morbidity and weight were monitored daily. IgG1: isotype control antibody; P2H10: anti-SP-R210$_S$ antibody; P4G4: anti-SP-R210$_{L+S}$ antibody. N=5 mice per group. *p<0.04

As shown in FIG. 29, deletion of SP-R210 in CD103+ dendritic cells enhances recovery from IAV infection and recruitment of effector T lymphocytes. To obtain the data shown in FIG. 29, mice carrying a floxed SP-R210 knockin allele were crossed with Clec9A-Cre mice to disrupt SP-R210 in CD103+ DCs. WT littermate controls and DC SP-R210-deficient mice were infected with a sub-lethal dose of 0.75 LD50 of IAV PR8 intranasally. (A) Body weight was monitored over time for 14 days. N=4-12 mice per group per time point. At 3, 7 and 14 days after infection 4 mice from each group were used to obtain lung lavage. The number of effector T lymphocytes (B) and total number of lymphocytes (C) was determined by flow cytometry. Data shown in A-C are means±SEM.

What is claimed is:

1. A monoclonal antibody (mAb) or fragment thereof that binds with specificity to surfactant protein A SP-R210 receptor, comprising:

(I) a variable heavy chain sequence comprising:
a) a heavy chain complementarity determining region 1 (P2H10-HCDR1) comprising the sequence GYIFSDYYMR (SEQ ID NO:3); and
b) a heavy chain complementarity determining region 2 (P2H10-HCDR2) comprising the sequence DINPKNGDTFYNQKFKGK (SEQ ID NO:4); and
c) a heavy chain complementarity determining region 3 (P2H10-HCDR3) comprising the sequence REGD (SEQ ID NO:5); and a variable light chain sequence comprising:
d) a light chain complementarity determining region 1 (P2H10-LCDR1) comprising the sequence RSSQTILHSNGNTYLE (SEQ ID NO:6); and
e) a light chain complementarity determining region 2 (P2H10-LCDR2) comprising the sequence KVSKRFS (SEQ ID NO:7): and
f) a light chain complementarity determining region 3 (P2H10-LCDR3) comprising the sequence LQGSHVPLT (SEQ ID NO:8):
or:

(II) a variable heavy chain sequence comprising:
i) a heavy chain complementarity determining region 1 (P4G4-HCDR1) comprising the sequence GYTFTDYAMH (SEQ ID NO:9): and
ii) a heavy chain complementarity determining region 2 P4G4-HCDR2) comprising the sequence VISTYNGNTKYNQKFKD (SEQ ID NO:10: and
iii) a heavy chain complementarity determining region 3 P4G4-HCDR3) comprising the sequence ARTDYDNGDYVMDY (SEQ ID NO:11):and a variable light chain sequence comprising:
iv) a light chain complementarity determining region 1 (P4G4-LCDR1) comprising the sequence KASQDINNYLS (SEQ ID NO:12): and
v) a light chain complementarity determining region 2 (P4G4-LCDR2) comprising the sequence RANRLVD (SEQ ID NO:13): and
vi) a light chain complementarity determining region 3 (P4G4-LCDR3) comprising the sequence LQYDEFPLT (SEQ ID NO:14).

2. The monoclonal antibody or fragment thereof of claim 1, wherein the monoclonal antibody or fragment of (I) binds with specificity to only SP-R210S isoform of the SP-R210 receptor, and wherein the monoclonal antibody or fragment thereof of (II) binds with specificity to SP-R210S and SP-R210L isoforms of the SP-R210 receptor.

3. The monoclonal antibody or fragment thereof of claim 1, wherein the monoclonal antibody or fragment thereof is partially or fully humanized.

4. The monoclonal antibody claim 3 comprising a human IgG constant region.

5. A method for treating a viral or bacterial infection in an individual in need thereof comprising administering to the individual an effective amount of a composition comprising a monoclonal antibody or fragment thereof of claim 1.

6. The method of claim 5, wherein the individual is in need for treatment for a viral influenza infection.

7. The method of claim 6, wherein the individual has pneumonia associated with the viral influenza infection.

8. An expression vector encoding a monoclonal antibody or fragment thereof of claim 1.

9. An in vitro cell culture, wherein cells in the cell culture express the monoclonal antibody or fragment thereof according to claim 1.

10. A hybridoma comprising a polynucleotide sequence encoding a monoclonal antibody of claim 1.

11. A pharmaceutical composition comprising a monoclonal antibody or fragment thereof of claim 1.

* * * * *

SEQUENCE LISTING

```
<160> NUMBER OF SEQ ID NOS: 30

<210> SEQ ID NO 1
<211> LENGTH: 103
<212> TYPE: PRT
<213> ORGANISM: mouse

<400> SEQUENCE: 1

Glu Asp Glu Met Glu Ser Asp Glu Asn Glu Asp Leu Ile Asn Ser Glu
1               5                   10                  15

Gly Asp Ser Asp Val Asp Ser Glu Leu Glu Asp Arg Val Asp Gly Val
            20                  25                  30

Lys Ser Trp Leu Ser Lys Asn Lys Gly Pro Ser Lys Ala Pro Ser Asp
        35                  40                  45

Asp Gly Ser Leu Lys Ser Ser Ser Pro Thr Ser His Trp Lys Pro Leu
    50                  55                  60
```

```
Ala Pro Asp Pro Ser Asp Glu His Asp Pro Val Asp Ser Ile Phe
65                  70                  75                  80

Arg Pro Arg Phe Ser His Ser Tyr Leu Ser Asp Ser Thr Glu Ala
                85                  90                  95

Lys Leu Thr Glu Thr Ser Ala
            100
```

<210> SEQ ID NO 2
<211> LENGTH: 118
<212> TYPE: PRT
<213> ORGANISM: mouse

<400> SEQUENCE: 2

```
Glu Asp Glu Met Glu Ser Asp Glu Asn Glu Asp Leu Ile Asn Ser Leu
1               5                   10                  15

Gln Asp Met Val Thr Lys Tyr Gln Lys Lys Asn Lys Leu Glu Gly
            20                  25                  30

Asp Ser Asp Val Asp Ser Glu Leu Glu Asp Arg Val Asp Arg Val Lys
        35                  40                  45

Ser Trp Leu Ser Lys Asn Lys Gly Pro Ser Lys Ala Pro Ser Asp Asp
50                  55                  60

Gly Ser Leu Lys Ser Ser Ser Pro Thr Ser His Trp Lys Pro Leu Ala
65                  70                  75                  80

Pro Asp Pro Ser Asp Asp Glu His Asp Pro Val Asp Ser Ile Ser Arg
                85                  90                  95

Pro Arg Phe Ser His Ser Tyr Leu Ser Asp Ser Asp Thr Glu Ala Lys
            100                 105                 110

Leu Thr Glu Thr Ser Ala
        115
```

<210> SEQ ID NO 3
<211> LENGTH: 10
<212> TYPE: PRT
<213> ORGANISM: mouse

<400> SEQUENCE: 3

```
Gly Tyr Ile Phe Ser Asp Tyr Tyr Met Arg
1               5                   10
```

<210> SEQ ID NO 4
<211> LENGTH: 18
<212> TYPE: PRT
<213> ORGANISM: mouse

<400> SEQUENCE: 4

```
Asp Ile Asn Pro Lys Asn Gly Asp Thr Phe Tyr Asn Gln Lys Phe Lys
1               5                   10                  15

Gly Lys
```

<210> SEQ ID NO 5
<211> LENGTH: 4
<212> TYPE: PRT
<213> ORGANISM: mouse

<400> SEQUENCE: 5

```
Arg Glu Gly Asp
1
```

<210> SEQ ID NO 6

```
<211> LENGTH: 16
<212> TYPE: PRT
<213> ORGANISM: mouse

<400> SEQUENCE: 6

Arg Ser Ser Gln Thr Ile Leu His Ser Asn Gly Asn Thr Tyr Leu Glu
1               5                   10                  15

<210> SEQ ID NO 7
<211> LENGTH: 7
<212> TYPE: PRT
<213> ORGANISM: mouse

<400> SEQUENCE: 7

Lys Val Ser Lys Arg Phe Ser
1               5

<210> SEQ ID NO 8
<211> LENGTH: 9
<212> TYPE: PRT
<213> ORGANISM: mouse

<400> SEQUENCE: 8

Leu Gln Gly Ser His Val Pro Leu Thr
1               5

<210> SEQ ID NO 9
<211> LENGTH: 10
<212> TYPE: PRT
<213> ORGANISM: mouse

<400> SEQUENCE: 9

Gly Tyr Thr Phe Thr Asp Tyr Ala Met His
1               5                   10

<210> SEQ ID NO 10
<211> LENGTH: 17
<212> TYPE: PRT
<213> ORGANISM: mouse

<400> SEQUENCE: 10

Val Ile Ser Thr Tyr Asn Gly Asn Thr Lys Tyr Asn Gln Lys Phe Lys
1               5                   10                  15

Asp

<210> SEQ ID NO 11
<211> LENGTH: 14
<212> TYPE: PRT
<213> ORGANISM: mouse

<400> SEQUENCE: 11

Ala Arg Thr Asp Tyr Asp Asn Gly Asp Tyr Val Met Asp Tyr
1               5                   10

<210> SEQ ID NO 12
<211> LENGTH: 11
<212> TYPE: PRT
<213> ORGANISM: mouse

<400> SEQUENCE: 12

Lys Ala Ser Gln Asp Ile Asn Asn Tyr Leu Ser
1               5                   10

<210> SEQ ID NO 13
```

```
<211> LENGTH: 7
<212> TYPE: PRT
<213> ORGANISM: mouse

<400> SEQUENCE: 13

Arg Ala Asn Arg Leu Val Asp
1               5

<210> SEQ ID NO 14
<211> LENGTH: 9
<212> TYPE: PRT
<213> ORGANISM: mouse

<400> SEQUENCE: 14

Leu Gln Tyr Asp Glu Phe Pro Leu Thr
1               5

<210> SEQ ID NO 15
<211> LENGTH: 8
<212> TYPE: PRT
<213> ORGANISM: mouse

<400> SEQUENCE: 15

Lys Tyr Gln Lys Lys Lys Asn Lys
1               5

<210> SEQ ID NO 16
<211> LENGTH: 9
<212> TYPE: PRT
<213> ORGANISM: mouse

<400> SEQUENCE: 16

Val Lys Ser Trp Leu Ser Lys Asn Lys
1               5

<210> SEQ ID NO 17
<211> LENGTH: 8
<212> TYPE: PRT
<213> ORGANISM: mouse
<220> FEATURE:
<221> NAME/KEY: misc_feature
<222> LOCATION: (2)..(5)
<223> OTHER INFORMATION: Xaa can be any naturally occurring amino acid

<400> SEQUENCE: 17

Lys Xaa Xaa Xaa Xaa Lys Asn Lys
1               5

<210> SEQ ID NO 18
<211> LENGTH: 8
<212> TYPE: PRT
<213> ORGANISM: mouse

<400> SEQUENCE: 18

Asp Leu Ile Asn Ser Leu Gln Asp
1               5

<210> SEQ ID NO 19
<211> LENGTH: 118
<212> TYPE: PRT
<213> ORGANISM: mouse

<400> SEQUENCE: 19

Glu Asp Glu Met Glu Ser Asp Glu Asn Glu Asp Leu Ile Asn Ser Leu
1               5                   10                  15
```

Gln Asp Met Val Thr Lys Tyr Gln Lys Lys Asn Lys Leu Glu Gly
                20                  25                  30

Asp Ser Asp Val Asp Ser Glu Leu Glu Asp Arg Val Asp Gly Val Lys
            35                  40                  45

Ser Trp Leu Ser Lys Asn Lys Gly Pro Ser Lys Ala Pro Ser Asp Asp
    50                  55                  60

Gly Ser Leu Lys Ser Ser Pro Thr Ser His Trp Lys Pro Leu Ala
65                  70                  75                  80

Pro Asp Pro Ser Asp Glu His Asp Pro Val Asp Ser Ile Ser Arg
                85                  90                  95

Pro Arg Phe Ser His Ser Tyr Leu Ser Asp Ser Asp Thr Glu Ala Lys
            100                 105                 110

Leu Thr Glu Thr Ser Ala
            115

<210> SEQ ID NO 20
<211> LENGTH: 103
<212> TYPE: PRT
<213> ORGANISM: mouse

<400> SEQUENCE: 20

Glu Asp Glu Met Glu Ser Asp Glu Asn Glu Asp Leu Ile Asn Ser Glu
1               5                   10                  15

Gly Asp Ser Asp Val Asp Ser Glu Leu Glu Asp Arg Val Asp Gly Val
                20                  25                  30

Lys Ser Trp Leu Ser Lys Asn Lys Gly Pro Ser Lys Ala Pro Ser Asp
            35                  40                  45

Asp Gly Ser Leu Lys Ser Ser Pro Thr Ser His Trp Lys Pro Leu
    50                  55                  60

Ala Pro Asp Pro Ser Asp Asp Glu His Asp Pro Val Asp Ser Ile Ser
65                  70                  75                  80

Arg Pro Arg Phe Ser His Ser Tyr Leu Ser Asp Ser Asp Thr Glu Ala
                85                  90                  95

Lys Leu Thr Glu Thr Ser Ala
            100

<210> SEQ ID NO 21
<211> LENGTH: 118
<212> TYPE: PRT
<213> ORGANISM: human

<400> SEQUENCE: 21

Glu Asp Glu Met Glu Ser Asp Glu Asn Glu Asp Leu Ile Asn Ser Leu
1               5                   10                  15

Gln Asp Met Val Thr Lys Tyr Gln Lys Arg Lys Asn Lys Leu Glu Gly
                20                  25                  30

Asp Ser Asp Val Asp Ser Glu Leu Glu Asp Arg Val Asp Gly Val Lys
            35                  40                  45

Ser Trp Leu Ser Lys Asn Lys Gly Pro Ser Lys Ala Ala Ser Asp Asp
    50                  55                  60

Gly Ser Leu Lys Ser Ser Pro Thr Ser Tyr Trp Lys Ser Leu Ala
65                  70                  75                  80

Pro Asp Arg Ser Asp Asp Glu His Asp Pro Leu Asp Asn Thr Ser Arg
                85                  90                  95

Pro Arg Tyr Ser His Ser Tyr Leu Ser Asp Ser Asp Thr Glu Ala Lys
            100                 105                 110

Leu Thr Glu Thr Asn Ala
        115

<210> SEQ ID NO 22
<211> LENGTH: 103
<212> TYPE: PRT
<213> ORGANISM: human

<400> SEQUENCE: 22

Glu Asp Glu Met Glu Ser Asp Glu Asn Glu Asp Leu Ile Asn Ser Glu
1               5                   10                  15

Gly Asp Ser Asp Val Asp Ser Glu Leu Glu Asp Arg Val Asp Gly Val
            20                  25                  30

Lys Ser Trp Leu Ser Lys Asn Lys Gly Pro Ser Lys Ala Ala Ser Asp
        35                  40                  45

Asp Gly Ser Leu Lys Ser Ser Pro Thr Ser Tyr Trp Lys Ser Leu
    50                  55                  60

Ala Pro Asp Arg Ser Asp Asp Glu His Asp Pro Leu Asp Asn Thr Ser
65                  70                  75                  80

Arg Pro Arg Tyr Ser His Ser Tyr Leu Ser Asp Ser Asp Thr Glu Ala
                85                  90                  95

Lys Leu Thr Glu Thr Asn Ala
            100

<210> SEQ ID NO 23
<211> LENGTH: 112
<212> TYPE: PRT
<213> ORGANISM: mouse

<400> SEQUENCE: 23

Glu Val Lys Leu Glu Glu Ser Gly Pro Glu Leu Val Lys Pro Gly Ala
1               5                   10                  15

Ser Val Lys Met Ser Cys Lys Ala Ser Gly Tyr Ile Phe Ser Asp Tyr
            20                  25                  30

Tyr Met Arg Trp Val Lys Gln Ser His Gly Lys Ser Leu Glu Trp Ile
        35                  40                  45

Gly Asp Ile Asn Pro Lys Asn Gly Asp Thr Phe Tyr Asn Gln Lys Phe
    50                  55                  60

Lys Gly Lys Ala Thr Leu Thr Val Asp Lys Ser Ser Thr Thr Ala Tyr
65                  70                  75                  80

Met Gln Leu Asn Arg Leu Thr Ser Glu Asp Ser Ala Val Tyr Tyr Cys
                85                  90                  95

Val Arg Glu Gly Asp Trp Gly Gln Gly Thr Thr Leu Thr Val Ser Ser
            100                 105                 110

<210> SEQ ID NO 24
<211> LENGTH: 336
<212> TYPE: DNA
<213> ORGANISM: mouse

<400> SEQUENCE: 24
gaggtaaagc tggaggagtc tggacctgag ctggtgaagc ctggggcttc agtgaagatg       60
tcctgcaagg cttctggata catcttctct gattattata tgaggtgggt gaagcagagc      120
catggaaaga gccttgagtg gattggagat attaatccta agaatggtga ctttctctac      180
aaccagaagt tcaagggcaa ggccacattg actgtagata aatcttccac cacagcctac      240
atgcagctca acaggctgac atctgaggac tctgcagtct attattgtgt aagagagggg      300

```
gactggggcc aaggcaccac tctcacagtc tcctca                               336
```

<210> SEQ ID NO 25
<211> LENGTH: 112
<212> TYPE: PRT
<213> ORGANISM: mouse

<400> SEQUENCE: 25

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Thr Ile Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Val Glu Asp Leu Gly Val Tyr Tyr Cys Leu Gln Gly
                85                  90                  95

Ser His Val Pro Leu Thr Phe Gly Ala Gly Thr Lys Leu Glu Val Lys
            100                 105                 110
```

<210> SEQ ID NO 26
<211> LENGTH: 336
<212> TYPE: DNA
<213> ORGANISM: mouse

<400> SEQUENCE: 26

```
gatattgtga tgacacagtc tccactctcc ctgcctgtca gtcttggaga tcaagcctcc    60
atctcttgca gatctagtca gaccatttta catagtaatg gaaacaccta tttagaatgg   120
tacctgcaga aaccaggcca gtctccaaag ctcctgatct ataaagtttc caaacgattt   180
tctggggtcc cagacaggtt cagtggcagt ggatcaggga cagatttcac actcaagatc   240
agcagagtgg aggttgagga tctgggagtt tattactgcc ttcaaggttc acatgttccg   300
ctcacgttcg gtgctgggac caagctggag gtgaaa                             336
```

<210> SEQ ID NO 27
<211> LENGTH: 121
<212> TYPE: PRT
<213> ORGANISM: mouse

<400> SEQUENCE: 27

```
Glu Val Lys Leu Glu Glu Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Asn Gly Asn Thr Lys Tyr Asn Gln Lys Phe
    50                  55                  60

Lys Asp Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Thr Asp Tyr Asp Asn Gly Asp Tyr Val Met Asp Tyr Trp Gly
            100                 105                 110
```

Gln Gly Thr Ser Val Thr Val Ser Ser
        115                 120

<210> SEQ ID NO 28
<211> LENGTH: 360
<212> TYPE: DNA
<213> ORGANISM: mouse

<400> SEQUENCE: 28
gaggtaaagc tggaggagtc tgggcctgag gtggtgaggc ctggggtctc agtgaagatt      60
tcctgcaagg gttccggcta cacattcact gattatgcta tgcactgggt gaagcagagt     120
catgcaaaga gtctagagtg gattggagtt attagtactt acaatggtaa tacaaagtac     180
aaccagaagt ttaaggacaa ggccacaatg actgtagaca atcctccag cacagcctat      240 atggaacttg ccagattgac atctgaggat tctgccatct attactgtgc aaggacggac     300
tatgataacg ggactatgt tatggactac tggggtcaag aacctcagt caccgtctcc       360

<210> SEQ ID NO 29
<211> LENGTH: 107
<212> TYPE: PRT
<213> ORGANISM: mouse

<400> SEQUENCE: 29

Asp Ile Val Leu Thr Gln Ser Pro Ser Ser Met Tyr Thr Ser Leu Gly
1               5                   10                  15

Gly Arg Val Thr Ile Thr Cys Lys Ala Ser Gln Asp Ile Asn Asn Tyr
            20                  25                  30

Leu Ser Trp Phe Gln Gln Lys Pro Gly Lys Ser Pro Lys Thr Leu Ile
        35                  40                  45

Asn Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
            100                 105

<210> SEQ ID NO 30
<211> LENGTH: 321
<212> TYPE: DNA
<213> ORGANISM: mouse

<400> SEQUENCE: 30
gacattgtgc tgacccagtc tccatcttcc atgtatacat ctctaggagg gagagtcact      60
atcacttgca aggcgagtca ggacattaat aactatttaa gctggttcca gcagaaacca     120
gggaaatctc ctaagaccct gatcaatcgt gcaaacagat tggtagatgg ggtcccatca     180
aggttcagtg gcagtggatc tgggcaagat tattctctca ccatcagcag cctggagtat     240
gaagatatgg gaatttatta ttgtctacaa tatgatgagt ttccgctcac gttcggtgct     300
gggaccaagc tggagctgaa a                                              321